United States Patent
Narayan et al.

(10) Patent No.: US 10,926,068 B2
(45) Date of Patent: Feb. 23, 2021

(54) MAGNETIC PUNCTURE ACCESS AND DELIVERY SYSTEMS AND METHODS

(71) Applicant: MagPAD, LLC, New York, NY (US)

(72) Inventors: Rajeev L. Narayan, New York, NY (US); Alon S. Aharon, New York, NY (US); John Leo, New York, NY (US)

(73) Assignee: MagPAD, LLC, New York, NY (US)

( * ) Notice: Subject to any disclaimer, the term of this patent is extended or adjusted under 35 U.S.C. 154(b) by 0 days.

(21) Appl. No.: 16/849,898

(22) Filed: Apr. 15, 2020

(65) Prior Publication Data

US 2020/0238058 A1   Jul. 30, 2020

Related U.S. Application Data

(63) Continuation-in-part of application No. PCT/US2019/056378, filed on Oct. 15, 2019.

(60) Provisional application No. 62/745,952, filed on Oct. 15, 2018.

(51) Int. Cl.
*A61M 27/00* (2006.01)
*A61M 25/01* (2006.01)

(52) U.S. Cl.
CPC ...... *A61M 27/002* (2013.01); *A61M 25/0127* (2013.01); *A61M 25/0147* (2013.01)

(58) Field of Classification Search
CPC ............. A61M 1/3655; A61M 27/002; A61M 25/0068; A61M 25/0082; A61M 25/0127; A61M 25/0147; A61M 2025/0166; A61B 17/11; A61B 17/320783; A61B 2017/00778; A61B 2017/00876; A61B 2017/1139
See application file for complete search history.

(56) References Cited

U.S. PATENT DOCUMENTS

| | | |
|---|---|---|
| 5,895,404 A | 4/1999 | Ruiz |
| 6,099,542 A | 8/2000 | Cohn et al. |
| 6,159,225 A | 12/2000 | Makower |
| 6,190,353 B1 | 2/2001 | Makower et al. |
| 6,379,319 B1 | 4/2002 | Garibotto et al. |
| 6,464,665 B1 | 10/2002 | Heuser |
| 6,655,386 B1 | 12/2003 | Makower et al. |
| 6,669,709 B1 | 12/2003 | Cohn et al. |
| 6,746,464 B1 | 6/2004 | Makower |
| 7,059,330 B1 | 6/2006 | Makower et al. |

(Continued)

FOREIGN PATENT DOCUMENTS

| | | |
|---|---|---|
| WO | WO 1997/012555 | 4/1997 |
| WO | WO 1998/001635 | 1/1998 |

(Continued)

OTHER PUBLICATIONS

US 10,625,052 B2, 04/2020, Pate (withdrawn)
International Search Report for Application No. PCT/US2019/056378 dated Nov. 25, 2019 in 18 pages.

*Primary Examiner* — Robert A Lynch
(74) *Attorney, Agent, or Firm* — Knobbe Martens Olson & Bear, LLP

(57) ABSTRACT

Some embodiments are directed to magnetic puncture access and delivery systems and methods, including creating a passageway, such as a fistula, between two vessels or segments of a vessel. A system can include two catheters, each carrying a plurality of magnets along a longitudinal axis of each catheter.

20 Claims, 69 Drawing Sheets

(56) References Cited

U.S. PATENT DOCUMENTS

| | | |
|---|---|---|
| 7,134,438 B2 | 11/2006 | Makower |
| 7,316,655 B2 | 1/2008 | Garibotto et al. |
| 7,374,567 B2 | 5/2008 | Heuser |
| 7,387,636 B2 | 6/2008 | Cohn et al. |
| 7,691,144 B2 | 4/2010 | Chang et al. |
| 7,967,808 B2 | 6/2011 | Fitzgerald et al. |
| 8,062,321 B2 | 11/2011 | Heuser et al. |
| 8,163,013 B2 | 4/2012 | Machold et al. |
| 8,187,207 B2 | 5/2012 | Machold et al. |
| 8,236,014 B2 | 8/2012 | Brenneman et al. |
| 8,641,747 B2 | 2/2014 | Brenneman et al. |
| 8,858,622 B2 | 10/2014 | Machold et al. |
| 8,876,699 B2 | 11/2014 | Sato et al. |
| 8,960,858 B2 | 2/2015 | Lutz |
| 8,979,925 B2 | 3/2015 | Chang et al. |
| 9,017,323 B2 | 4/2015 | Miller et al. |
| 9,039,702 B2 | 5/2015 | Miller et al. |
| 9,179,896 B2 | 11/2015 | Machold et al. |
| 9,259,340 B2 | 2/2016 | Heuser et al. |
| 9,456,820 B2 | 10/2016 | Gagner et al. |
| 9,486,276 B2 | 11/2016 | Rios et al. |
| 9,498,331 B2 | 11/2016 | Chang et al. |
| 9,597,184 B2 | 3/2017 | Machold et al. |
| 9,801,635 B2 | 10/2017 | Gagner et al. |
| 10,045,817 B2 | 8/2018 | Miller |
| 10,154,844 B2 | 12/2018 | Sharma |
| 10,159,487 B2 | 12/2018 | Gagner et al. |
| 10,172,621 B2 | 1/2019 | Machold et al. |
| 10,219,902 B2 | 3/2019 | Machold et al. |
| 10,219,905 B2 | 3/2019 | Chang et al. |
| 10,265,206 B2 | 4/2019 | Heuser et al. |
| 10,398,437 B2 | 9/2019 | Machold et al. |
| 10,507,302 B2 | 12/2019 | Leeflang et al. |
| 10,543,308 B2 | 1/2020 | Lenihan et al. |
| 10,667,817 B2 | 6/2020 | Gagner et al. |
| 2003/0181843 A1 | 9/2003 | Bibber et al. |
| 2005/0222489 A1 | 10/2005 | Randert et al. |
| 2005/0228422 A1 | 10/2005 | Machold et al. |
| 2005/0277965 A1 | 12/2005 | Brenneman et al. |
| 2006/0106278 A1 | 5/2006 | Machold et al. |
| 2006/0106279 A1 | 5/2006 | Machold et al. |
| 2007/0185567 A1 | 8/2007 | Heuser et al. |
| 2007/0203515 A1 | 8/2007 | Heuser |
| 2007/0203572 A1 | 8/2007 | Heuser et al. |
| 2008/0051626 A1 | 2/2008 | Sato et al. |
| 2008/0091059 A1 | 4/2008 | Machold et al. |
| 2008/0091264 A1 | 4/2008 | Machold et al. |
| 2008/0161901 A1 | 7/2008 | Heuser et al. |
| 2008/0161904 A1 | 7/2008 | Heuser et al. |
| 2009/0184088 A1 | 7/2009 | Carlson |
| 2009/0287179 A1 | 11/2009 | Machold et al. |
| 2009/0326648 A1 | 12/2009 | Machold et al. |
| 2010/0161044 A1 | 6/2010 | Chang et al. |
| 2012/0150092 A1 | 6/2012 | McAllister et al. |
| 2012/0302935 A1* | 11/2012 | Miller ............ A61B 17/320016 604/8 |
| 2014/0094791 A1* | 4/2014 | Hull ........... A61B 18/18 606/33 |
| 2014/0222138 A1 | 8/2014 | Machold et al. |
| 2014/0276335 A1 | 9/2014 | Pate |
| 2015/0057687 A1 | 2/2015 | Gittard et al. |
| 2015/0297259 A1* | 10/2015 | Matsubara ............ A61M 25/04 606/185 |
| 2016/0067043 A1 | 3/2016 | Machold et al. |
| 2017/0119494 A1 | 5/2017 | Vazales et al. |
| 2017/0156864 A1 | 6/2017 | Chang et al. |
| 2017/0202603 A1 | 7/2017 | Cohn et al. |
| 2017/0202616 A1 | 7/2017 | Pate et al. |
| 2018/0133441 A1 | 5/2018 | Kellerman |
| 2018/0344396 A1 | 12/2018 | Miller et al. |
| 2019/0038410 A1 | 2/2019 | Machold et al. |
| 2019/0133678 A1 | 5/2019 | Pate et al. |
| 2019/0269474 A1 | 9/2019 | Gittard et al. |
| 2019/0328392 A1 | 10/2019 | Sharma |
| 2020/0061338 A1 | 2/2020 | Pate |
| 2020/0114060 A1 | 4/2020 | Vartanian |
| 2020/0129318 A1 | 4/2020 | Duval et al. |
| 2020/0144121 A1 | 5/2020 | Lichtensteiger et al. |
| 2020/0161144 A1 | 5/2020 | Lenihan et al. |

FOREIGN PATENT DOCUMENTS

| | | |
|---|---|---|
| WO | WO 2018/236835 | 12/2018 |
| WO | WO 2020/081597 | 4/2020 |

\* cited by examiner

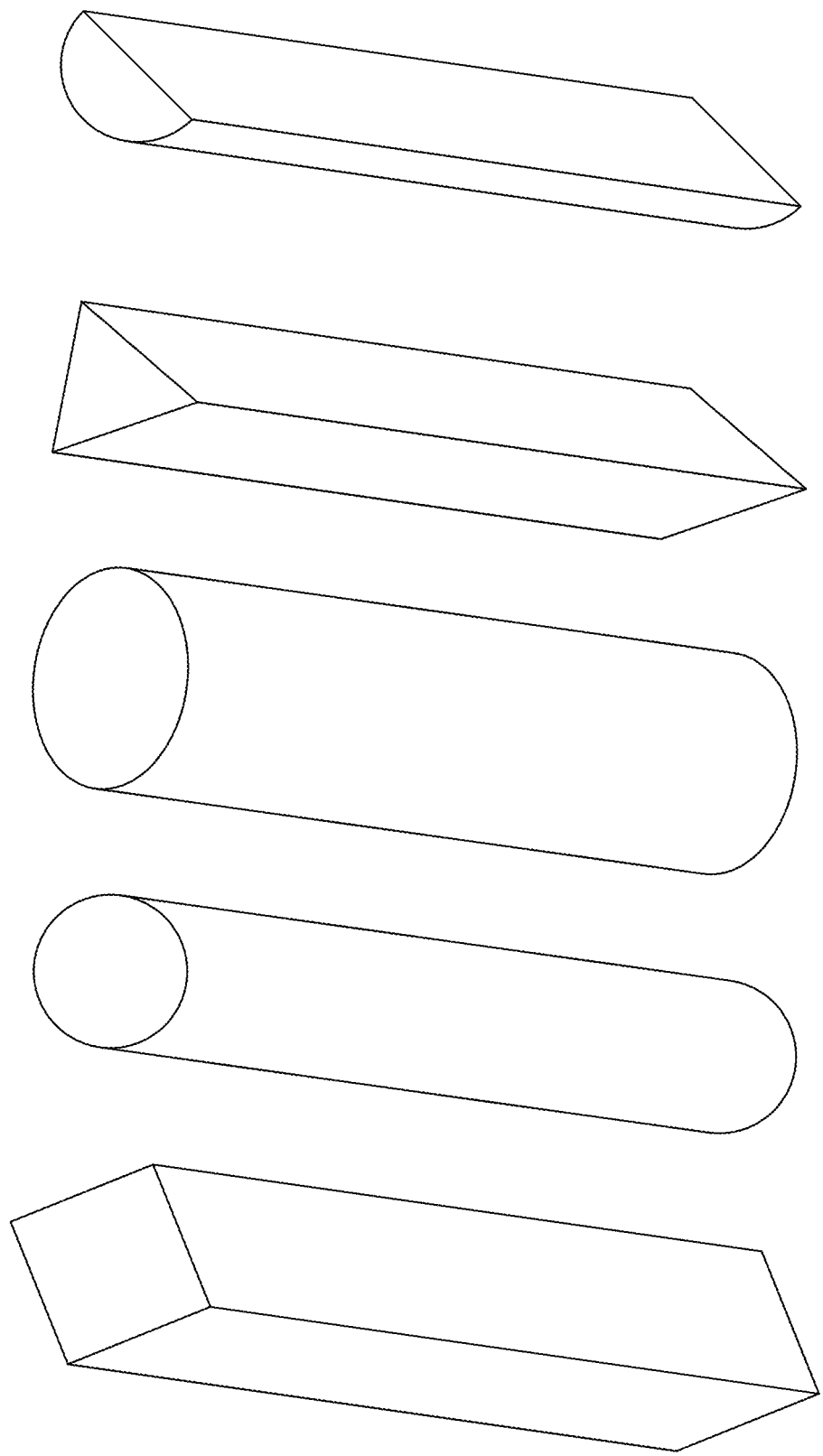

MAGNETIC PUNCTURE ACCESS AND DELIVERY SYSTEMS AND METHODS

PRIORITY CLAIM

This application claims the benefit under 35 U.S.C. § 120 as a continuation-in-part application of PCT App. No. PCT/US2019/056378 filed on Oct. 15, 2019, which in turn claims the benefit under 35 U.S.C. § 119(e) as a nonprovisional application of U.S. Prov. App. No. 62/745,952 filed on Oct. 15, 2018, which is hereby incorporated by reference in its entirety.

BACKGROUND

In order to cross, for example, the venous access side to the arterial access side there is a need to make accessing simpler and more accessible. There is also a need to approximate two body lumens, such as vessels including but not limited to the aorta and IVC in order to perform this access (or other arterial and venous structures—e.g., axillary/subclavian). In some embodiments, magnets can be advantageously utilized for this and other indications.

SUMMARY

In some embodiments, disclosed herein is a catheter system, comprising: a first catheter comprising a proximal end, a distal end, and a plurality of magnetic elements axially aligned along a longitudinal axis of the first catheter, a second catheter comprising a proximal end, a distal end, and a plurality of magnetic elements axially aligned along a longitudinal axis of the second catheter. In some embodiments, the magnetic elements of the first catheter and the magnetic elements of the second catheter are configured to align the first catheter and the second catheter when the first catheter and second catheter are placed within first and second body lumens.

In some configurations, the second catheter comprises the same number of magnetic elements as the first catheter.

In some configurations, the second catheter comprises a different number of magnetic elements as the first catheter.

In some configurations, the first catheter and the second catheter each comprise between 2 and 15 magnetic elements.

In some configurations, each of the plurality of magnetic elements of the first catheter and the second catheter directly contact each other.

In some configurations, each of the plurality of magnetic elements of the first catheter and the second catheter are spaced longitudinally apart from each other.

In some configurations, each of the plurality of magnetic elements of the first catheter are spaced longitudinally apart from each other by a distance of about 0.5 cm or less.

In some configurations, each of the plurality of magnetic elements of the first catheter are spaced longitudinally apart from each other by non-magnetic spacers.

In some configurations, the non-magnetic spacers comprise a flexible material.

In some configurations, each of the plurality of magnetic elements comprises an axial length that is greater than or equal to an axial length of each of the non-magnetic spacers.

In some configurations, each of the plurality of magnetic elements comprises an axial length that is greater than an axial length of each of the non-magnetic spacers.

In some configurations, the flexible material comprises a polymer.

In some configurations, the first catheter and second catheter are configured to be steerable and curvable.

In some configurations, the first catheter and second catheter each comprise pullwires operably connected proximally to a control.

In some configurations, the magnetic elements of the first catheter and the second catheter comprise electromagnets.

In some configurations, the magnetic elements of the first catheter and the second catheter comprise permanent magnets.

In some configurations, the magnetic elements of the first catheter and the second catheter have a magnetic flux density of between about 3,000 and 10,000 Gauss measured at a point on the surface of one of the magnetic elements.

In some configurations, the first catheter comprises a snare element configured to be housed within a lumen of the first catheter.

In some configurations, the second catheter comprises a guidewire configured to be housed within a lumen of the first catheter.

In some configurations, the first catheter and the second catheter comprise non-magnetic distal tips.

In some embodiments, disclosed herein is a catheter, comprising a proximal end, a distal end, and a plurality of magnetic elements axially aligned along a longitudinal axis of the first catheter, wherein the magnetic elements of the first catheter are configured to align with magnetic elements of a second catheter when the first catheter and second catheter are placed within first and second body lumens.

In some embodiments, disclosed herein is a method of creating an access pathway between a first body lumen and a second body lumen, comprising any number of the following: positioning a first catheter in a first body lumen, the first catheter comprising a proximal end, a distal end, and a plurality of magnetic elements axially aligned along a longitudinal axis of the first catheter; positioning a second catheter in a second body lumen, the second catheter comprising a proximal end, a distal end, and a plurality of magnetic elements axially aligned along a longitudinal axis of the second catheter; aligning the first catheter and the second catheter at least in part via the plurality of magnetic elements of the first catheter and the second catheter; positioning a capture element in the second body lumen by moving the capture element distally out of a lumen of the second catheter; positioning a wire in the first body lumen by moving the wire out of a lumen of the first catheter; creating an access pathway between the first body lumen and the second body lumen; advancing the wire through the access pathway and into the second body lumen; coupling a portion of the wire to the capture element; withdrawing the second catheter within the second body lumen, thereby increasing a length of the wire present within the second body lumen; and releasing the wire from the capture element, thereby maintaining the wire within the second body lumen and the first body lumen, and spanning the access pathway.

In some configurations, the method also includes advancing a sheath over the wire through the first body lumen, across the access pathway, and into the second body lumen.

In some configurations, a medical device is operably coupled to the sheath.

In some configurations, the medical device comprises a replacement heart valve.

In some configurations, the medical device comprises a ventricular assist device.

In some configurations, the first body lumen is the inferior vena cava, and the second body lumen is the aorta.

In some configurations, the first body lumen is the superior vena cava, and the second body lumen is the aorta.

In some configurations, the first body lumen is a first cardiac chamber, and the second body lumen is a second cardiac chamber.

In some configurations, the first body lumen is a vein, and the second body lumen is an artery.

In some configurations, the first body lumen is an artery, and the second body lumen is a vein.

In some configurations, the first body lumen is a vascular lumen, and the second body lumen is a non-vascular lumen.

In some configurations, the first body lumen is a non-vascular lumen, and the second body lumen is a non-vascular lumen.

In some configurations, the second catheter comprises the same number of magnetic elements as the first catheter.

In some configurations, the second catheter comprises a different number of magnetic elements as the first catheter.

In some configurations, the first catheter and the second catheter each comprise between 2 and 15 magnetic elements.

In some configurations, each of the plurality of magnetic elements of the first catheter and the second catheter directly contact each other.

In some configurations, each of the plurality of magnetic elements of the first catheter and the second catheter are spaced longitudinally apart from each other.

In some configurations, each of the plurality of magnetic elements of the first catheter are spaced longitudinally apart from each other by a distance of about 0.5 cm or less.

In some configurations, each of the plurality of magnetic elements of the first catheter are spaced longitudinally apart from each other by non-magnetic spacers.

In some configurations, the non-magnetic spacers comprise a flexible material.

In some configurations, the flexible material comprises a polymer.

In some configurations, each of the plurality of magnetic elements comprises an axial length that is greater than or equal to an axial length of each of the non-magnetic spacers.

In some configurations, each of the plurality of magnetic elements comprises an axial length that is greater than an axial length of each of the non-magnetic spacers.

In some configurations, the method also includes deflecting at least one of the first catheter and the second catheter.

In some embodiments, disclosed herein is a catheter system, comprising: a first catheter comprising a proximal end, a distal end, and a plurality of magnetic elements axially aligned along a longitudinal axis of the first catheter, and a second catheter comprising a proximal end, a distal end, and a plurality of magnetic elements axially aligned along a longitudinal axis of the second catheter. In some embodiments, the magnetic elements of the first catheter and the magnetic elements of the second catheter are configured to align the first catheter and the second catheter when the first catheter and second catheter are placed within first and second body lumens. In some embodiments, each of the plurality of magnetic elements of the first catheter and the second catheter are spaced longitudinally apart from each other by non-magnetic spacers. In some embodiments, the non-magnetic spacers are permanently fixed in between adjacent magnetic elements of the plurality of magnetic elements when the first catheter is in a deployed configuration. In other words, the non-magnetic spacers are not movable to allow the magnets to directly contact each other in some embodiments. In some embodiments, the non-magnetic spacers do not include any elongate member, e.g., an elongate cord member extending therethrough, and/or any apertures through the magnetic spacers.

In some configurations, the non-magnetic spacers comprise a flexible material.

In some configurations, the second catheter comprises the same number of magnetic elements as the first catheter.

In some configurations, the second catheter comprises a different number of magnetic elements as the first catheter.

In some configurations, the first catheter and the second catheter each comprise between 2 and 15 magnetic elements.

In some configurations, each of the plurality of magnetic elements of the first catheter are spaced longitudinally apart from each other by a distance of about 0.5 cm or less.

In some configurations, each of the plurality of magnetic elements comprises an axial length that is greater than or equal to an axial length of each of the non-magnetic spacers.

In some configurations, each of the plurality of magnetic elements comprises an axial length that is greater than an axial length of each of the non-magnetic spacers.

In some configurations, the flexible material comprises a polymer.

In some embodiments, disclosed herein is a catheter system, comprising: a first catheter comprising a proximal end, a distal end, and a plurality of magnetic elements axially aligned along a longitudinal axis of the first catheter, and a second catheter comprising a proximal end, a distal end, and a plurality of magnetic elements axially aligned along a longitudinal axis of the second catheter. In some embodiments, the magnetic elements of the first catheter and the magnetic elements of the second catheter are configured to align the first catheter and the second catheter when the first catheter and second catheter are placed within first and second body lumens. In some embodiments, each of the plurality of magnetic elements of the first catheter and the second catheter are spaced longitudinally apart from each other by non-magnetic spacers. In some embodiments, the non-magnetic spacers are permanently fixed in between adjacent magnetic elements of the plurality of magnetic elements when the first catheter is in a deployed configuration.

In some configurations, the first catheter and second catheter are configured to be steerable and curvable.

In some configurations, the first catheter and second catheter each comprise pullwires operably connected proximally to a control.

In some configurations, the magnetic elements of the first catheter and the second catheter comprise electromagnets.

In some configurations, the magnetic elements of the first catheter and the second catheter comprise permanent magnets.

In some configurations, the magnetic elements of the first catheter and the second catheter have a magnetic flux density of between about 3,000 and 10,000 Gauss measured at a point on the surface of one of the magnetic elements.

In some configurations, the first catheter comprises a snare element configured to be housed within a lumen of the first catheter.

In some configurations, the second catheter comprises a guidewire configured to be housed within a lumen of the first catheter.

In some configurations, the first catheter and the second catheter comprise non-magnetic distal tips.

In some embodiments, disclosed herein is a catheter, comprising: a proximal end, a distal end, and a plurality of magnetic elements axially aligned along a longitudinal axis of the catheter. In some embodiments, each of the plurality of magnetic elements are spaced longitudinally apart from each other by non-magnetic flexible spacers. In some embodiments, the non-magnetic flexible spacers are permanently fixed in between adjacent magnetic elements of the plurality of magnetic elements when the catheter is in a deployed configuration.

In some configurations, disclosed is a catheter or catheter system comprising, consisting essentially of, or consisting of any number of features described in this disclosure.

In some configurations, disclosed is a method of using a catheter or catheter system comprising, consisting essentially of, or consisting of any number of features described in this disclosure.

DETAILED DESCRIPTION

In order to cross the venous access side to the arterial (e.g., aortic) access side there is a need to make accessing simpler and more accessible to the vast majority of the implanter market in order for broad adoption of transcaval access. There is also a need to approximate two body lumens, such as vessels including but not limited to the aorta and IVC in order to perform this access (or other arterial and venous structures—e.g., axillary/subclavian). In some embodiments, magnets can be advantageously utilized for this and other indications, including the creation of arteriovenous fistulas, access between two venous structures; access between two arterial structures; as well as non-vascular fistulas and access procedures (e.g., gastrotomy placement). In some embodiments, systems and methods as disclosed herein can be utilized for cross-chamber punctures (e.g., from the left atrium to the aorta; across the septum (right atrium to left atrium; right ventricle to left ventricle)); across valve planes, and the like. In some embodiments, systems and methods can involve intra-cranial lumens, such as vascular lumens for a neuro-interventional procedure. In some embodiments, systems and methods can be utilized for vascular graft placement, including but not limited to thoracic endovascular aortic grafts and abdominal aortic endografts for vertical spaces.

Figure 2:
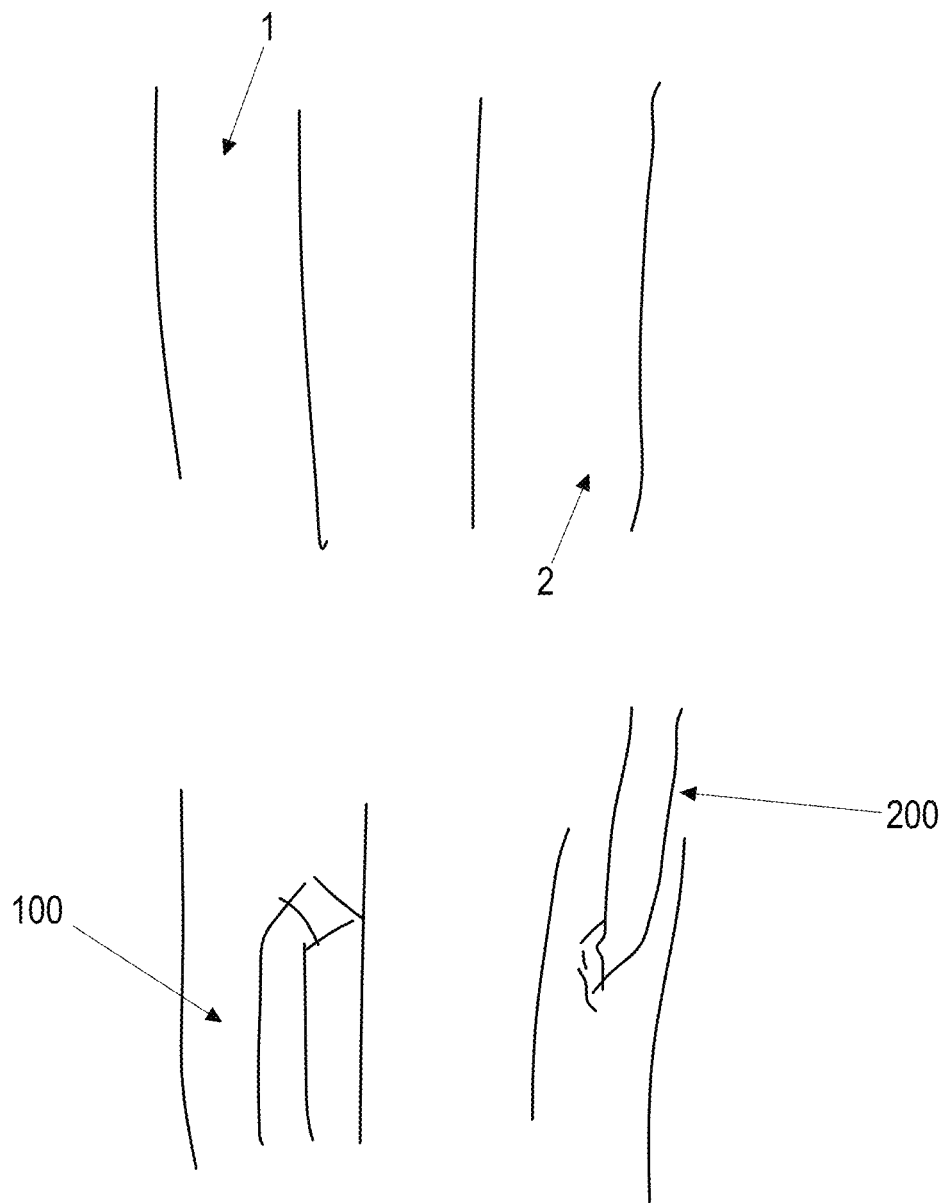
FIGS. 2-9 schematically illustrate a magnetic luminal access system and method.
Figure 3:
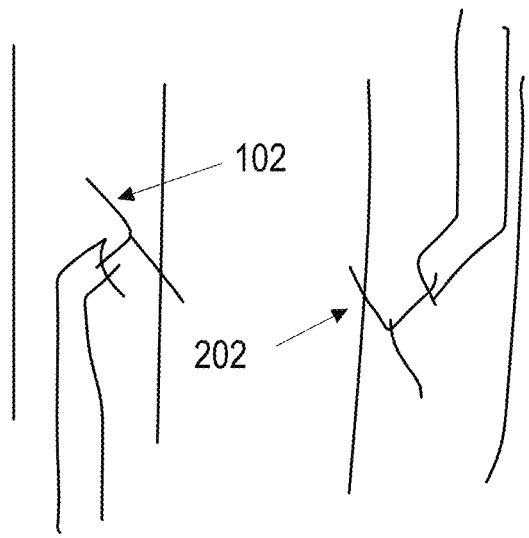
Figure 4:
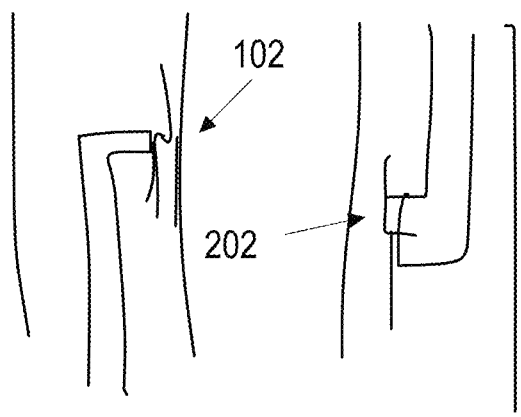
Figure 5:
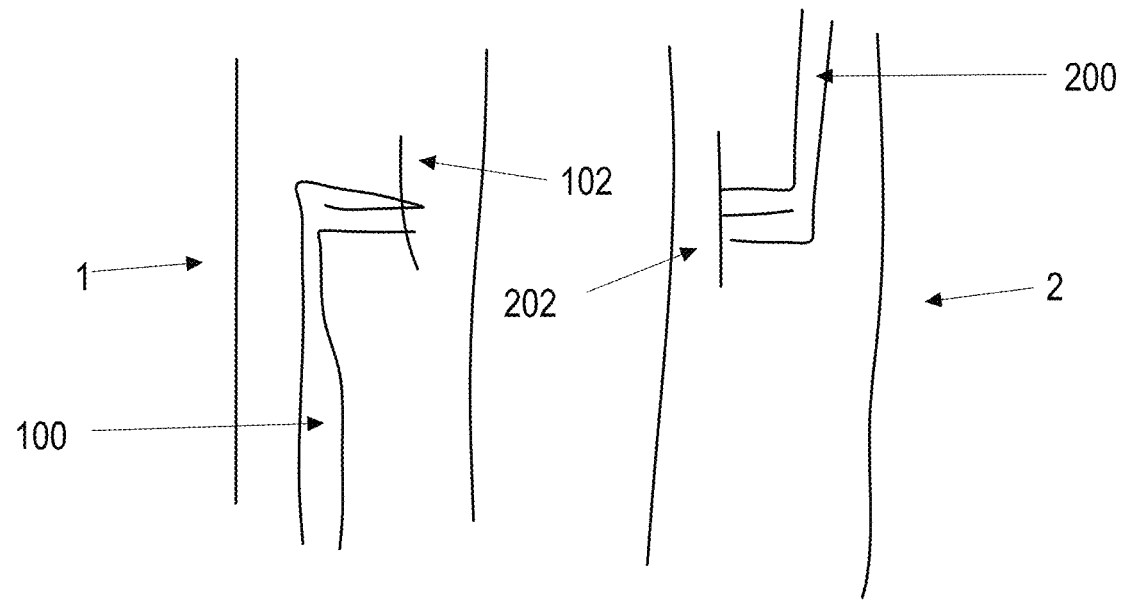
Figure 6:
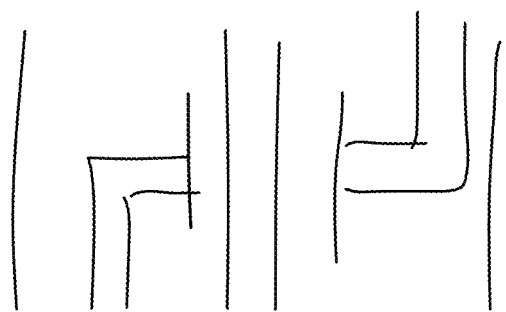
Figure 7:
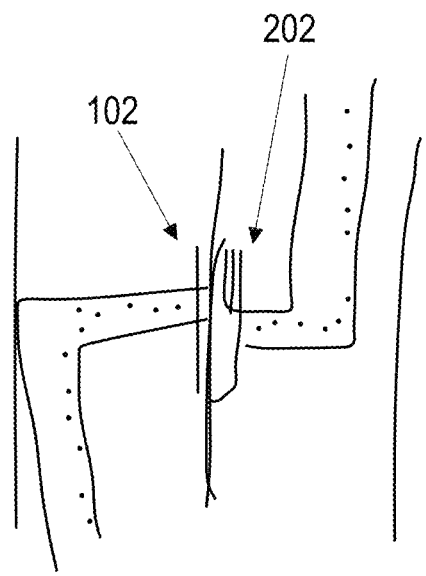
Figure 8:
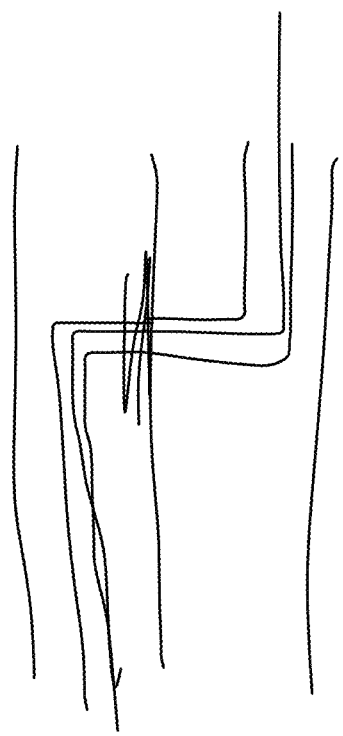
Figure 9:
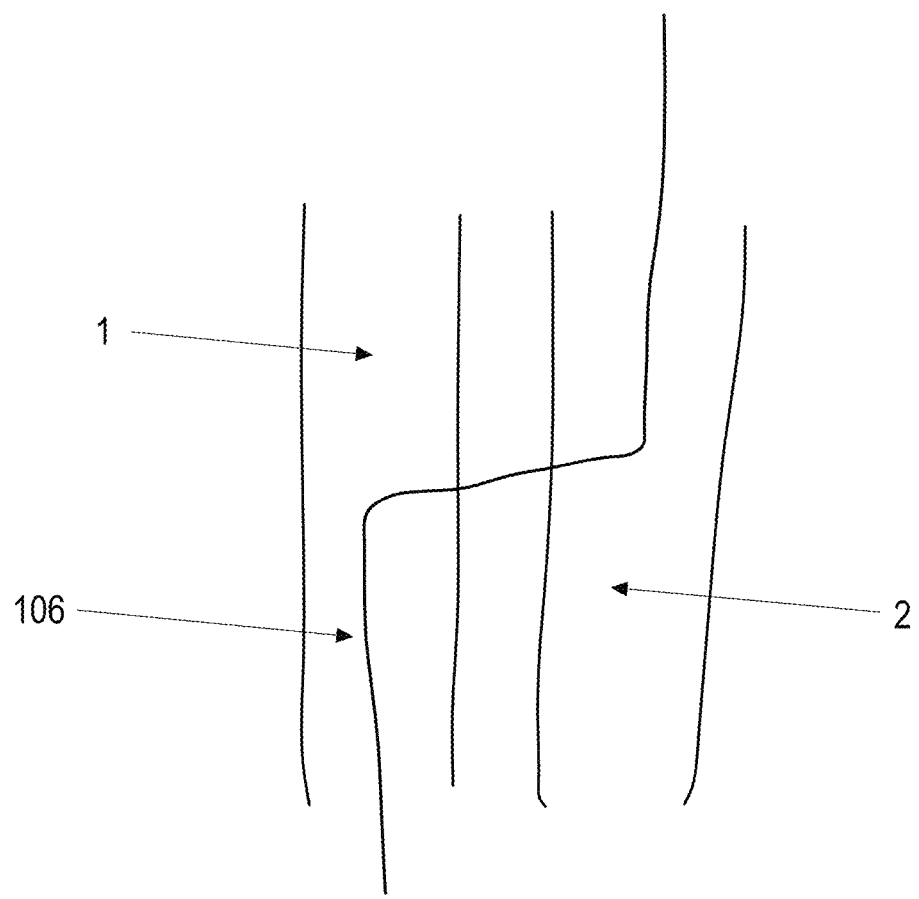
Figure 15:
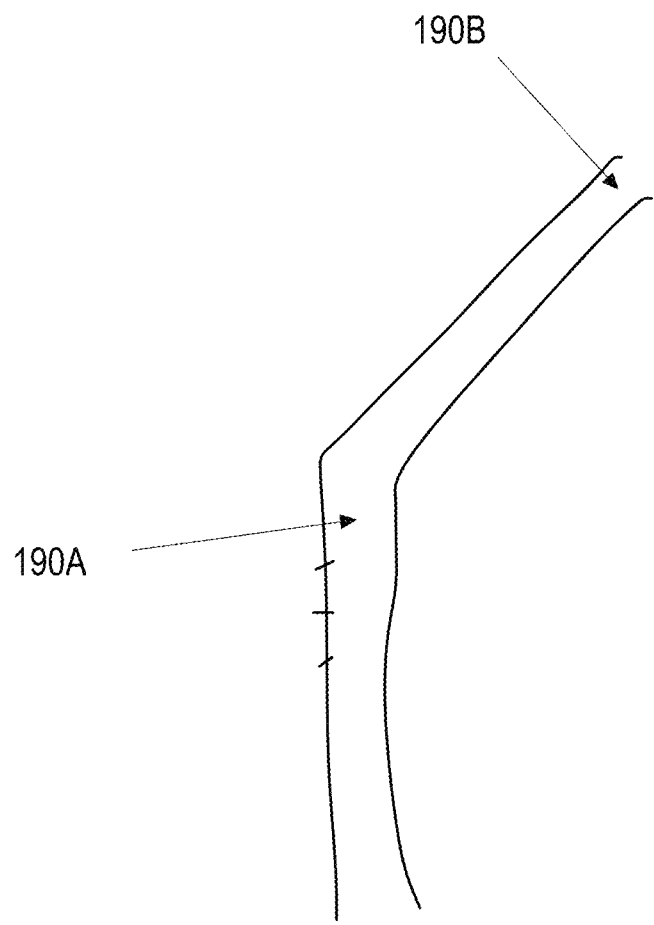

Magnets can be used to help orient device and approximate tissue. A device driven by solenoid magnets with electrical charge can be utilized in order to control magnet activation. Using a variable driving system can adjust level of magnetic attraction with charge, and the unit can be withdrawn. A first device, e.g., a first catheter 100, can be placed in a first body lumen (e.g., marked 1 in FIG. 2). A second device, e.g., a second catheter 200, can be placed in a second body lumen (e.g., marked 2 in FIG. 2). The devices can be manipulated to be oriented toward each other. This can be facilitated under imaging, such as fluoroscopy, CT, MRI, or ultrasound, as some non-limiting examples. Complementary magnetic elements 102, 202 can be expanded out of the distal end of the catheter, as shown in FIG. 3, and oriented against the wall of the body lumen, as shown in FIG. 4. Activation of the magnetic elements can draw the two body lumens closer together until their walls contact each other, as shown in FIGS. 5-7. Once the devices are approximated as shown in FIGS. 8-9, a guidewire 106, such as a sharp non-ferromagnetic access wire for example, attached to an electrocautery donor catheter with an aligning lumen can puncture the receiving catheter, and be withdrawn into the aorta or other lumen, establishing wire access; next, an over the access wire (e.g., 0.014 inch in diameter) expansion piggyback catheter can used to establish a 0.035" wire and then subsequent access for the procedure as shown schematically in FIG. 15. The catheter can taper from a first, larger cross-section 190A to a second, smaller cross-section 190B in some cases.

Some embodiments are directed to magnetic puncture access and delivery systems and methods, including creating a passageway, such as a fistula, between two vessels or segments of a vessel.

Transcatheter aortic valve replacement (TAVR) is described as a minimally invasive procedure that replaces improper functioning aortic valves. TAVR offers an efficient valve replacement procedure as compared to open-heart surgery for the benefit of high risk patients with more rapid recovery and minimal co-morbidity. TAVR is used for the treatment of aortic valve disorders such as severe aortic stenosis, degeneration, & regurgitation. Transcatheter aortic valve replacement devices are integrated with valve frame (made of nitinol or stainless steel), valve leaflets material (made of bovine or cow heart tissue). These aortic valves are available with varied sizes (such as, for example, 14 mm, 16 mm, 18 mm, 20 mm, 22 mm, & 29 mm). TAVR requires large bore access due to sizing restrictions on the crimped valve.

TAVR is performed during different access methods such as transfemoral implantation (through the femoral artery), transapical implantation (through the apex of the heart), transaortic implantation (through the top of right chest), and transcaval implantation (through the femoral vein).

Notable healthcare developments can focus on chronic care patients, centering on patient ambulation and mobilization, as well as new technologies. There is also a focus on native heart recovery and remodeling with intent to explant as a cost-effective strategy that promotes quality of life.

There are several medical devices utilized for temporary ventricular support in patients with decreased heart function, including the IMPELLA pump system by Abiomed, Inc. (Danvers, Mass.). Impella has an Expandable Cardiac Power or "ECP" pump designed for blood flow of >3 liters/minute. It is intended to be delivered on the standard Impella 9 Fr catheter and can include an 18 Fr expandable inflow in the left ventricle only with a smooth, clear, polyurethane membrane crossing the left ventricle. An enhanced Impella CP pump is designed to have an increased flow of 4.5 liters/minute with improved inflow design and smart sensor technology. It can be delivered on the standard Impella 9 Fr catheter and 14 Fr pump and is designed to provide support for up to 10 days. Another system is the "Impella 5.5," a pump designed for flow of 5.5 liters per minute. It can be delivered on the standard 9 Fr catheter and includes a 19 Fr pump that is 45% shorter than the current Impella 5.0. This pump is designed for duration of weeks to months. Furthermore, another system includes the Impella Bridge to Recovery or "BTR": The Impella BTR is designed with similar specifications to the Impella 5.5 and is being developed with the intention of permitting patients to be discharged from the hospital with a wearable driver. It is designed to provide support for months to years.

Figure 1:
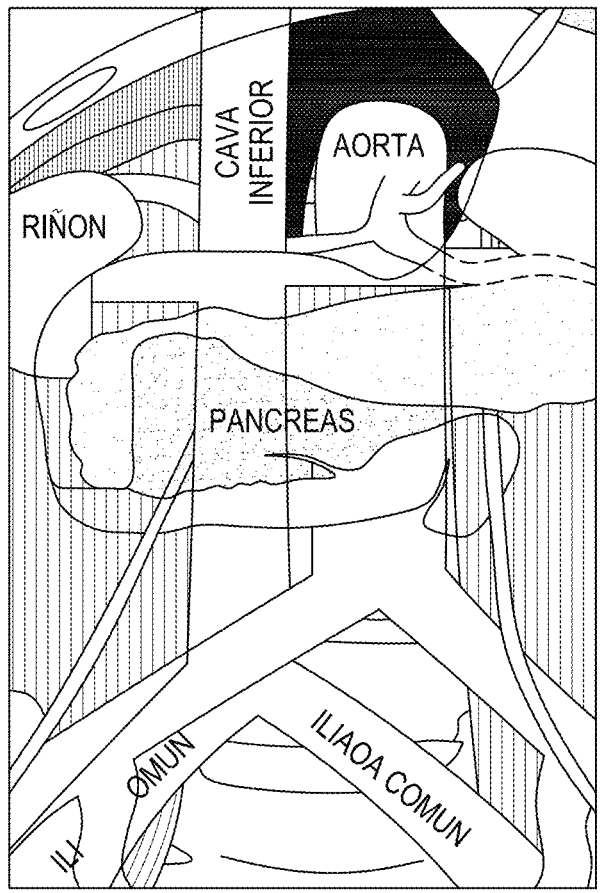
FIG. 1 schematically illustrates anatomy including the inferior vena cava, the aorta, and the overlying pancreas.

TAVR/IMPELLA and emerging hemodynamic support devices currently require large bore access (14-19 French sheath system). Large bore arterial access (generally required for insertion) cannot be obtained in up to 25% of patients. When large bore arterial access is successfully obtained, risks of limb ischemia currently limit the technical applicability of current hardware. Venous access can be safer in some cases due to low pressure circulation and controllability. However, access from venous side to arterial side has tremendous challenges, and is generally only available in highly specialized centers due to complexity of access. There is a current need for a multitude of specialty equipment in order to traverse the virtual space from the inferior vena cava (IVC) to the aorta. Due to the distance between the IVC and aorta, often this distance cannot be traversed safely. FIG. 1 schematically illustrates anatomy including the inferior vena cava, the aorta, and the overlying pancreas. At the completion of procedure, a separate closure device can be required that can be challenging.

In order to cross the venous access side to the arterial (e.g., aortic) access side there is a need to make accessing simpler and more accessible to the vast majority of the implanter market in order for broad adoption of transcaval access. There is also a need to approximate two body lumens, such as vessels including but not limited to the aorta and IVC in order to perform this access (or other arterial and venous structures—e.g., axillary/subclavian). In some embodiments, magnets can be advantageously utilized for this and other indications, including the creation of arteriovenous fistulas, access between two venous structures; access between two arterial structures; as well as non-vascular fistulas and access procedures (e.g., gastrostomy placement). In some embodiments, systems and methods as disclosed herein can be utilized for cross-chamber punctures (e.g., from the left atrium to the aorta; across the septum (right atrium to left atrium; right ventricle to left ventricle)); across valve planes, and the like.

Magnets can be used to help orient device and approximate tissue. A device driven by solenoid magnets with electrical charge can be utilized in order to control magnet activation. Using a variable driving system can adjust level of magnetic attraction with charge, and the unit can be withdrawn. A first device, e.g., a first catheter 100, can be placed in a first body lumen (e.g., marked 1 in FIG. 2). A second device, e.g., a second catheter 200, can be placed in a second body lumen (e.g., marked 2 in FIG. 2). The devices can be manipulated to be oriented toward each other. This can be facilitated under imaging, such as fluoroscopy, CT, MRI, or ultrasound, as some non-limiting examples. Complementary magnetic elements 102, 202 can be expanded out of the distal end of the catheter, as shown in FIG. 3, and oriented against the wall of the body lumen, as shown in FIG. 4. Activation of the magnetic elements can draw the two body lumens closer together until their walls contact each other, as shown in FIGS. 5-7. Once the devices are approximated as shown in FIGS. 8-9, a guidewire 106, such as a sharp non-ferromagnetic access wire for example, attached to an electrocautery donor catheter with an aligning lumen can puncture the receiving catheter, and be withdrawn into the aorta or other lumen, establishing wire access; next, an over the access wire (e.g., 0.014 inch in diameter) expansion piggyback catheter can used to establish a 0.035" wire and then subsequent access for the procedure as shown schematically in FIG. 15. The catheter can taper from a first, larger cross-section 190A to a second, smaller cross-section 190B in some cases.

In some embodiments, one or both of the first device and the second device can each include a plurality of magnetic elements directly connected and/or spaced apart along the catheter (e.g., spaced apart along a longitudinal axis of the catheter, spaced apart helically along the catheter, etc.). The magnetic elements can be attached to, embedded within, or otherwise connected to the catheter. In some embodiments, the magnetic elements form part of the radial outer-most surface or layer of the catheter. In some embodiments, the magnetic elements are not the outer-most surface or layer of the catheter, and can have a biocompatible plastic, polymer, or other material overlying the magnetic element.

In some embodiments, the first device and the second device can both include about, at least about, or no more than about 2, 3, 4, 5, 6, 7, 8, 9, 10, 11, 12, 13, 14, 15, 16, 17, 18, 19, 20, or more or less magnetic elements, or ranges including any two of the foregoing values. Not to be limited by theory, a catheter system including a plurality of spaced-apart magnetic elements on each of a first device and a second device can advantageously allow for the ability to more easily align and position both catheters at the desired location compared with devices that include only a single magnet. Furthermore, in some cases, utilizing a plurality of magnets allows for the magnetic strength of the plurality of magnets to be spread over each of the plurality of magnets, compared to a single magnet localization system of each catheter. Moreover, in some case, utilizing a plurality of magnets does not necessarily require perfect alignment of an individual magnetic element of a first catheter to a corresponding individual magnetic element of a second catheter.

In some embodiments, the plurality of magnetic elements on the first device and/or the second device can all be present along the distal-most 50%, 40%, 30%, 20%, 10%, or less of each device (e.g., catheter).

In some embodiments, the first device and the second device each have the same number of magnetic elements. In some embodiments, the first device and the second device do each not have the same number of magnetic elements.

Figure 9A:
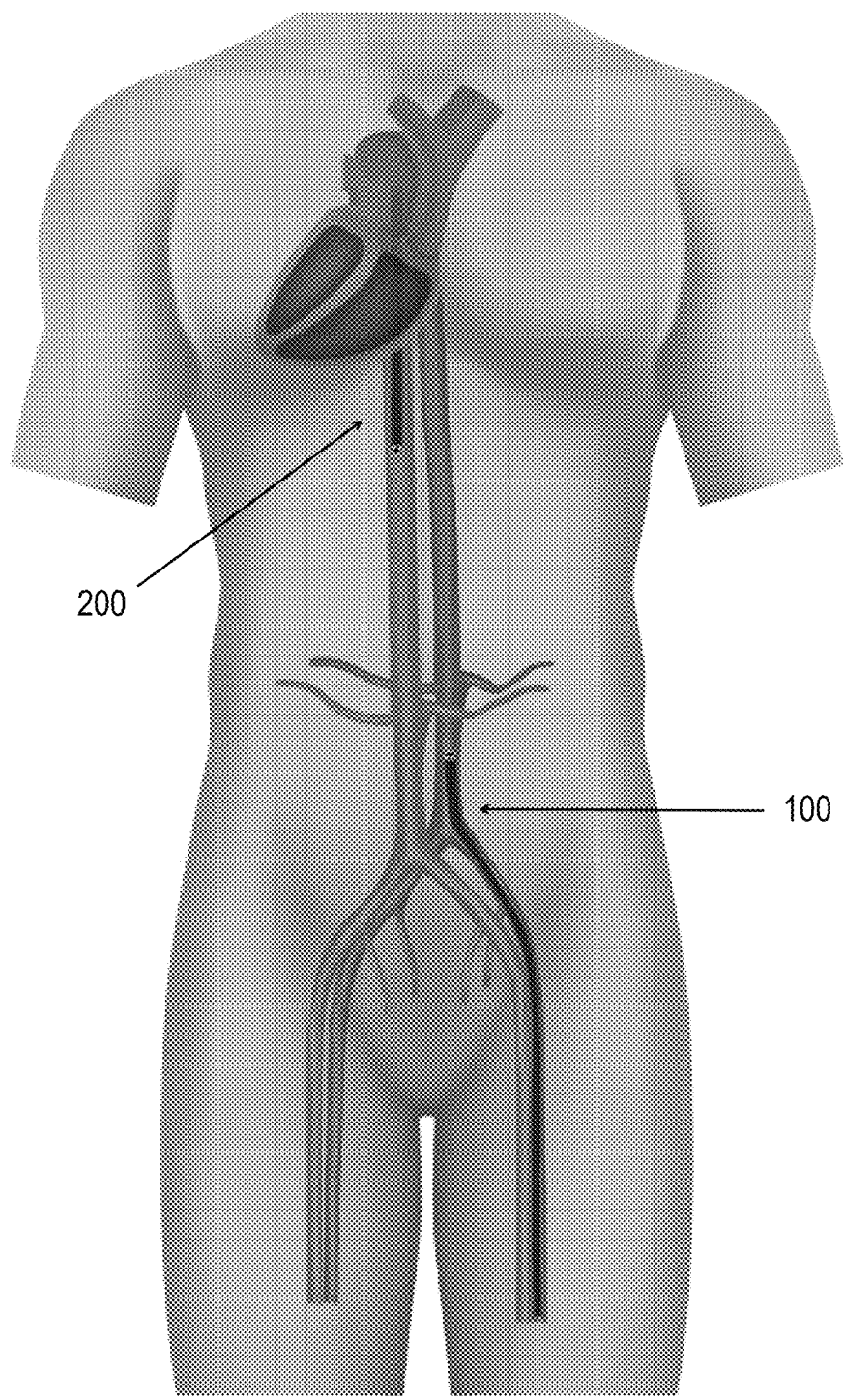
FIGS. 9A-9C schematically illustrate another embodiment of positioning a dual catheter system for creating an access pathway from a first body lumen to a second body lumen.
Figure 9B:
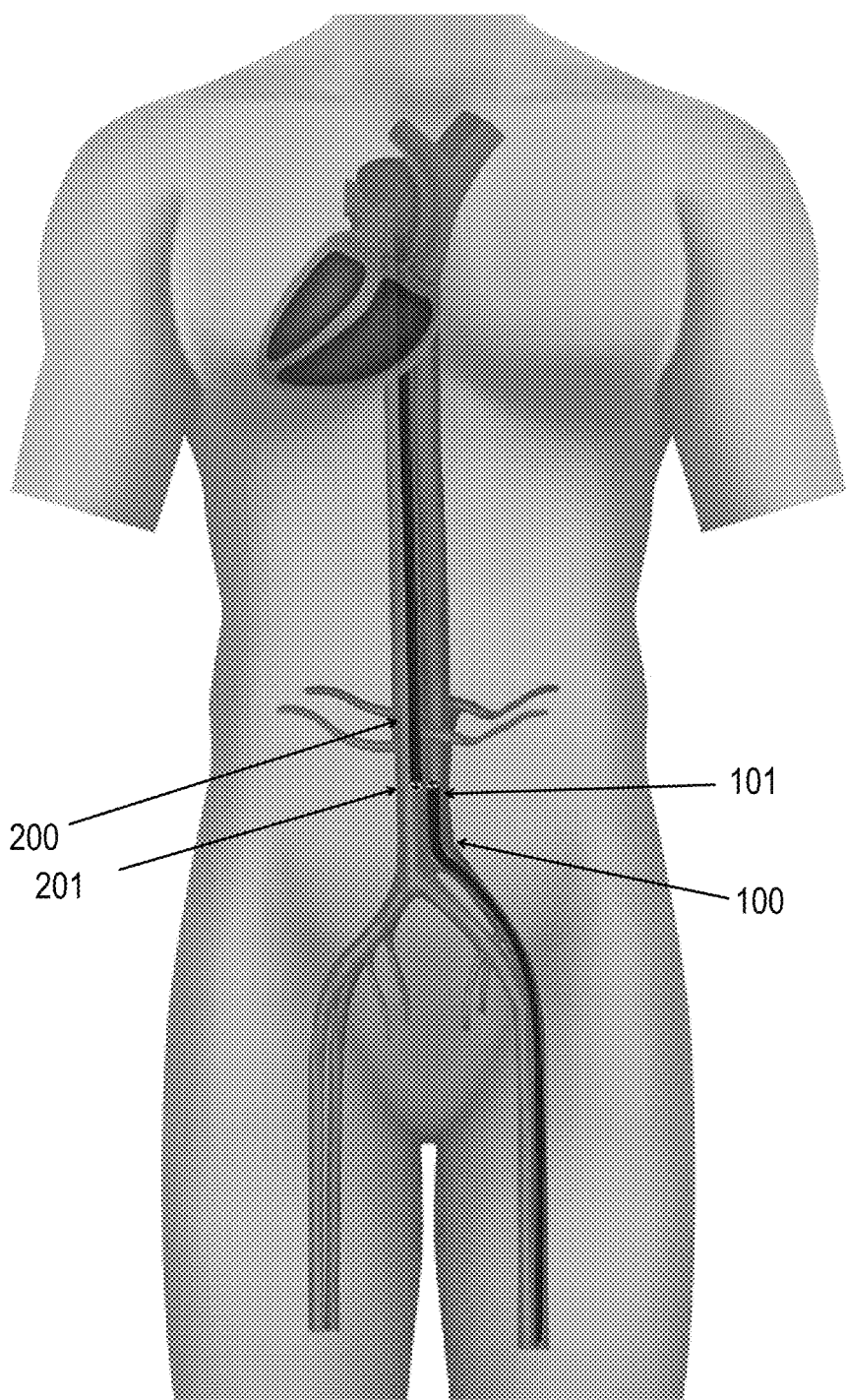
Figure 9C:
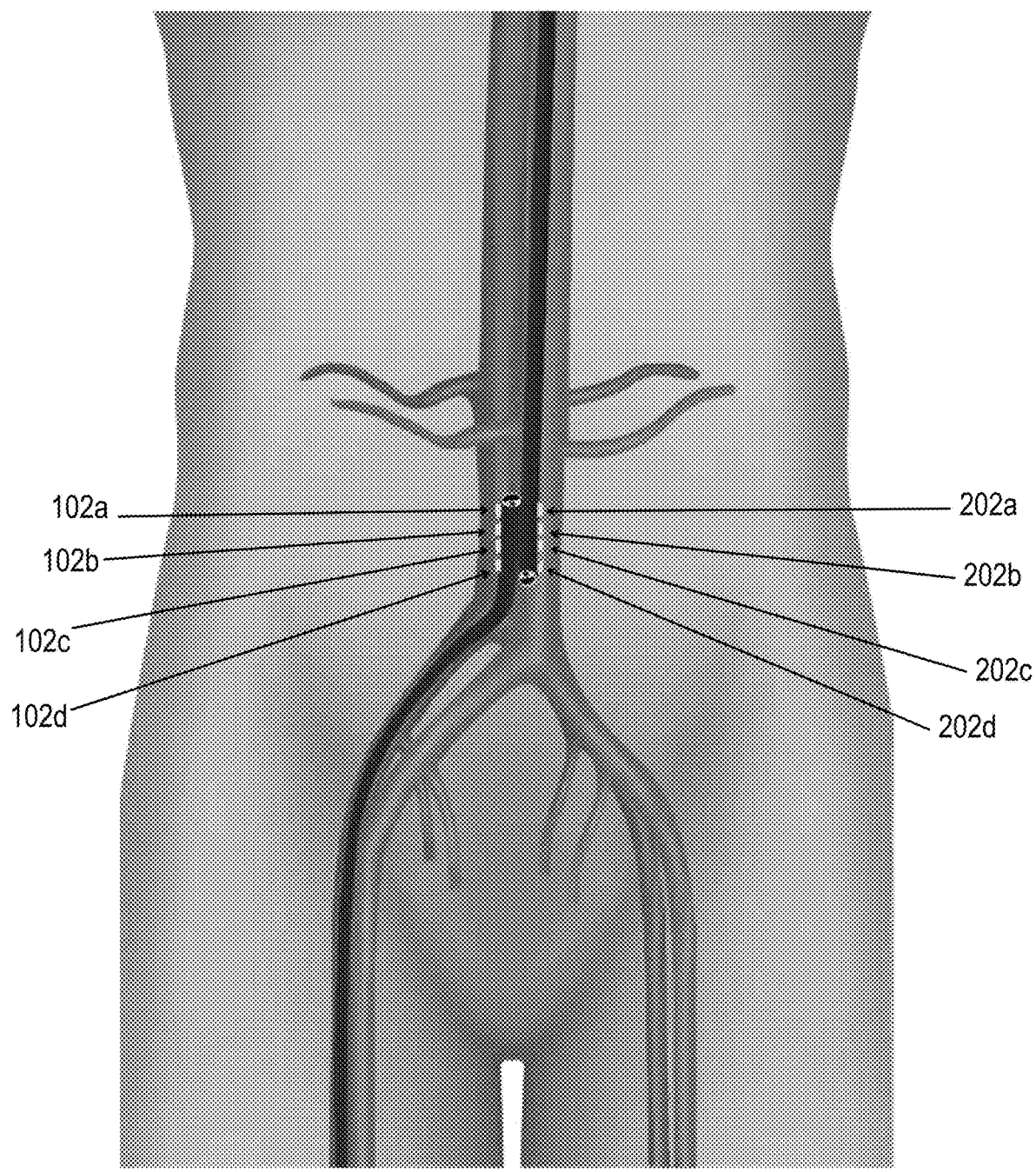

FIGS. 9A-9C schematically illustrate another embodiment of positioning a dual catheter system for creating an access pathway from a first body lumen to a second body lumen. As shown in FIG. 9A, a first catheter 100 can be inserted into a first body lumen (e.g., percutaneously or via a cut-down approach, for example), such as the femoral vein in one example, and advanced cephalad into the inferior vena cava. A second catheter can be inserted into a second body lumen such as a radial, brachial, or subclavian artery for example, and advanced into the aorta as illustrated. As shown in FIG. 9B, the distal ends 101, 201 of the respective catheters 100, 200 are shown in proximity to each other. As shown in FIG. 9C, a plurality of complementary magnetic elements (102a, 102b, 102c, 102d and 202a, 202b, 202c, and 202d) spaced apart along a longitudinal axis of each catheter are aligned with each other to facilitate creation of an access pathway as described elsewhere herein.

Figure 9D:
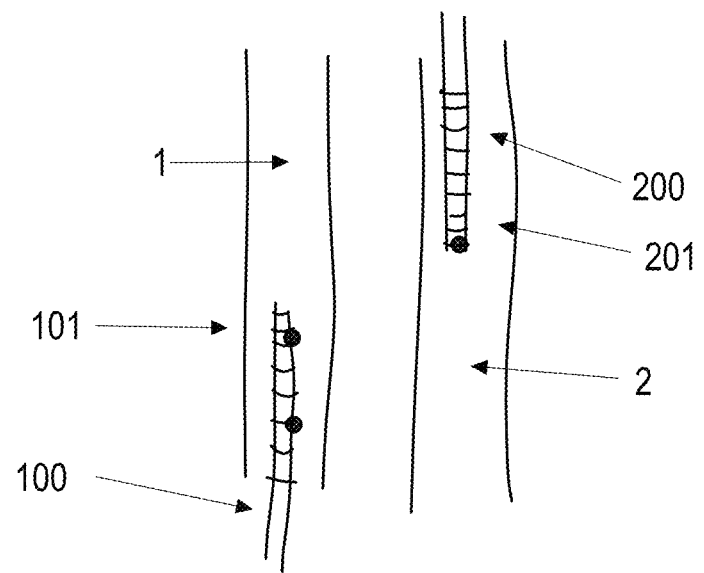
FIGS. 9D-9M schematically illustrate another embodiment of positioning a dual catheter system for creating an access pathway from a first body lumen to a second body lumen.
Figure 9E:
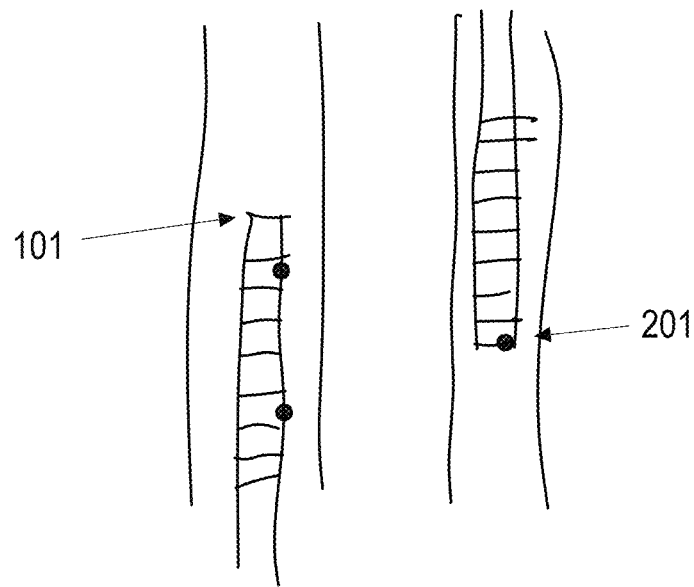
Figure 9F:
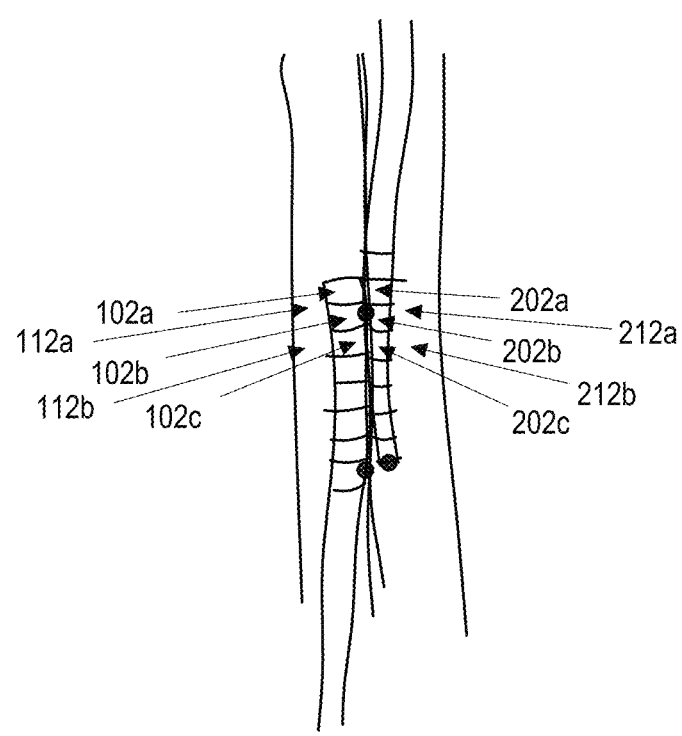
Figure 9G:
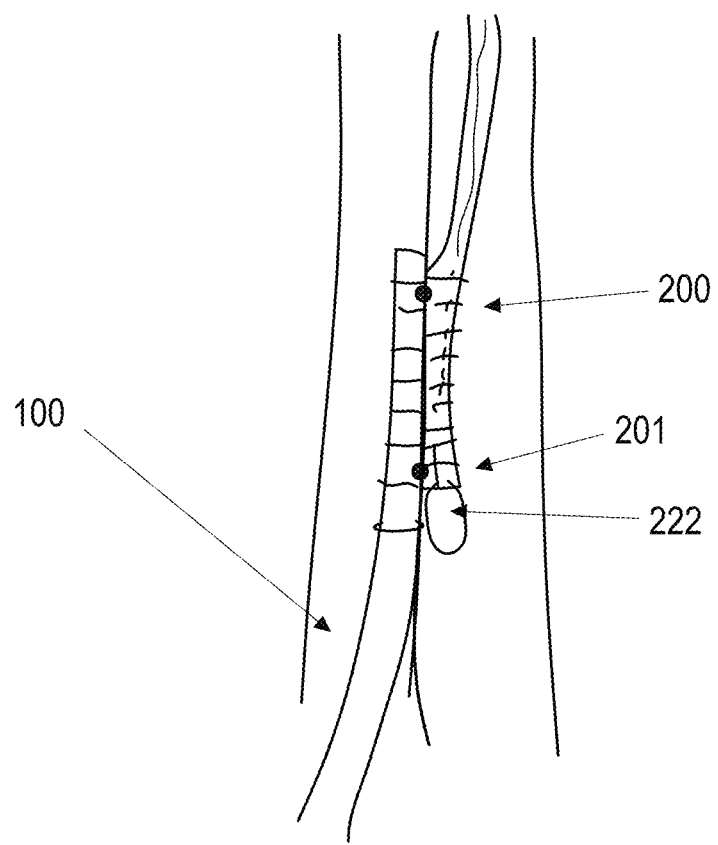
Figure 9H:
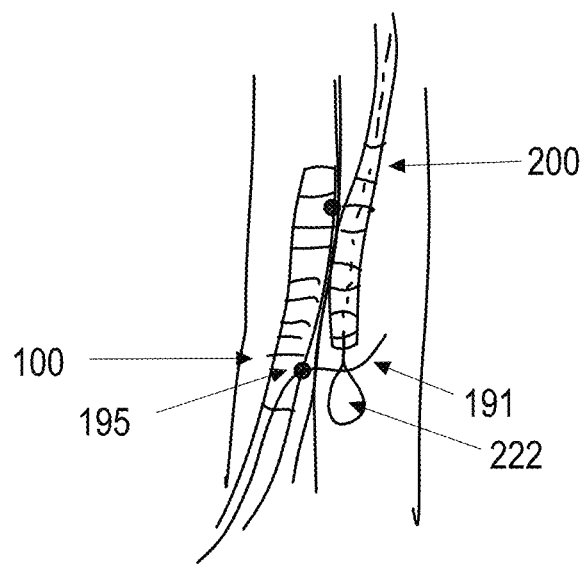
Figure 9I:
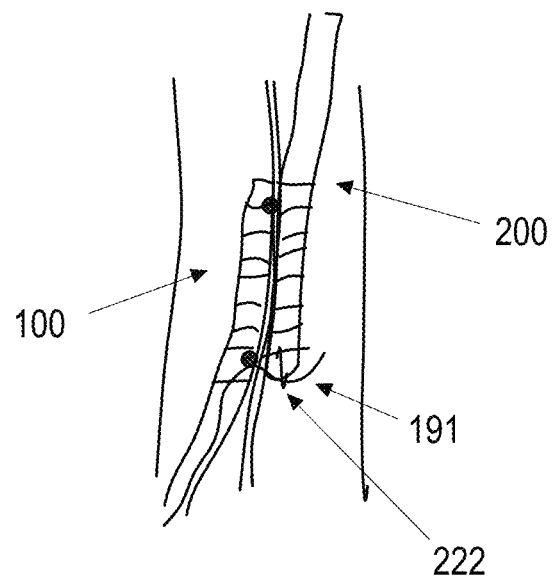
Figure 9J:
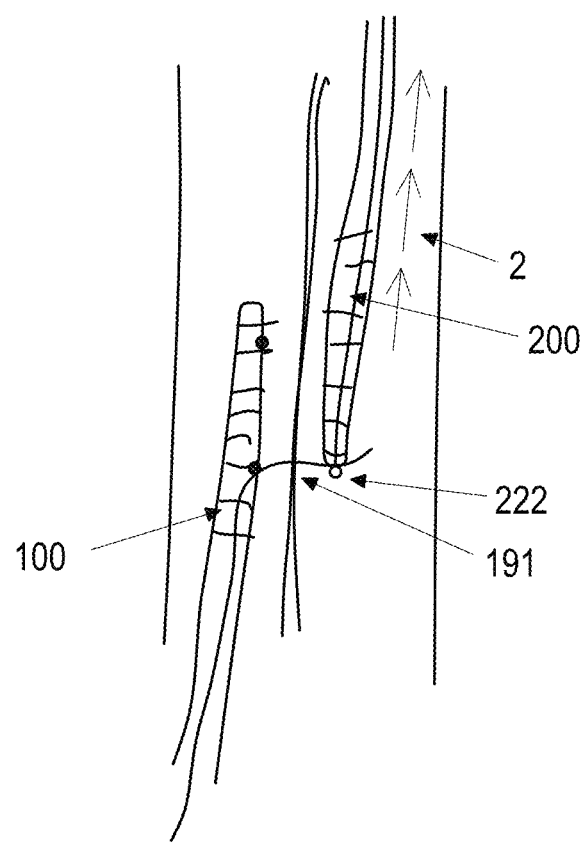
Figure 9K:
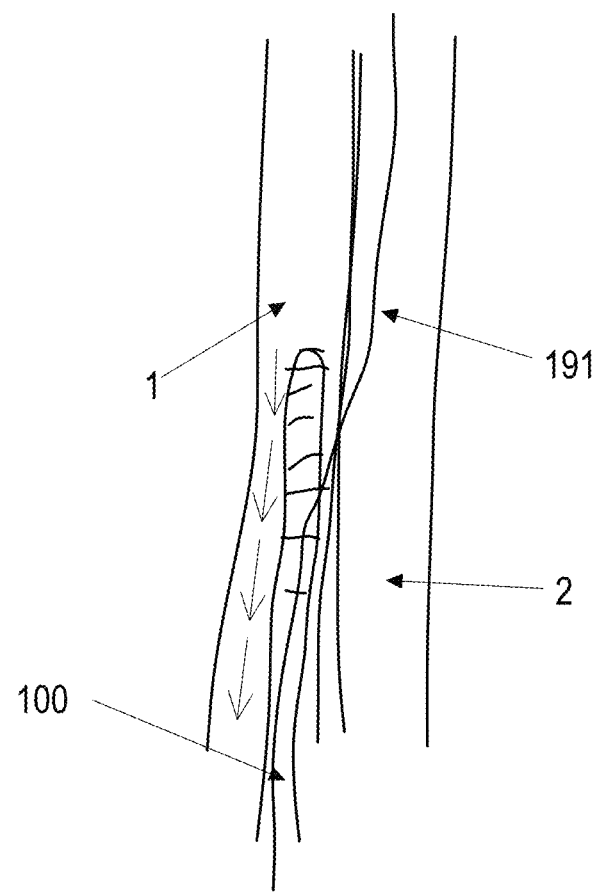
Figure 9L:
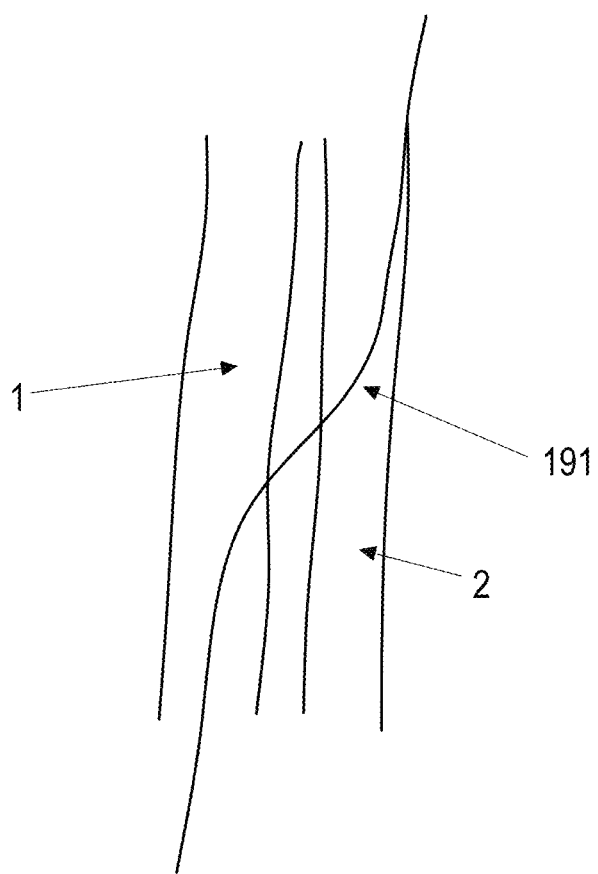
Figure 9M:
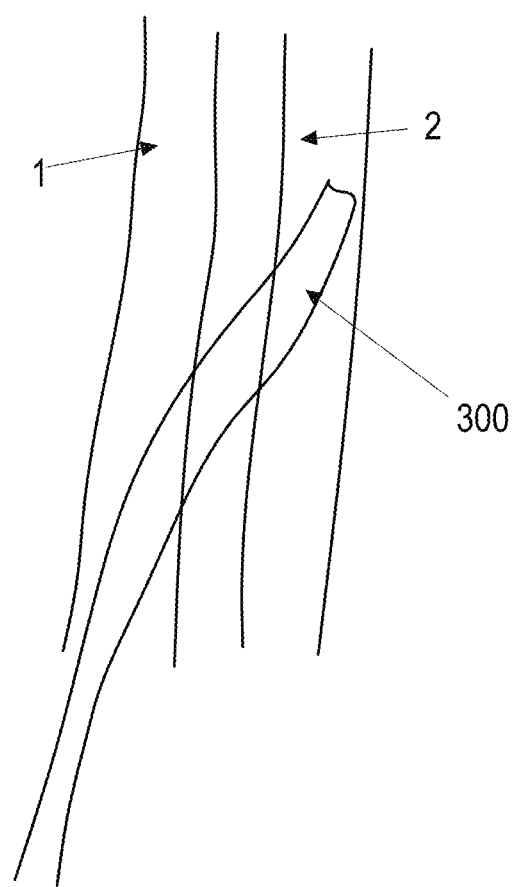

FIGS. 9D-9M schematically illustrate another embodiment of positioning a dual catheter system for creating an access pathway from a first body lumen to a second body lumen. As shown in FIG. 9D, a first catheter 100 can be inserted into a first body lumen 1 and advanced in a first direction, (e.g., cephalad) as described elsewhere herein. A second catheter 200 can be inserted into a second body lumen 2 and advanced in a second direction (e.g., caudal) opposite the first direction, as illustrated. As shown in FIG. 9E, the distal end 101 of the first catheter 100 and distal end 201 of the second catheter 200 are moved into alignment (e.g., with flexion and/or manipulation of the first catheter 100 and the second catheter 200). As shown in FIG. 9F, the tissue planes of the first and second body lumens can be approximated by attraction of magnetic elements 102a, 102b, 102c of the first catheter and complementary magnetic elements 202a, 202b, 202c of the second catheter. The magnetic elements of the first catheter 102a, 102b, 102c can be spaced apart by flexible non-magnetic elements 112a, 112b (e.g., polymeric spacers or other materials, including those as disclosed elsewhere herein). The magnetic elements of the second catheter 202a, 202b, 202c can also be spaced apart by flexible non-magnetic elements 212a, 212b. As shown in FIG. 9G, a capture element 222 such as a snare can be advanced distally out of a lumen at, for example, the distal end 201 of the second catheter 200. The capture element 222 could also be movable jaws, or the like. As shown in FIG. 9H, a puncture guidewire 191 can be advanced out of a side port 195 of the first catheter 100 and through the walls of the first lumen and the second lumen to reach the interior lumen of the second lumen. This can be accomplished, for example, using electromagnetic energy (e.g., RF, microwave, ultrasound, and the like) using an effector at the distal end of the wire or a separate device, mechanical force (e.g., a sharp/cutting tip), and other techniques. The puncture guidewire 191 can then be threaded through or otherwise coupled to the capture element, e.g., snare 222. As shown in FIG. 9I, the capture element 222 can be withdrawn proximally back into a lumen of the second catheter, capturing the guidewire 191. As shown in FIG. 9J, the first catheter 100 and second catheter 200 can be separated from each other by overcoming the force of the respective magnetic elements, and the second catheter 200 can be withdrawn within the second body lumen 2 in direction of arrows, taking with it the puncture guidewire 191 secured within the capture element 222. As shown in FIG. 9K, the first catheter 100 can then be withdrawn within the first body lumen 1, with puncture guidewire 191 still spanning the first body lumen 1 and the second body lumen 2. FIG. 9L illustrates puncture guidewire 191 still spanning the first body lumen 1 and the second body lumen 2 with both catheters withdrawn. As shown in FIG. 9M, a sheath or catheter 300 can then be advanced through first body lumen 1 and into the second body lumen 2 over the puncture guidewire 191, and an index procedure can be performed. The puncture guidewire 191 can then be withdrawn.

In some embodiments, a wire, such as a puncture guidewire, can be derived from, for example, an Astato or Confianza style 0.014", 0.018" or other size wires with a portion of the distal tip cut off in order to increase rigidity of the wire. The wire can have a constant or substantially constant rigidity throughout its entire length. In some embodiments, a distal end of the wire comprises an insulation layer/material in order to allow for easier gripping/capture of the wire and control without losing the ability to cauterize the target wall. In some embodiments, a proximal end of the wire is not insulated or coated, to allow for electrical conductivity and removable connection to a generator, such as an electric current generator or others as disclosed elsewhere herein. As such, in some embodiments, the proximal end of the wire is not insulated or coated, while the remainder of the wire can include insulation/coating. In some embodiments, the proximal end of the wire has a flattened (e.g., non-circular) cross-section to allow for clamping to a generator. The proximal end of the wire can also have a connector, such as a quick-connect plug, alligator clip, style clip, or other mechanism.

In some embodiments, a puncture guidewire can have any desired distal tip geometry, such as a straight tip, J-tip, pigtail tip, and the like.

In some embodiments, a capture member, such as, for example, a snare can be non-magnetized. In some embodiments, the entire snare, or a portion of the snare can be magnetized, such as just the snare tip, or a portion of the snare tip. In some embodiments, a puncture guidewire, such as a portion of the puncture guidewire, such as the distal tip of the puncture guidewire for example, can be magnetized to facilitate creation of the fistula between the first lumen and the second lumen. In some embodiments, at least a portion of the capture member and the puncture guidewire are magnetized; or only the capture member, or only the puncture guidewire in other embodiments.

Figure 9N:
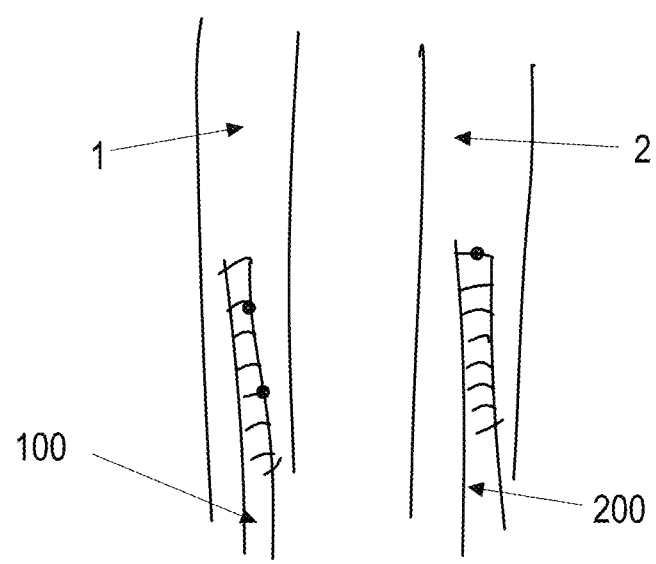
FIGS. 9N-9U schematically illustrate another embodiment of positioning a dual catheter system for creating an access pathway from a first body lumen to a second body lumen that can be somewhat similar to as shown in FIGS. 9D-9M, except both catheters can be advanced in the same direction, rather than opposite directions.
Figure 9O:
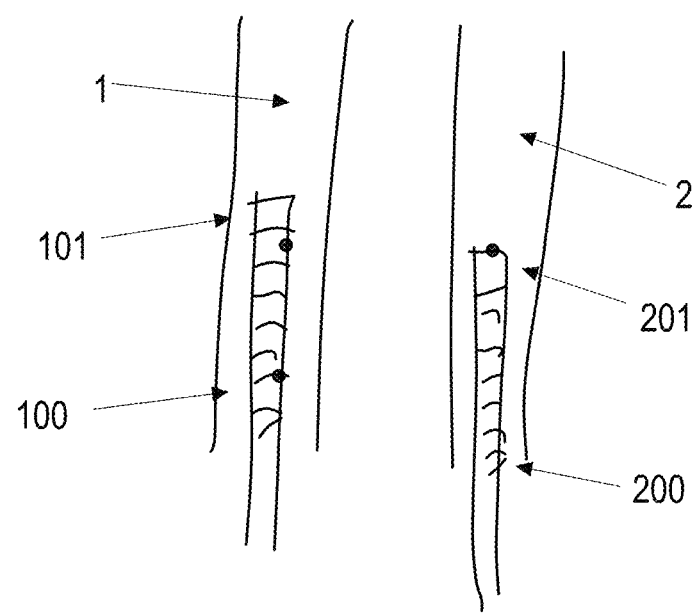
Figure 9P:
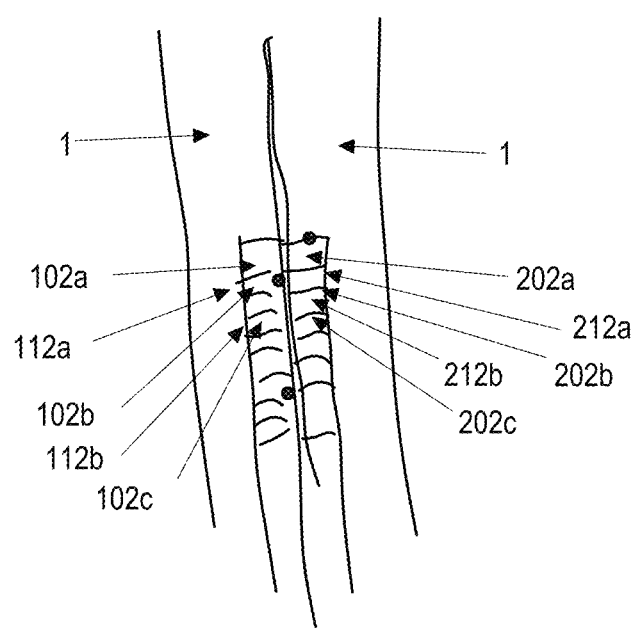
Figure 9Q:
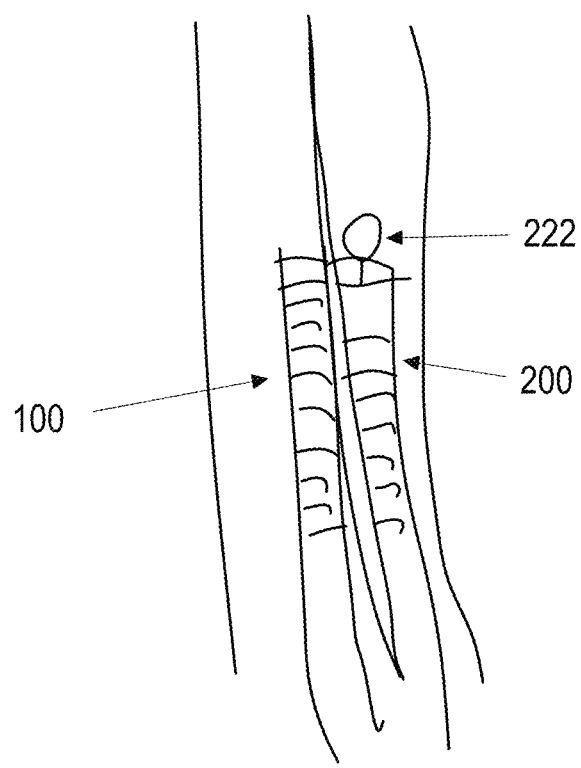
Figure 9R:
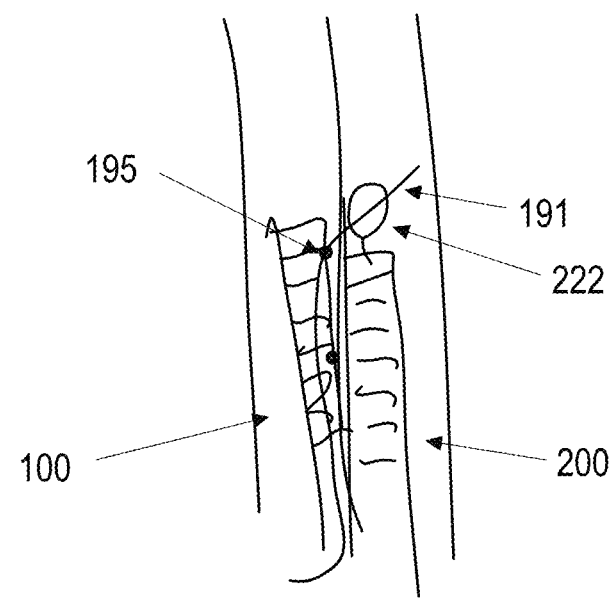
Figure 9S:
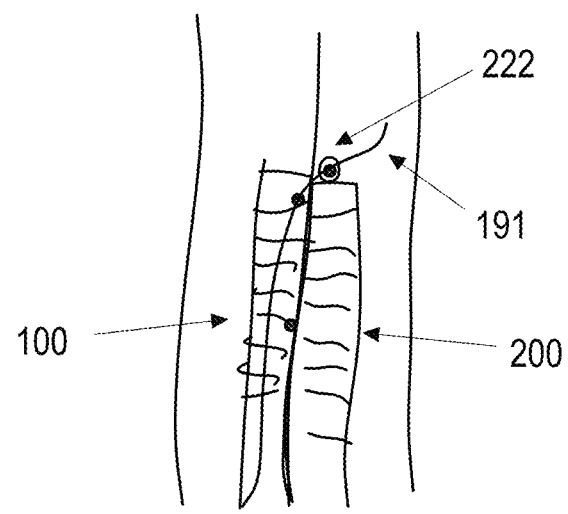
Figure 9T:
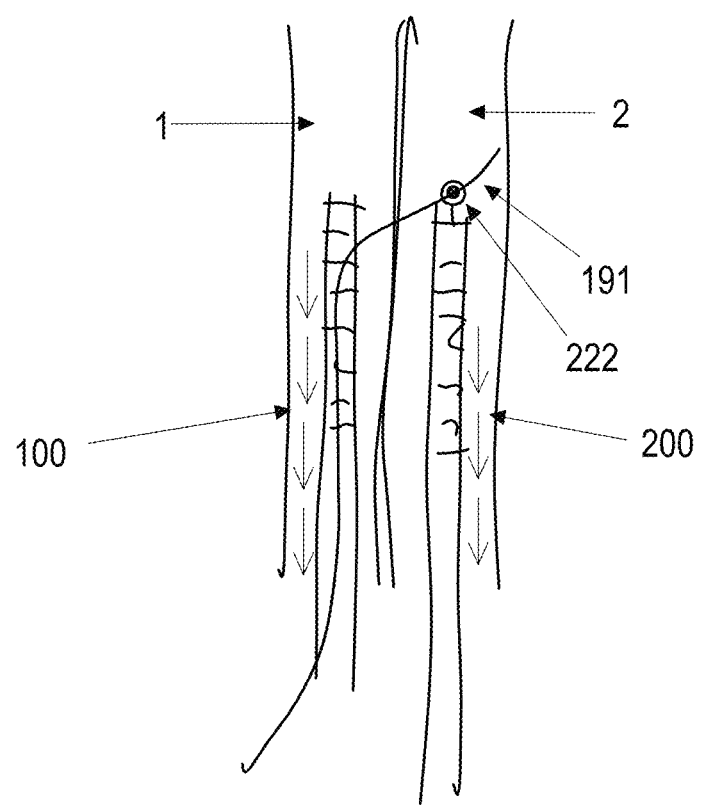
Figure 9U:
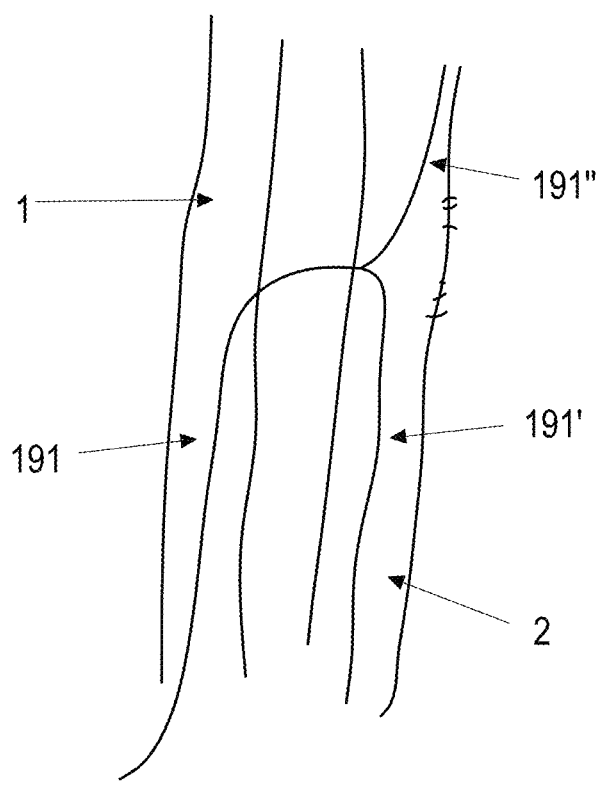

FIGS. 9N-9U schematically illustrate another embodiment of positioning a dual catheter system for creating an access pathway from a first body lumen to a second body lumen that can be somewhat similar to as shown in FIGS. 9D-9M, except both catheters can be advanced in the same direction, rather than opposite directions. As shown in FIG. 9N, a first catheter 100 can be inserted into a first body lumen 1 and advanced in a first direction, (e.g., cephalad) as described elsewhere herein. A second catheter 200 can be inserted into a second body lumen 2 and advanced in a second direction (e.g., cephalad) that is generally the same direction as the first direction, as illustrated. As shown in FIG. 9O, the distal end 101 of the first catheter 100 and distal end 201 of the second catheter 200 are moved into alignment (e.g., with flexion and/or manipulation of the first catheter 100 and the second catheter 200). As shown in FIG. 9P, the tissue planes of the first and second body lumens can be approximated by attraction of magnetic elements 102a, 102b, 102c of the first catheter and complementary magnetic elements 202a, 202b, 202c of the second catheter. The magnetic elements of the first catheter 102a, 102b, 102c can be spaced apart by flexible non-magnetic elements 112a, 112b (e.g., polymeric spacers or other materials, including those as disclosed elsewhere herein, including spacers permanently fixed with regard to adjacent magnets, or spacers that can be moved with respect to adjacent magnets). The magnetic elements of the second catheter 202a, 202b, 202c can also be spaced apart by flexible non-magnetic elements 212a, 212b, and be permanently fixed or movable as described elsewhere herein. As shown in FIG. 9Q, a capture element 222 such as a snare can be advanced distally out of a lumen at, for example, the distal end 201, or a sidewall port of the second catheter 200. The capture element 222 could also be movable jaws, or the like. As shown in FIG. 9R, a puncture guidewire 191 can be advanced out of a side port 195 of the first catheter 100 and through the walls of the first lumen and the second lumen to reach the interior lumen of the second lumen. This can be accomplished, for example, using electromagnetic energy (e.g., RF, microwave, and the like) using an effector at the distal end of the wire or a separate device, mechanical force, and other techniques. The puncture guidewire 191 can then be threaded through the capture element, e.g., snare 222. As shown in FIG. 9S, the capture element 222 can be withdrawn proximally back into a lumen of the second catheter, capturing the guidewire 191. As shown in FIG. 9T, the first catheter 100 and second catheter 200 can be separated from each other by overcoming the force of the respective magnetic elements, and the second catheter 200 can be withdrawn within the second body lumen 2 in direction of arrows, taking with it the puncture guidewire 191 secured within the capture element 222. The first catheter 100 can also be withdrawn within the first body lumen 1 in the direction of arrows, with puncture guidewire 191 still spanning the first body lumen 1 and the second body lumen 2. FIG. 9U illustrates puncture guidewire 191 still spanning the first body lumen 1 and the second body lumen 2 with both catheters withdrawn, and schematically illustrates that the guidewire 191 can advantageously be positioned in one of two possible directions in the second body lumen 2, either proximally 191" or distally 191' (in the same direction, or the opposite direction as within the first body lumen 1) and depending on which direction the guidewire 191 is led and released by the capture element (not shown).

Figure 9V:
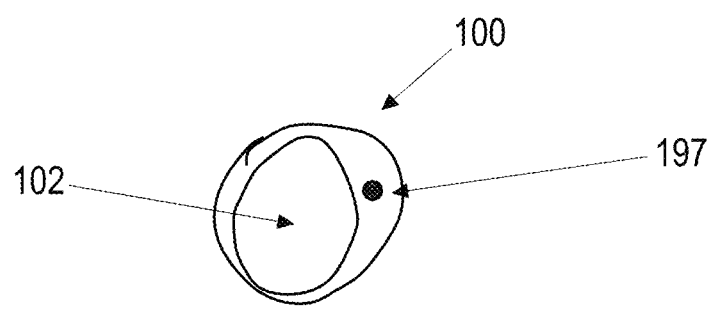
FIGS. 9V and 9W illustrate non-limiting examples of schematic cross-sectional views of a first ("donor") catheter, according to some embodiments.
Figure 9W:
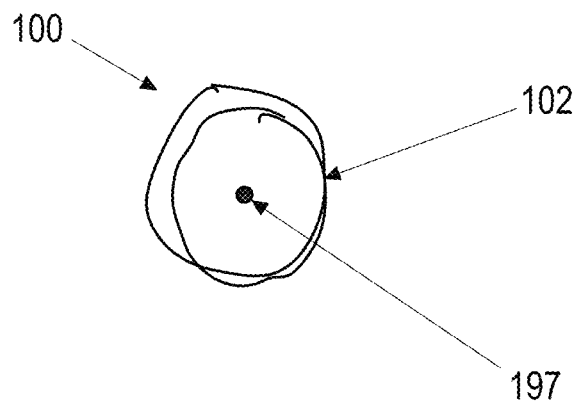

FIGS. 9V and 9W illustrate non-limiting examples of schematic cross-sectional views of a first ("donor") catheter 100, according to some embodiments. As shown in FIG. 9V, the wire lumen 197 can be generally radially outward of a magnetic element 102, or radially inward of a magnetic element 102 as shown in FIG. 9W.

Figure 9X:
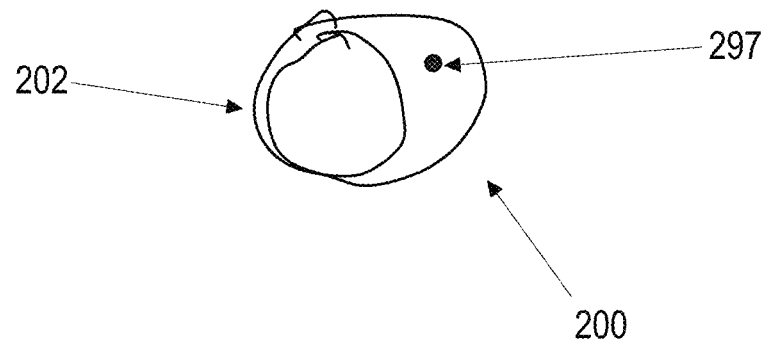
FIGS. 9X and 9Y illustrate non-limiting examples of schematic cross-sectional views of a second ("receiver") catheter, according to some embodiments.
Figure 9Y:
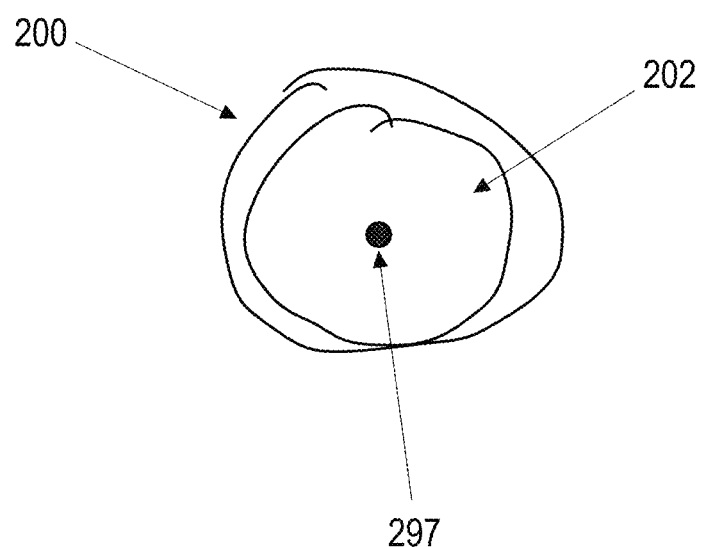

FIGS. 9X and 9Y illustrate non-limiting examples of schematic cross-sectional views of a second ("receiver") catheter 200, according to some embodiments. As shown in FIG. 9X, the capture element lumen 297 can be generally radially outward of a magnetic element 202, or radially inward of a magnetic element 202 as shown in FIG. 9Y.

Such systems and methods can be utilized for a wide variety of indications, including but not limited to the creation of hemodialysis shunts (e.g., dialysis fistulas); creation of congenital shunts; reentry devices for CTO crossing (either through AV formation or via antegrade retrograde channels in peripheral CTOs, including but not limited to CTO access from a dissection plane to a distal true lumen); endovascular peripheral arterial bypass; accessing the left or right ventricle by a percutaneous means; portacaval shunt creation; and numerous others. Systems and methods can be utilized for mitral, aortic, tricuspid, and/or pulmonic valve repair or replacement procedures. In some embodiments, systems and methods can provide venous to arterial, e.g., IVC to aorta entry for access for variety of procedures including, for example, percutaneous and transapical replacement heart valves, LVADs including IMPELLA pump devices and others, to provide transcaval access. Percutaneous bypass of diseased vessels can also be accomplished using a venous conduit or endovascular conduit. In some embodiments, access can be created across a valve leaflet to allow for the passage of electrified guidewire for a lampoon technique to lacerate the leaflet. In some embodiments, access can be utilized to deploy pledgets or stitches in surgery or percutaneous procedures across a valve. In some embodiments, AV fistulas, such as for dialysis access, can be created. Indications could be vascular (e.g., between an artery and a vein, between two arteries or segments thereof, or between two veins or segments thereof) or non-vascular (e.g., bronchial or bronchiolar lumens; gastrointestinal lumens including the esophagus, stomach, small or large intestine (e.g., to create a PEG or PEJ tube) or biliary tree; fallopian tubes, and the like. In some embodiments, systems and methods can involve intra-cranial lumens, such as vascular lumens for a neuro-interventional procedure. In some embodiments, systems and methods can be utilized for vascular graft placement, including but not limited to thoracic endovascular aortic grafts and abdominal aortic endografts for vertical spaces.

In some embodiments, the catheter can include a magnetic flux density measured at a point at the surface of the magnet(s) of, for example, between about 1,000 Gauss and about 12,000 Gauss, between about 3,000 Gauss and about 10,000 Gauss, between about 3,000 Gauss and about 8,000 Gauss, between about 5,000 Gauss and about 10,000 Gauss, between about 5,000 Gauss and about 8,000 Gauss, or about 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000 Gauss, or ranges including any two of the aforementioned values. In some embodiments, the magnet comprises a plurality of magnets that are longitudinally (as opposed to axially) polarized.

In some embodiments, magnets can include cylindrical and/or elliptical shapes. The magnets can have, for example a major axis and/or minor axis diameter of, for example, between about 0.3 mm and about 7.0 mm, or about, at least about, or no more than about 0.3 mm, 0.5 mm, 0.8 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, or ranges including any two of the foregoing values.

In some embodiments, a magnet can function as a single magnet, but be part of a magnet array to advantageously increase the total surface area. In some embodiments, the magnet arrays can have any desired cross-section, such as spheres, cylinders, pie-shaped segments, C-shaped, D-shaped, L-shaped, and other geometries. Each magnetic element can also include a plurality of micro-magnets functioning as a single magnet.

In some embodiments, each magnet can have a length of, for example, between about 0.5 cm and about 8 cm, between about 1 cm and about 5 cm, or about, at least about, or no more than about 0.5 cm, 1 cm, 2 cm, 3 cm, 4 cm, 5 cm, 6 cm, 7 cm, 8 cm, or ranges including any two of the foregoing values.

In some embodiments, the catheter can have an outer diameter of, for example, between about 0.5 mm (e.g., arterial, peripheral venous) and about 8 mm (e.g., major vessel, venous), between about 1 cm and about 5 cm, or about, at least about, or no more than about 0.5 cm, 1 cm, 2 cm, 3 cm, 4 cm, 5 cm, 6 cm, 7 cm, 8 cm, or ranges including any two of the foregoing values.

In some embodiments, the catheter can have a French size of, for example, from about 2F and about 24F, or about 2F, 3F, 4F, 5F, 6F, 7F, 8F, 9F, 10F, 11F, 12F, 13F, 14F, 15F, 16F, 17F, 18F, 19F, 20F, 21F, 22F, 23F, 24F, or ranges including any two of the foregoing values.

In some embodiments, the catheter can include one or more lumens therein having a diameter of, for example, between about 0.014 inches and about 0.035 inches, to allow for delivery of guidewires, snares, and other instruments therethrough.

In some embodiments, magnets can be immediately opposed and directly contacting each other. In some embodiments, magnets can be spaced apart along the long axis of the catheter from each other, such as, for example, about or no more than about 0.1 cm, 0.2 cm, 0.3 cm, 0.4 cm, 0.5 cm, 0.6 cm, 0.7 cm, 0.8 cm, 0.9 cm, 1.0 cm separation from each other, or ranges including any two of the aforementioned values. In some embodiments, the magnets can be spaced apart by flexible non-magnetic elements, including but not limited to flexible polymer spacers (e.g., in an axial, radial, and/or transverse direction, such as only an axial direction in some cases). In some embodiments, the spacers are configured to be fixed in place on the device (e.g., catheter or a wire, for example) between the magnets throughout the entire procedure, in other words, permanently fixed in between adjacent magnets. In some embodiments, the spacers do not comprise any apertures within the spacers, and/or are not aligned along a tether, such that they can advantageously remain to modulate magnet strength throughout the entire procedure. In some embodiments, the spacers can be made of any number of, or any combination of maleimides, acrylates, vinyl ethers, vinyl esters, urethanes, polyesters, polyester-linked methacrylates, styrenic compounds, epoxies, silane modified epoxies, amine modified epoxies, silicones, liquid rubber, allyl functional compounds and mixtures of two or more thereof. Other filler and/or spacer material include inorganic material such as aluminum nitride, boron nitride, alumina, silicon dioxide and uncrosslinked organic material like perfluorinated hydrocarbons, polyalkylsilsesquioxane, uncrosslinked polymers such as acrylates, alpha-olefins, vinyl esters, acrylamides, acrylonitriles, maleimides, urethanes and others. In some embodiments, the spacers can comprise polypropylene.

Figure 10A:
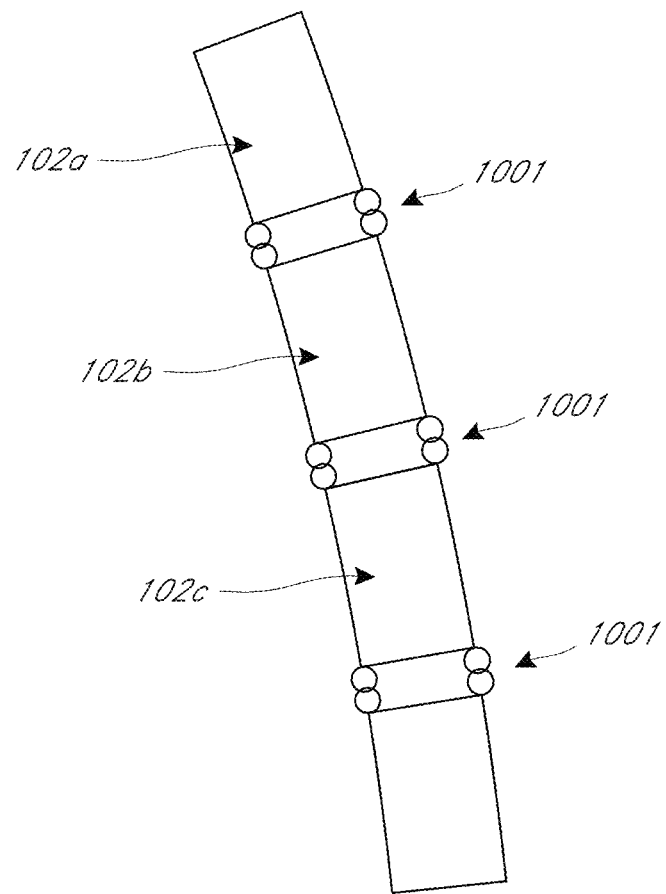
FIGS. 10A-16 schematically illustrate additional features of magnetic catheter systems and methods, according to some embodiments.
Figure 10B:
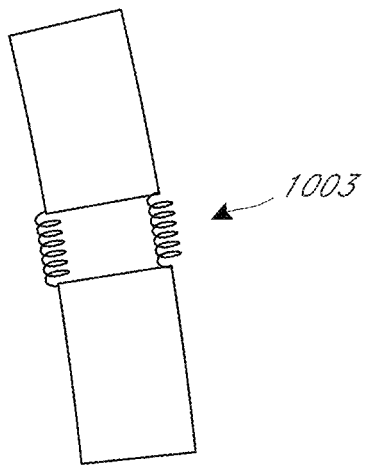
Figure 10C:
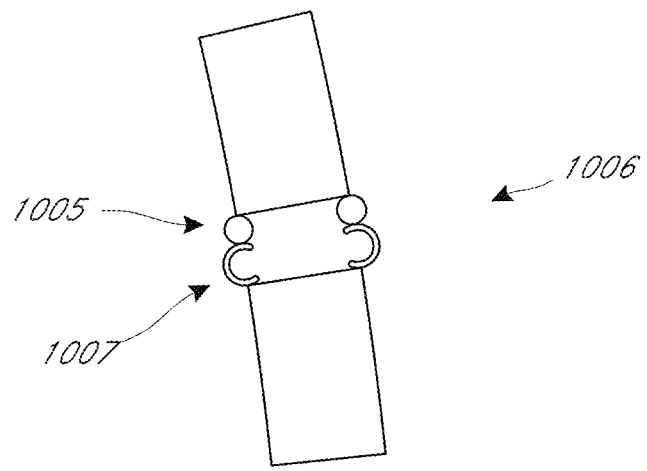

In some embodiments, as illustrated in FIGS. 10A-10C the spaced-apart magnets can be operably connected axially by movable structures, such as facet hinges or joints for example. FIG. 10A illustrates axially spaced-apart magnets 102 with hinges 1001 in between each adjacent pair of magnets 102. FIG. 10B illustrates axially spaced-apart magnets 102 with springs 1003 in between each adjacent pair of magnets 102. In some embodiments, as shown in FIG. 10C, the movable structures can include a combination of eyelets 1005 connected to hooks 1007 (or springs or other structures) as illustrated. In some embodiments, as shown in FIGS. 10A-10C the movable structures attach to less than the entire perimeter of the end walls of the magnets, for example, such as only at the distal end vertices of a first magnet and a distal end vertices of a second magnet as shown.

In some embodiments, the axial length of each of the magnetic elements is greater than or equal to the axial length of each of the flexible non-magnetic elements, such as spacers for example. The axial length of each of the magnetic elements can be, for example, about, at least about, or no more than about 5%, 10%, 20%, 30%, 40%, 50%, 60%, 70%, 80%, 90%, 100% greater than that of the axial length of each of the non-magnetic elements, or ranges including any two of the foregoing values.

Figure 10D:
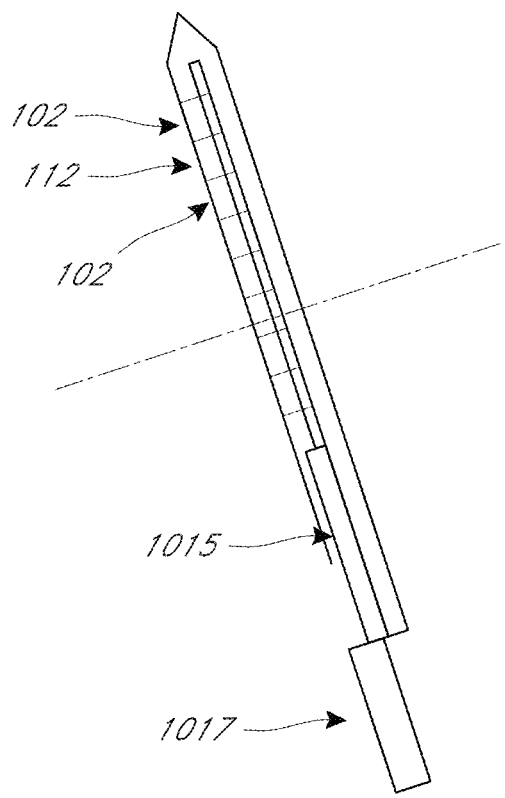
Figure 10E:
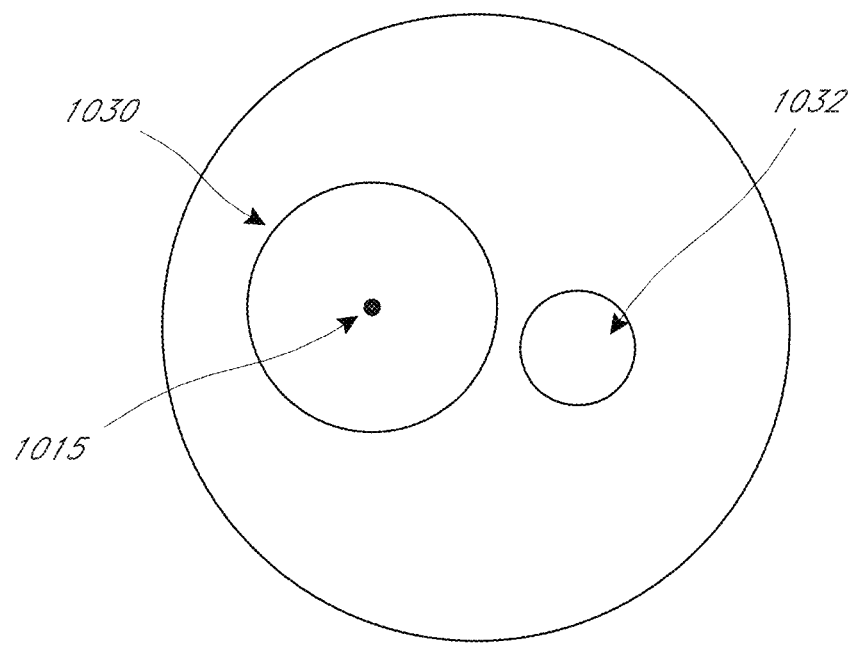
Figure 10F:
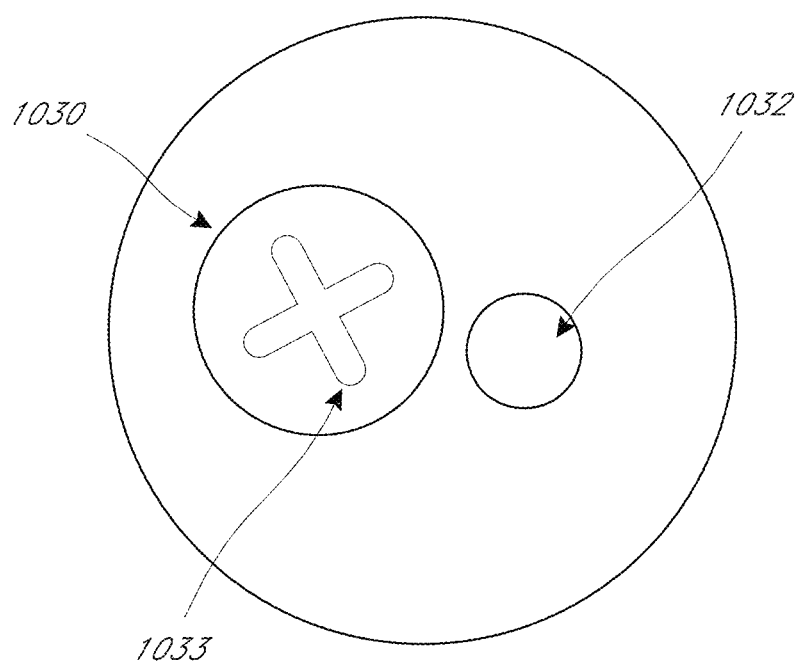

In some embodiments, the magnets are fixed (e.g., non-movable) with respect to each catheter, and can move with respect to each of the catheters. However, in some embodiments, the magnets are configured to be movable in one, two, or more directions with respect to each catheter. In some embodiments, a plurality of magnets can be spaced regularly or irregularly apart on an elongate member, such as an elastic or non-elastic tether, wire, or the like. The magnets can be interspersed with spacers as disclosed elsewhere herein, or without spacers (e.g., blank spaces in between magnets). FIG. 10D schematically illustrates magnets 102 axially spaced apart from each other by spacers 112 along an elongate member 1015 such as a mandrel, wire, tether, and the like. The proximal end of the elongate member 1015 includes a handle 1017 that can be a torqueing element configured to allow an operator to axially advance or withdraw, and/or rotate the elongate member 1015 (and the magnets 102 thereon) with respect to the catheter within a lumen of the catheter. FIG. 10E schematically illustrates a cross-sectional view through a catheter, illustrating a first lumen 1030 configured to house the elongate member 1015 including the axially spaced-apart magnets, and a second lumen 1032 configured to house a guidewire for an over-the-wire purpose or to house a puncture wire mechanism. In some embodiments, the first lumen 1030 has a diameter that is the same size as, or larger, such as about, at least about, or no more than about 10%, 25%, 50% 75%, 100%, 150%, 200%, 250%, or more or less larger than that of the second lumen 1032, or ranges including any two of the foregoing values. FIG. 10F schematically illustrates a cross-sectional view through a catheter that can be similar to that of FIG. 10E, illustrating that the elongate member, such as the proximal end can be fused or otherwise welded together with a gear mechanism 1033 configured to actuate the elongate member axially and/or radially, for example while housed within the first lumen 1030.

In some embodiments, the distance between magnets can be adjustable by moving individual magnets along the elongate member. The elongate member can reside within the central lumen, or in one, two, or more auxiliary lumen(s) offset from the central lumen within each catheter, and can move, for example, axially and/or rotate with respect to the catheter (e.g., by advancement, retraction, or rotation of the proximal end of the elongate member by an operator) to advantageously allow for altering the magnetic forces in between catheters of each lumen without necessarily needing to move the actual catheters themselves.

In some embodiments, a catheter or a portion thereof can include a coating or lubrication layer, for example, on an external surface. The coating could be hydrophilic or hydrophobic. Hydrophobic coatings have been used to impart lubricity to medical devices including silicone based lubricants, glycerin or olive oil. Examples of silicone based lubricants include polysiloxanes and modified polysiloxanes. Often they include a polar group which may be an aminoalkyl or carboxyalkyl terminating group. Some lubricating compositions can include, for example, noncuring polysiloxane, a surfactant and/or water. In some embodiments, a protective lubricious coating comprising providing a coating solution which contains a protective compound such as a urethane, a slip additive such as a siloxane, and optionally, a crosslinking agent for the protective compound such as polyfunctional aziridine, coating the solution onto a surface of a medical apparatus and allowing the coating to set. Another approach for reducing the coefficient of friction can include a low friction material such as polytetrafluoroethylene (PTFE). Hydrophilic compounds have also been used to impart lubricity in medical devices. Such compounds are biocompatible or blood compatible, and are more readily discharged from the body and have less of a tendency to cause tissue irritation. Examples of such polymeric materials include Nylon, Selar, polyethylene terephthalate, polyethylene or similar materials. A blood-compatible coating is polyethylene glycol, methoxy polyethylene glycol or mixtures thereof having a molecular weight between about 100 and 20,000 grams per mole. In some embodiments, the magnets can be positioned within each device such that the magnets do not directly contact a body fluid, such as the bloodstream for example. The magnets can be positioned inside of a catheter, such as an auxiliary lumen for example.

The magnets can also be positioned along an outer diameter of a catheter, but radially inward of an outer layer, such as a relatively thin non-magnetic layer for example.

Figure 10G:
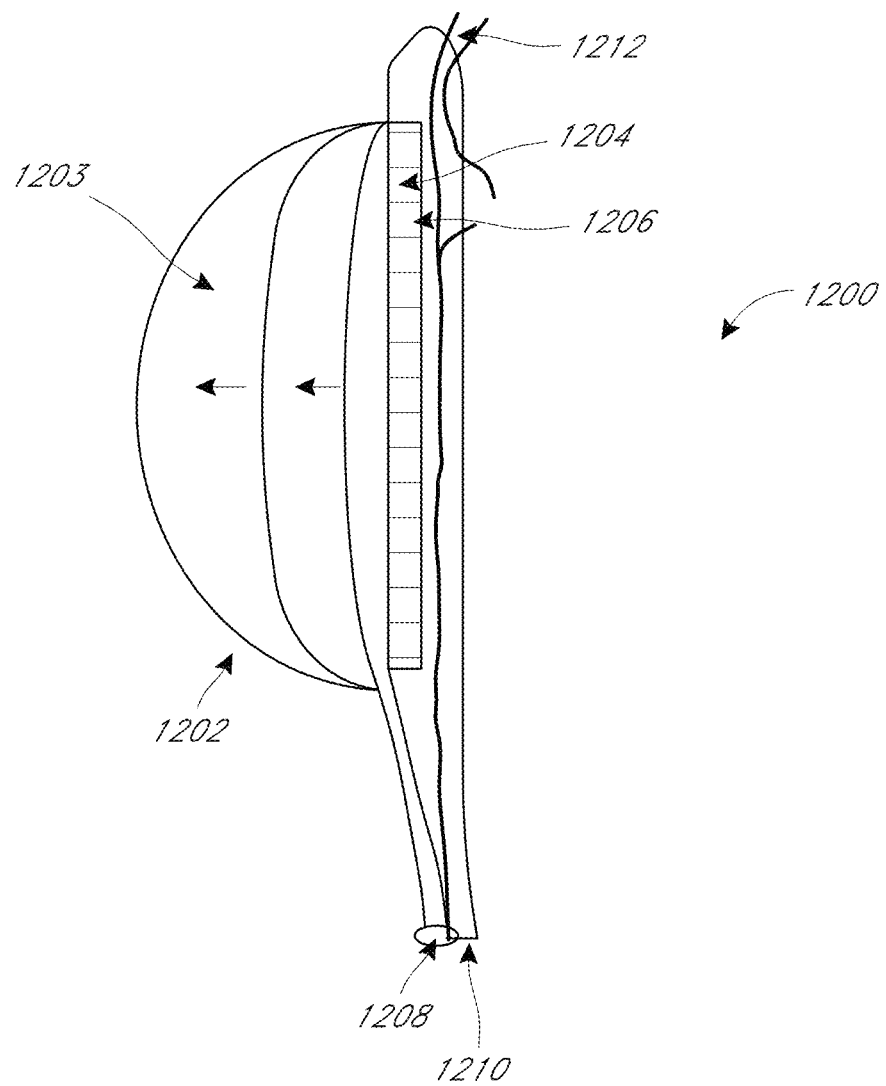

FIGS. 10G-10J schematically illustrate examples of embodiments of a catheter system including expandable structures configured to, when expanded, maintain the position of either a donor and/or receiving catheter at a desired location within body lumen(s). FIG. 10G schematically illustrates a catheter 1200 and an inflatable, expandable structure comprising a balloon 1202, as well as a plurality of magnets as can be described elsewhere herein. The balloon 1202 can be circumferentially expandable, or asymmetrically expandable only on one side, such as about 180 degrees of the circumference of the balloon 1202, or less in some cases. The asymmetrically expandable side 1203 of the balloon 1202 can be configured to expand against the side of the lumen where puncture through the luminal wall is contemplated. The balloon 1202 could be compliant, semi-compliant, or noncompliant. The balloon 1202 could be any desired geometry, such as round, elliptical/elongated, or other geometries. The catheter 1200 can include at least a balloon inflation lumen 1208, and a lumen 1210 configured to house a over-the-wire guidewire and/or a puncture wire therethrough. The catheter 1200 can also include an exit port 1212 configured to allow a puncture wire, capture device, or other element to exit out of the catheter 1200, e.g., distal to the balloon.

Figure 10H:
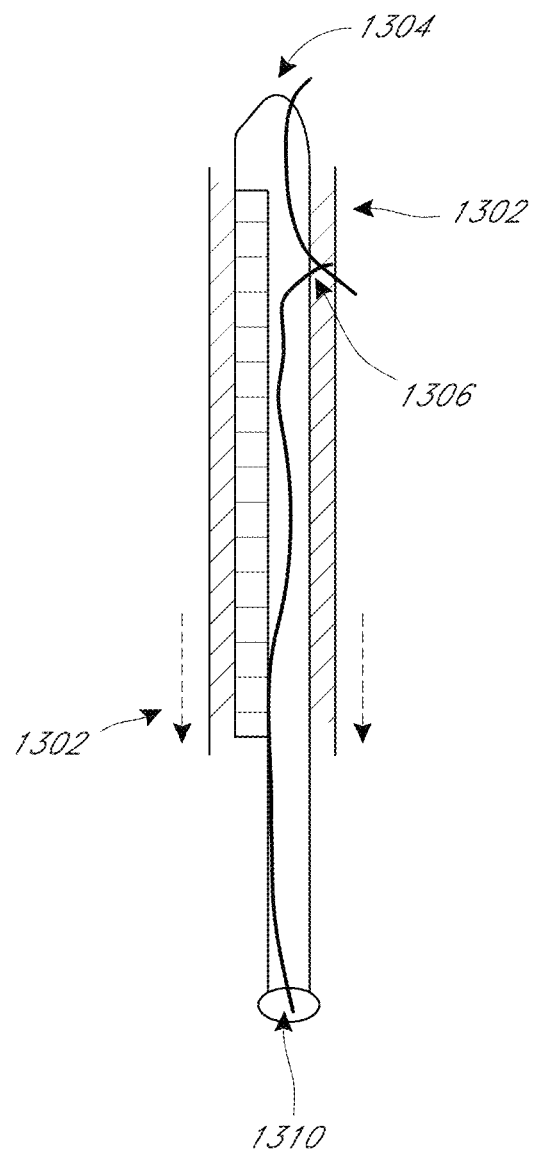
Figure 10I:
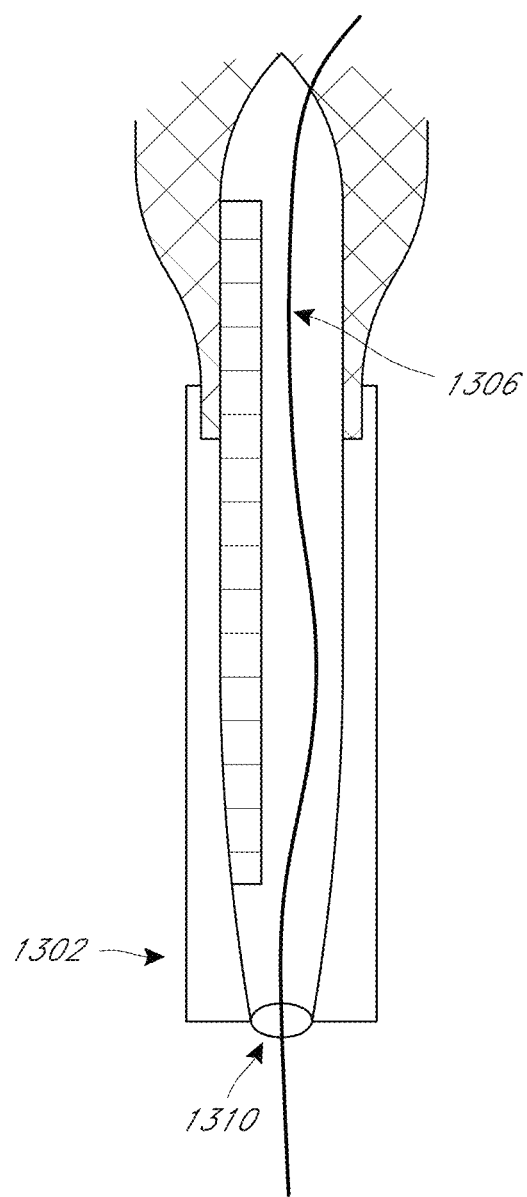
Figure 10J:
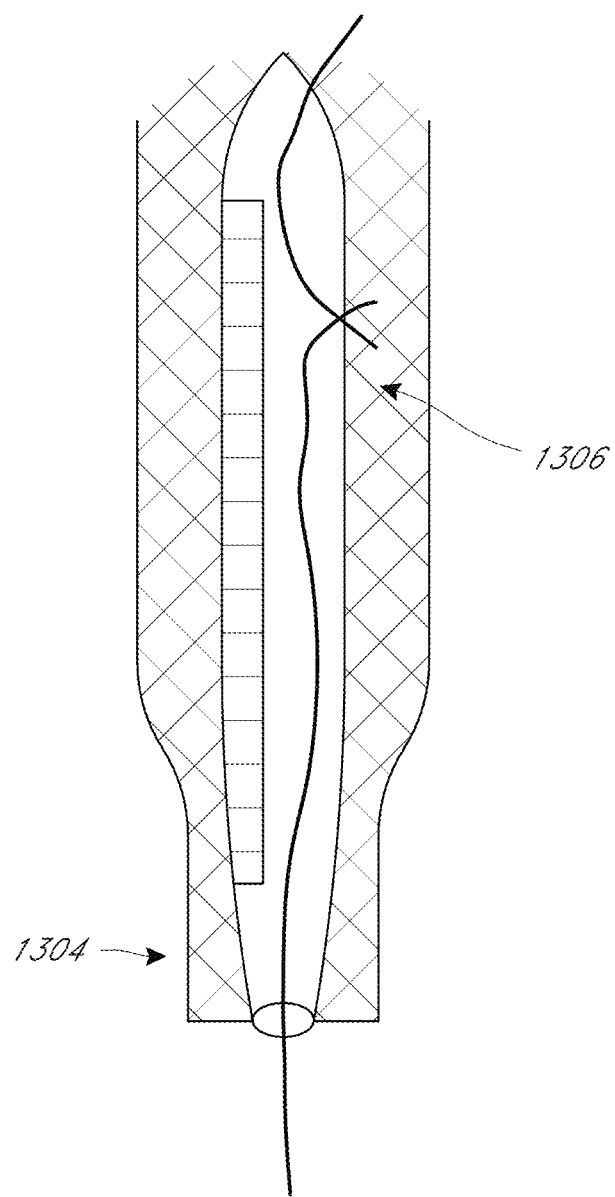

FIG. 10H schematically illustrates a catheter system where the expandable structure is not necessarily a balloon, but rather a radially expandable cage or stent 1306, made of a shape memory material such as nitinol; stainless steel, or other materials, for example. The expandable structure 1306 can be self-expandable as shown or balloon-expandable in other embodiments. The cage or stent 1306 can have a variety of geometries and wall patterns as known in the art, be configured to symmetrically or asymmetrically expand, and be configured to rest against the wall of the lumen either fully or only partially circumferentially as described above. The expandable structure 1306 can be disposed within an outer catheter or sheath 1302, while an inner catheter 1304 can include magnetic elements as described elsewhere herein. The catheter can also include a wire lumen 1310 that can be as previously described. As illustrated schematically in FIG. 10I, advancement of the inner catheter 1304 with respect to the outer catheter 1302, or retraction of the outer catheter 1302 with respect to the inner catheter 1304 results in the expandable member 1306 assuming its radially expanded and unconstrained configuration. FIG. 10J schematically illustrates the fully unconstrained expandable member 1306 with the outer catheter 1302 removed.

In some embodiments, the expandable structures are configured to maintain blood flow when expanded within a vascular lumen (e.g., via a through lumen in the catheter). In some embodiments, the expandable structures inhibit or halt blood flow when expanded within a vascular lumen.

In some embodiments, a catheter system can be configured to include a stent configured to be placed on an external diameter of a donor catheter and/or the receiving catheter, such as proximal to the exit port for the puncture wire, or proximal to the magnetic elements in some embodiments. The stent can be deployed as part of an emergency bailout procedure in case of an inadvertent puncture, rupture, or dissection through a vessel wall to cover the iatrogenic or other defect in the vessel. The stent could a covered stent in some cases, including a fabric or graft material such as PTFE or ePTFE (e.g., Gore-Tex), for example.

Figure 11A:
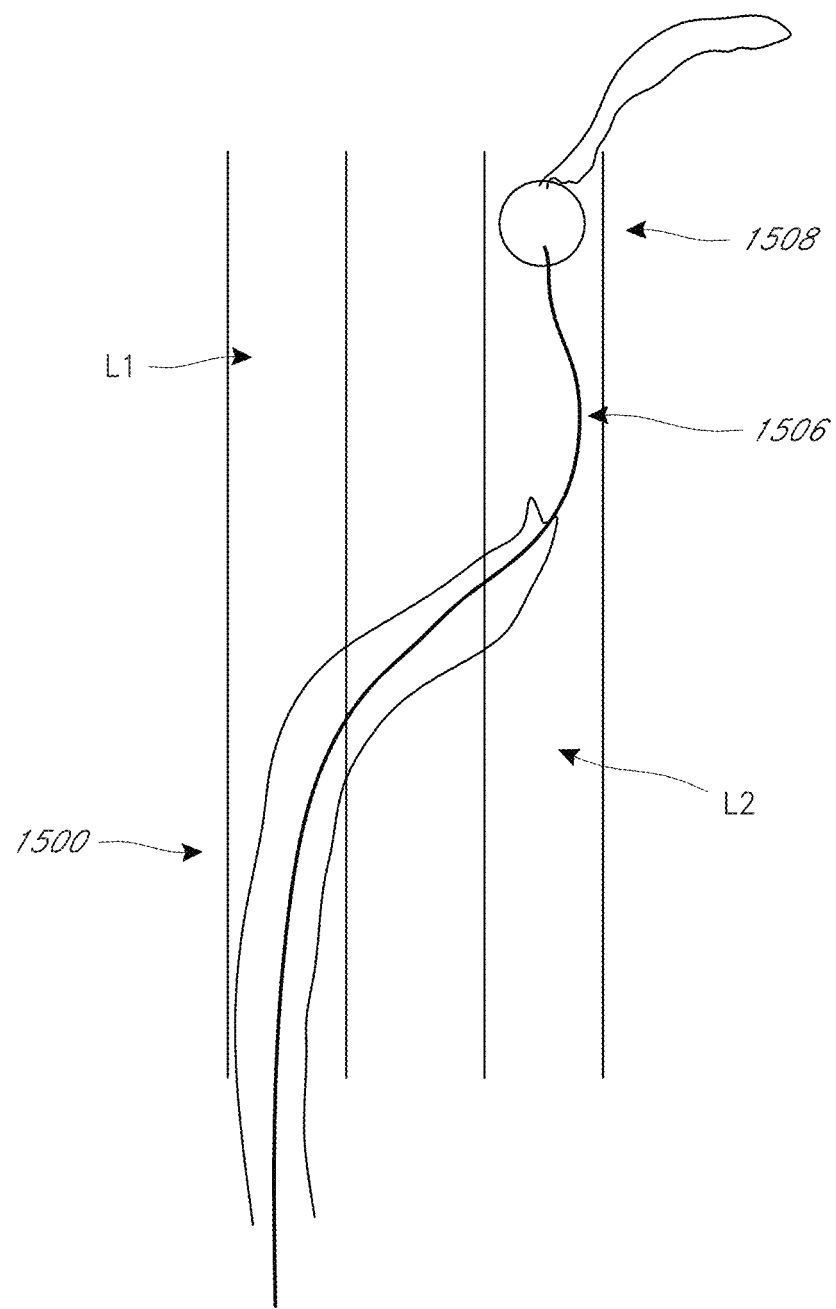
Figure 11B:
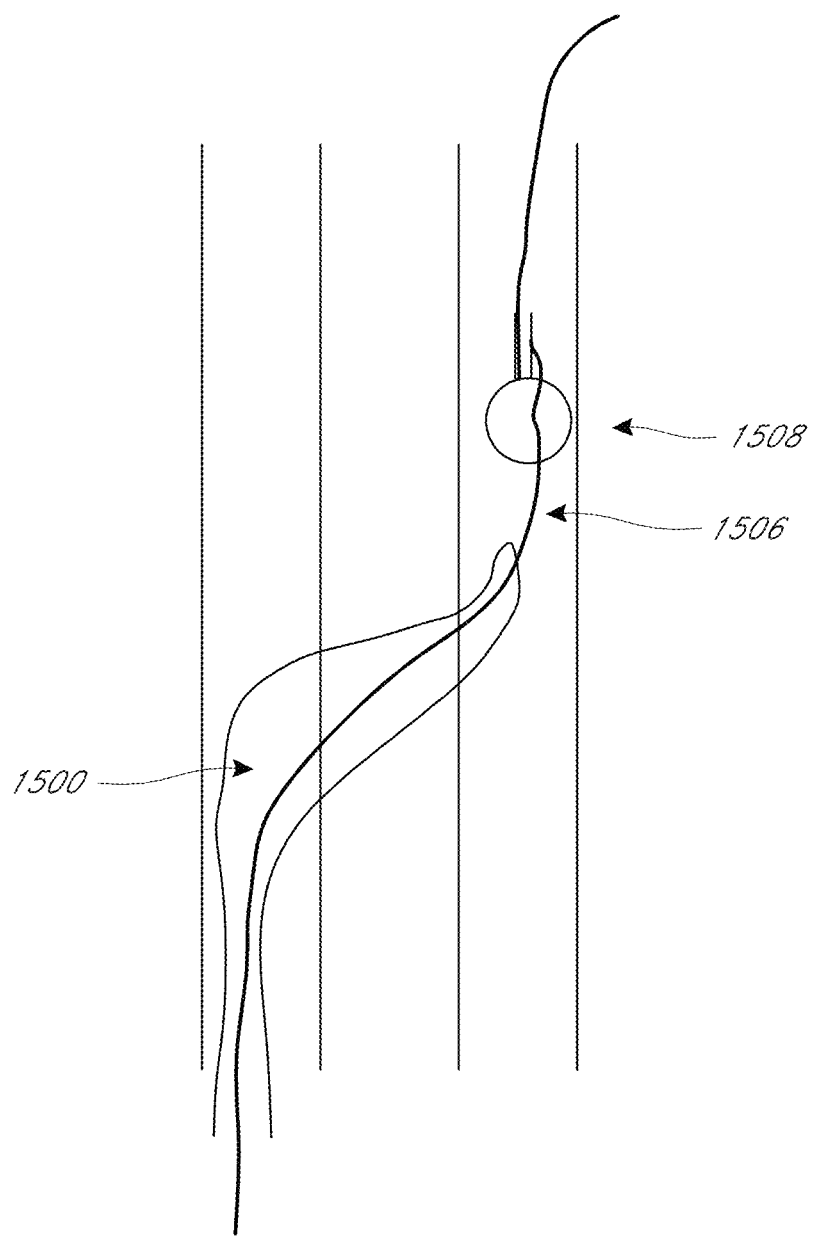
Figure 11C:
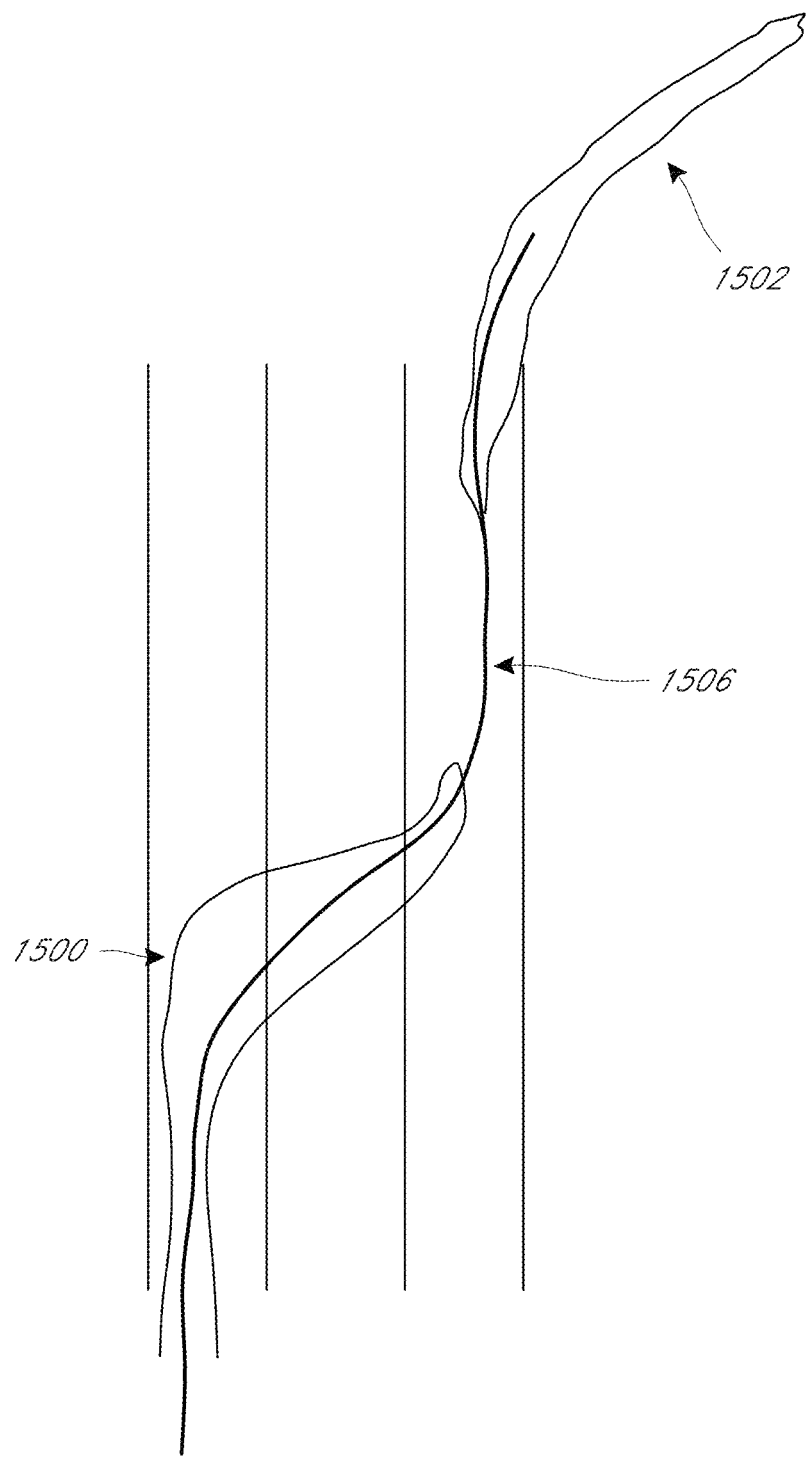
Figure 11D:
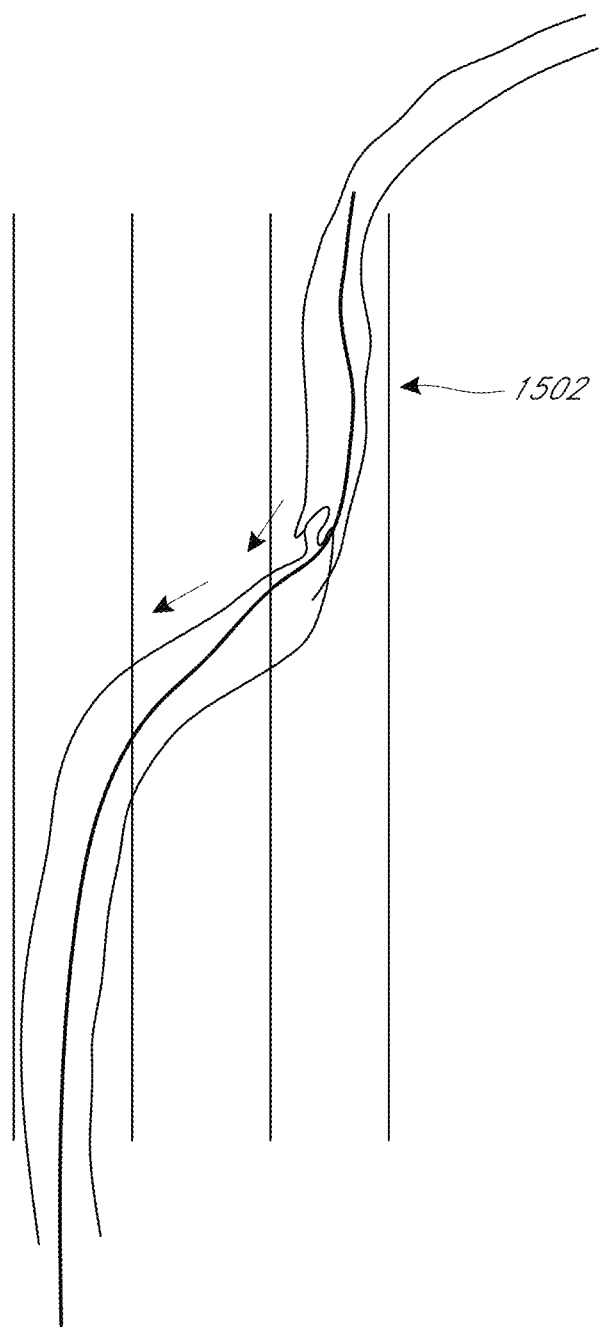
Figure 11E:
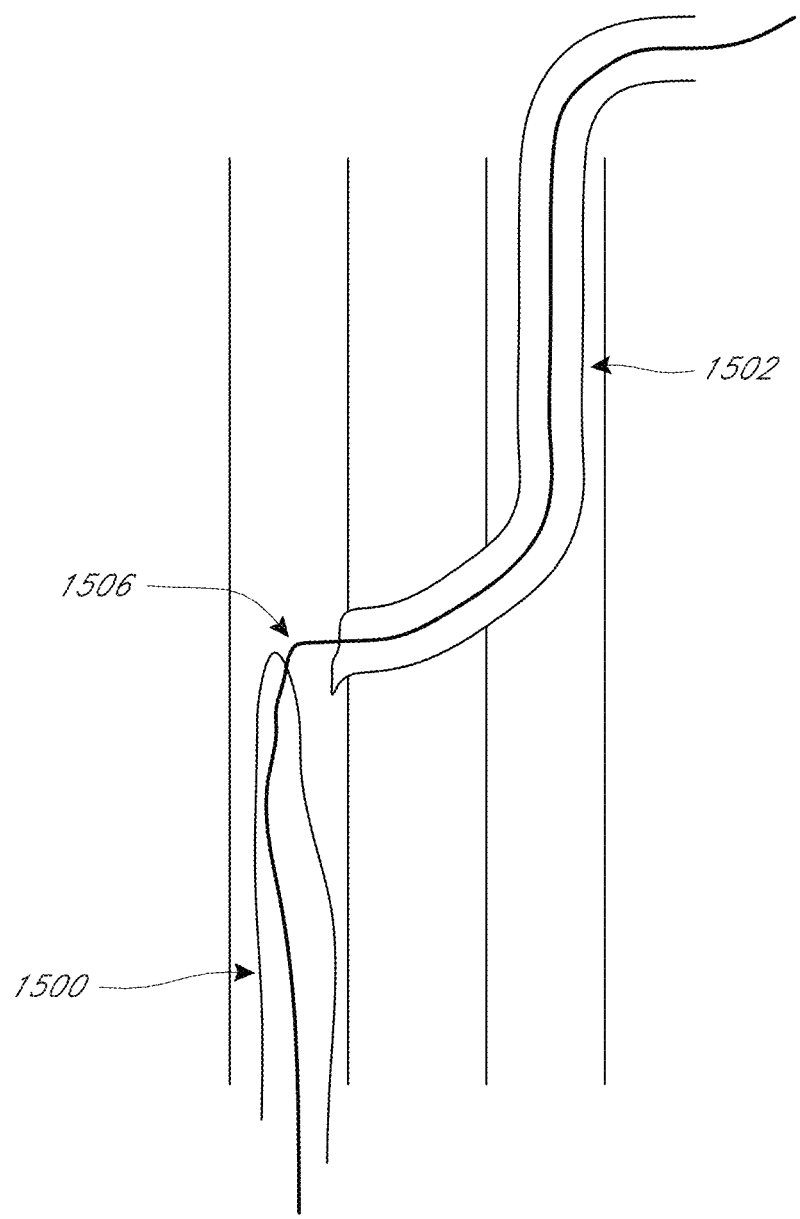
Figure 11F:
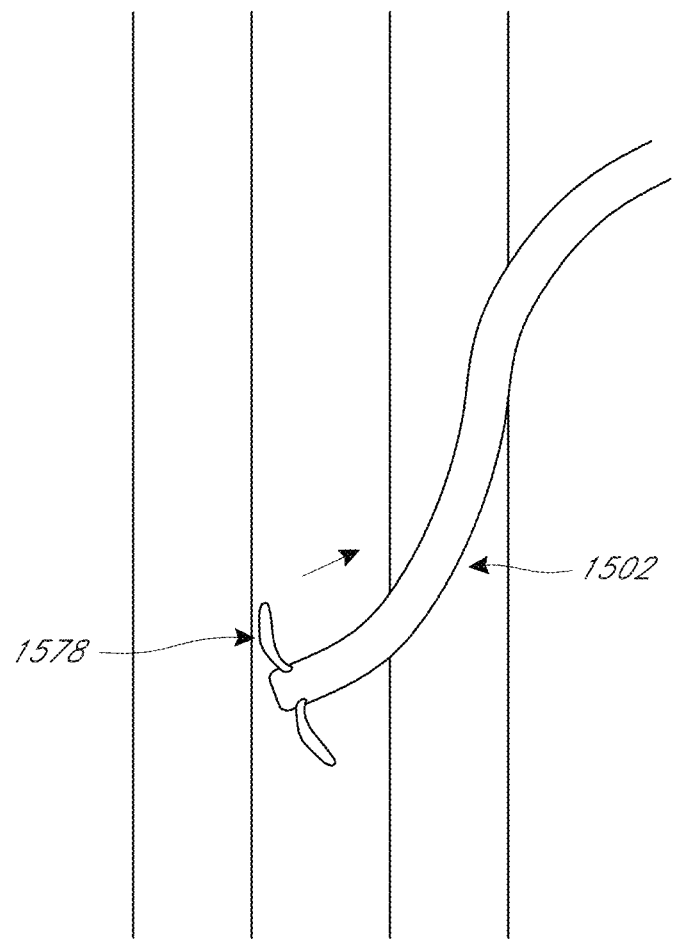
Figure 11G:
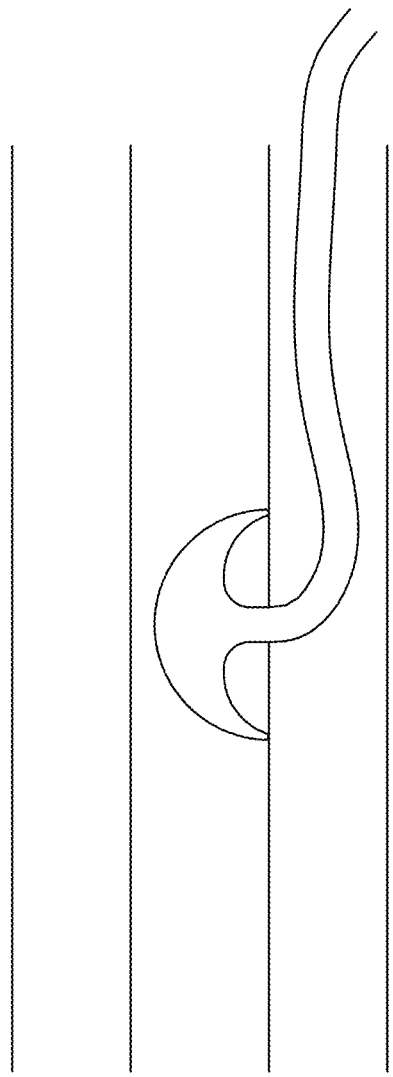
Figure 11H:
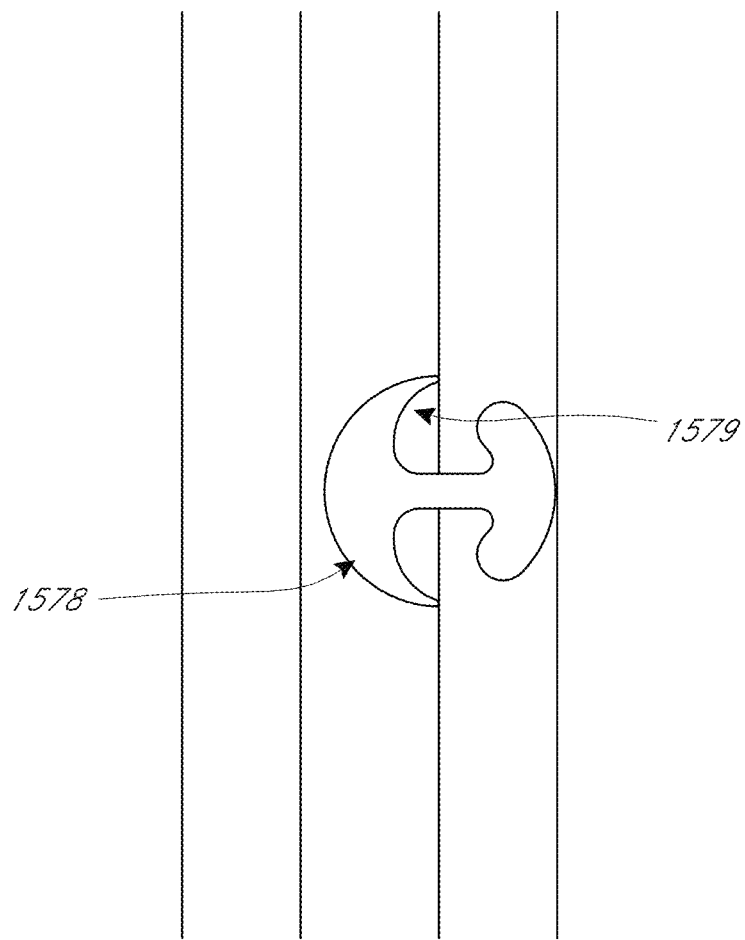
Figure 111:
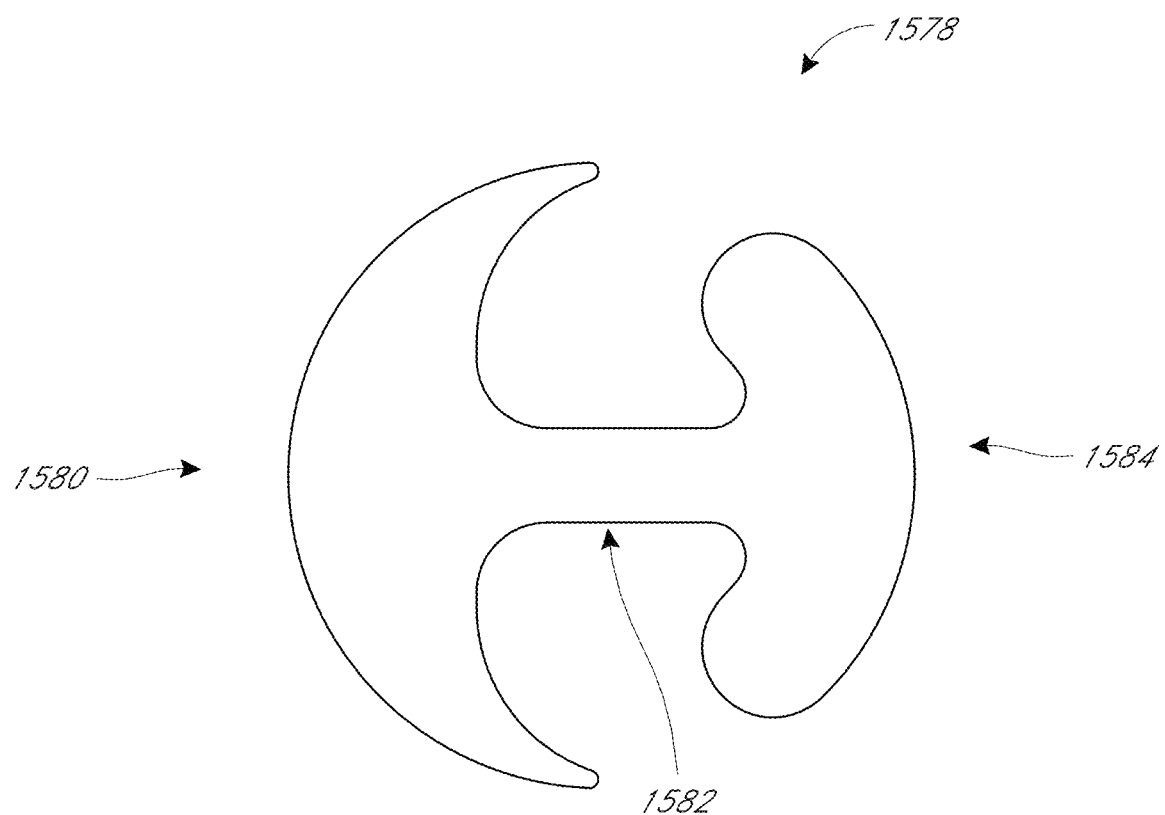

In some embodiments, a catheter system can include an integrated luminal closure mechanism and method of use. As shown schematically in FIG. 11A, a (first) donor catheter 1500 can include a puncture wire 1506 that traverses the luminal wall of the first lumen L1 and the external wall of the second lumen L2, into a capture element 1508, such as a snare that can be as described elsewhere herein. FIG. 11B schematically illustrates the capture element 1508 capturing the puncture wire 1506. FIG. 11C illustrates the (second) receiving catheter 1502 being advanced further into the second lumen L2. FIG. 11D illustrates the second catheter 1502 being advanced over the puncture wire 1506 through the luminal wall of the second lumen L2 and the external wall of the first lumen L1. FIG. 11E illustrates the second catheter 1502 being slightly withdrawn, and FIG. 11F illustrates a closure element 1578 being deployed distally out of the second catheter 1502 in the space between the first lumen L1 and the second lumen L2. FIG. 11G illustrates the closure element 1578 with a proximal-facing surface 1579 resting against the external wall (e.g., adventitia) of the second lumen L2. FIG. 11H illustrates the closure element 1578 in place against the wall of the second lumen L2 and maintaining the integrity of the luminal wall. The closure system and method can be uniquely deployed obliquely to the longitudinal axis of the wall of the second lumen L2 (and the first lumen in some cases), such as at an angle of between about 10 degrees and about 90 degrees, between about 20 degrees and about 80 degrees, between about 30 degrees and about 60 degrees, about 35, 40, 45, 50, 55, or 60 degrees, or ranges including any two of the foregoing values. The closure device can include a "T," "H," or other-shaped pledget in some cases, with the transverse cross-bar like portion of the H as illustrated configured to be angled obliquely with respect to the longitudinal portions of the closure device and/or the vessel wall at angles, for example, described above. In some embodiments, in addition to, or instead of a mechanical closure device, closure can be achieved using a closure formulation, such as an adhesive, such as a cyanoacrylate, for example. In some embodiments, the closure formulation can be released from a reservoir within a lumen of the catheter, or injected from the proximal end of the catheter.

FIG. 11I schematically illustrates an embodiment of a closure device 1578 with a first elongate member 1580, an angled/oblique transverse member 1582 that can be similar to a crossbar in some cases, and a second elongate portion 1584 that can be substantially parallel to the first elongate portion 1580. A length of a first elongate portion 1580 and/or a second elongate portion 1584 of the closure device 1578 can be about, at least about, or no more than about 1.25×, 1.5×, 1.75×, 2×, 2.5×, 3×, 4×, 5×, or more or less compared to the length of the transverse portion 1582, or ranges including any two of the foregoing values.

Figure 11J:
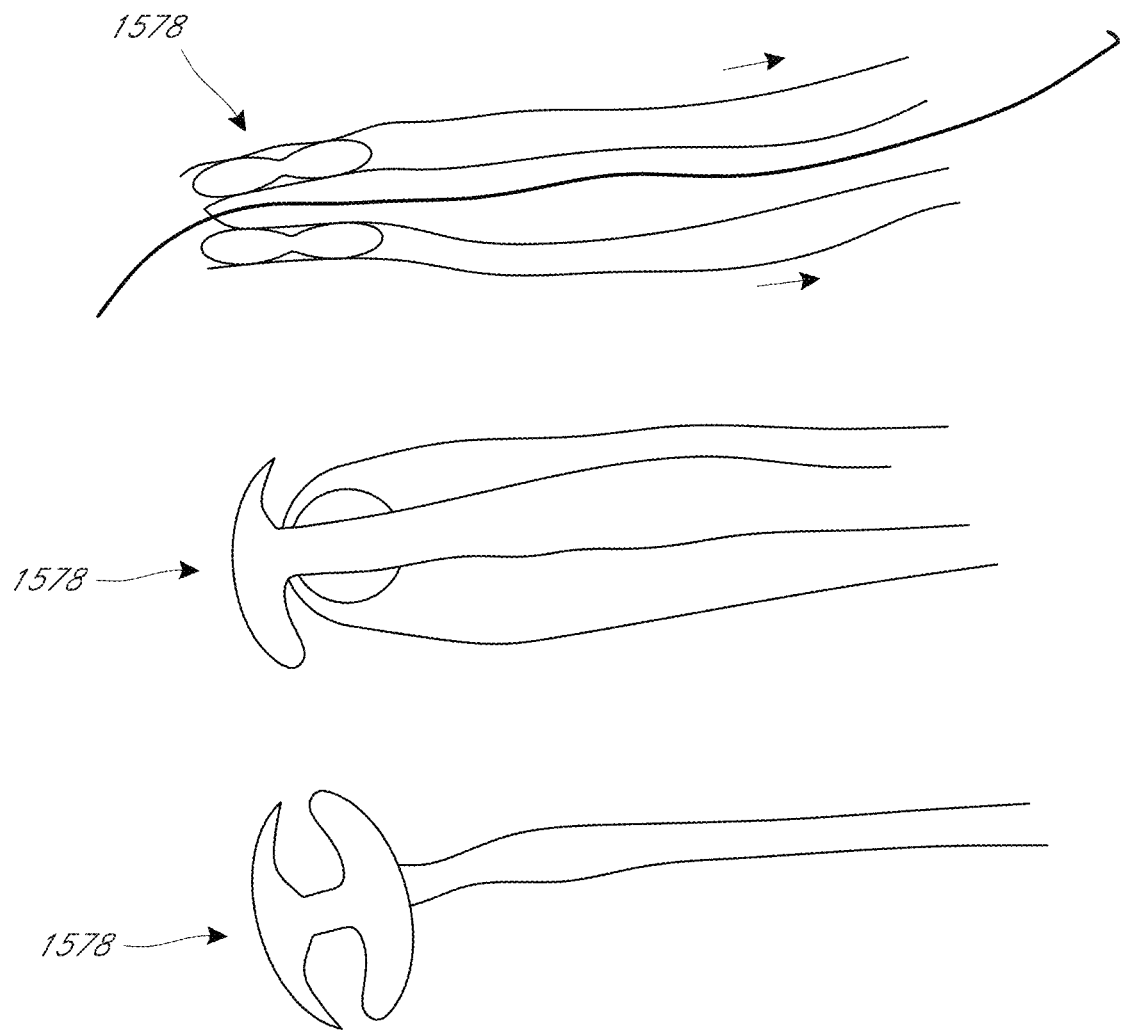

FIG. 11J schematically illustrates schematically a closure element being deployed from a catheter, according to some embodiments.

In some embodiments, the catheter system could utilize either Over-the-Wire (OTW) or Rapid Exchange (Rx, also known as monorail) configurations depending on the desired clinical result. Over-the-wire (OTW) balloon catheters feature a guidewire that tracks along the full length of the catheter. One potential advantage of an over-the-wire balloon is better ability to push the balloon and change the wire, if needed, distal to the treatment site. One potential disadvantage is the wire over which the balloon tracks must be, in some cases, at least twice the length of the balloon. When working with short, peripheral balloons, the length of wire required is not problematic. Rapid exchange (RX) balloon catheters have a guidewire along only a short section (about 20-30 cm in some cases, such as from the distal tip of the catheter), saving time compared with advancing a guidewire through the full length of the catheter. Furthermore, Rx catheters may have a smaller crossing profile as they do not require a discrete guidewire lumen extending all the way back proximally to the proximal end of the catheter. One potential disadvantage of the Rx catheter configuration is that the balloon cannot be used to change wires distal to the obstruction, and there is less "pushability" because the wire does not run the length of the balloon.

Figure 12A:
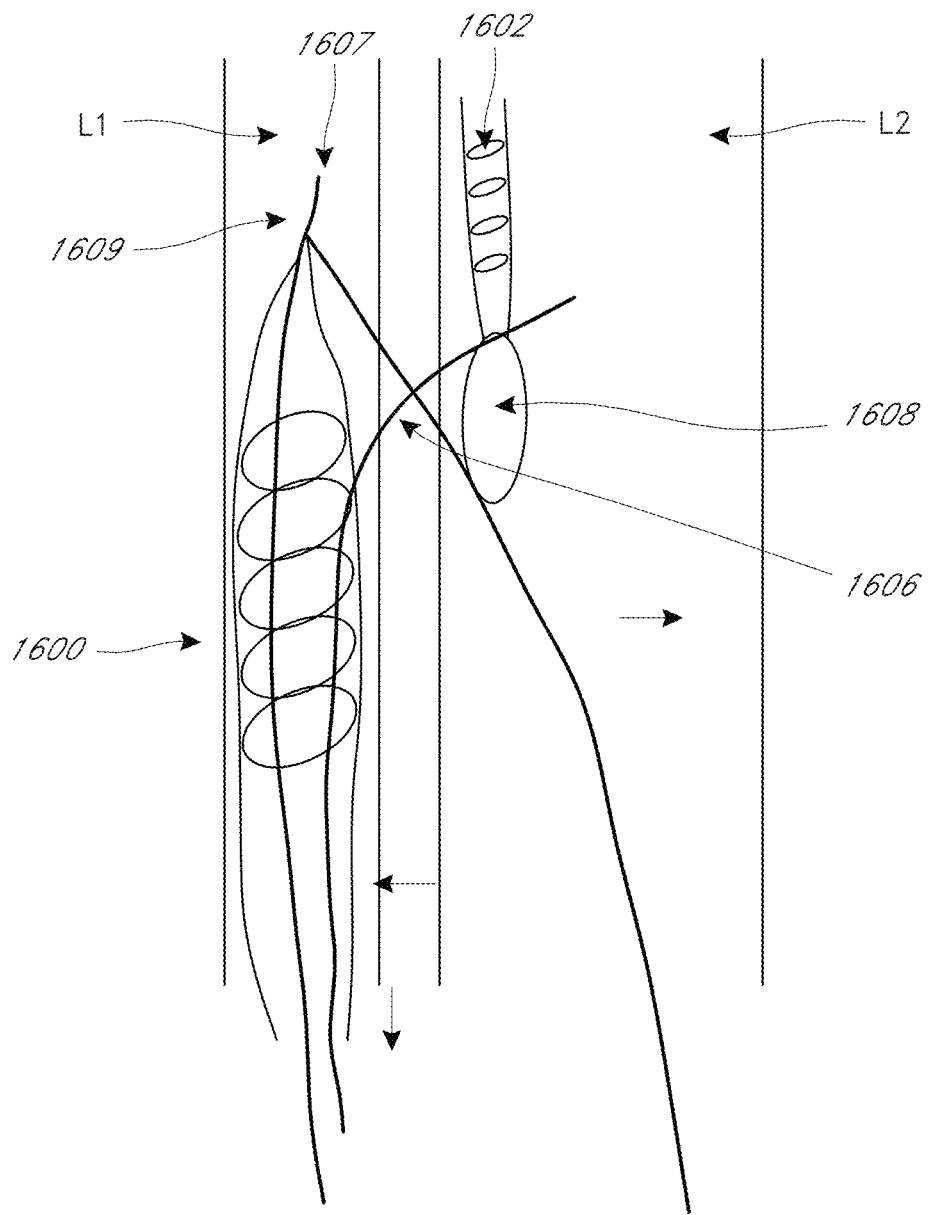
Figure 12B:
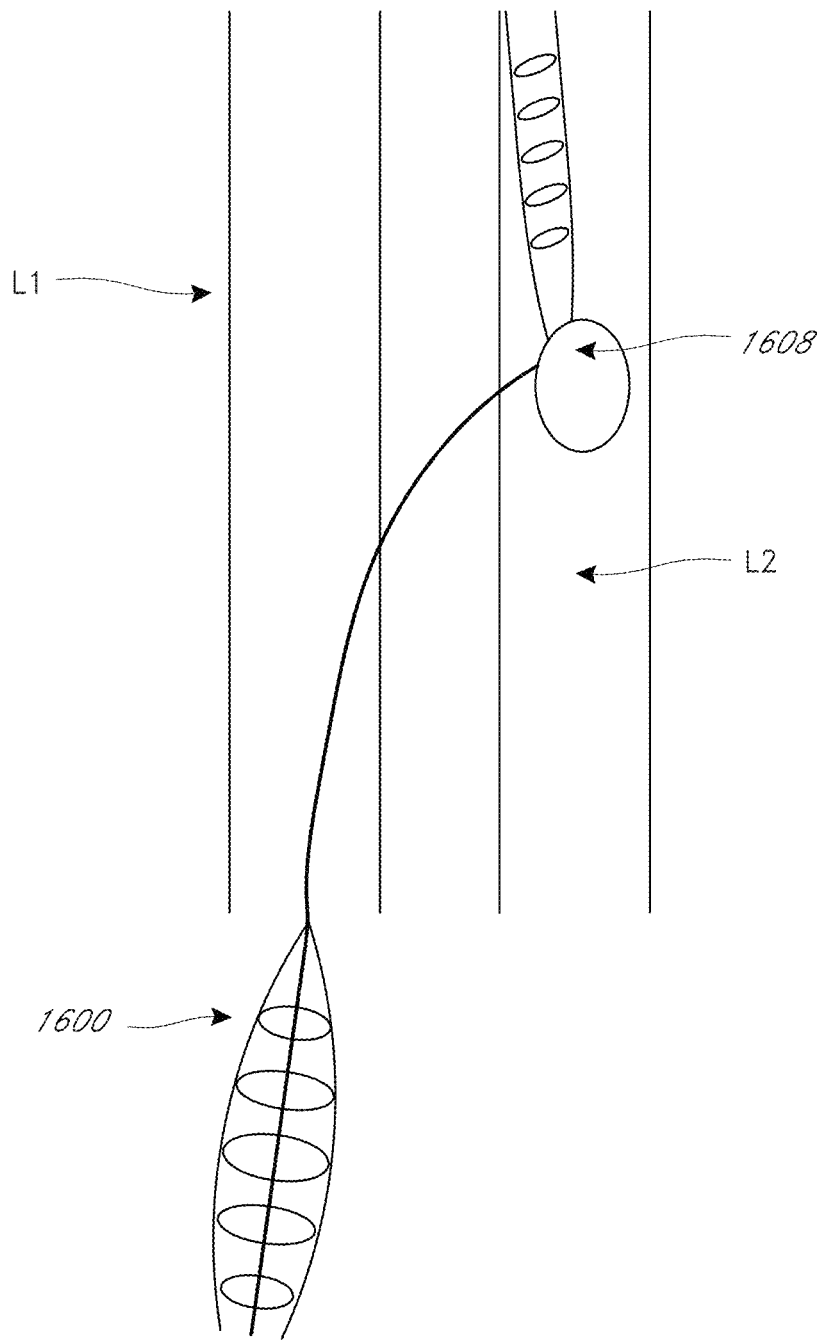
Figure 12C:
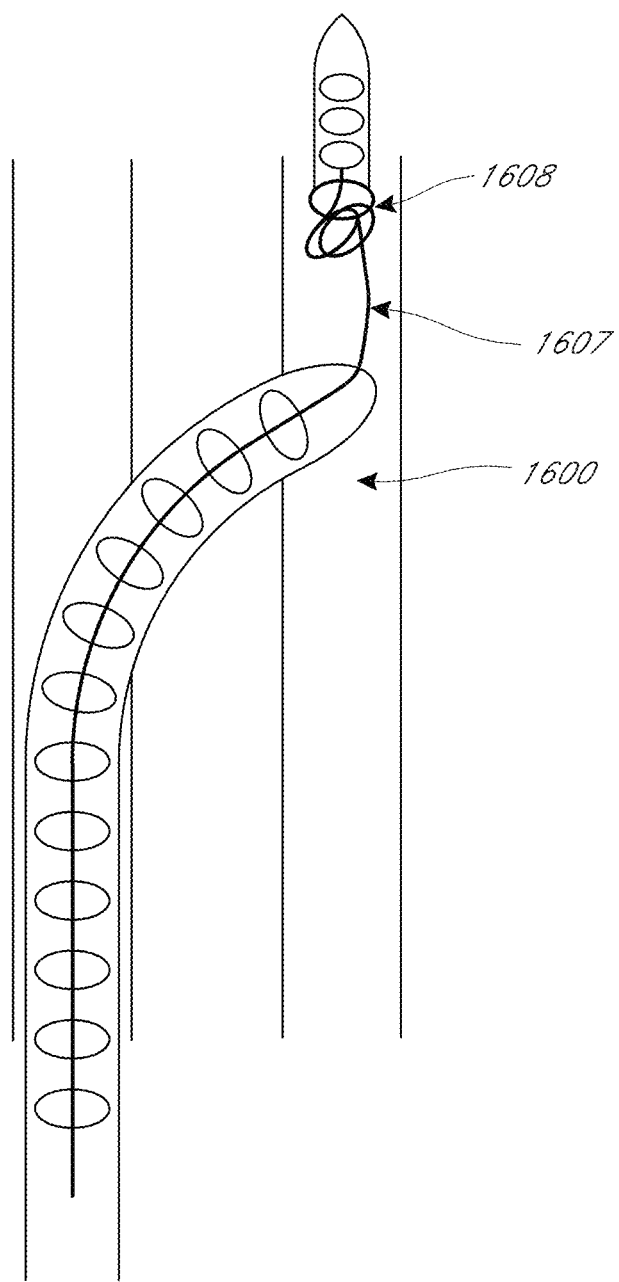

In some embodiments, a catheter system including any number of features as disclosed elsewhere herein can include an integrated converter functionality in which a first deployed guidewire can be conveniently replaced with a second guidewire. The second guidewire can have the same, or different characteristics than the first guidewire. In some embodiments, the second guidewire has a different diameter (e.g., larger or smaller), stiffness, distal tip shape, different magnetic properties, etc. with respect to the first guidewire. In some embodiments, the first guidewire has a 0.14" or 0.18" diameter, while the second guidewire has a 0.35" diameter. FIGS. 12A-12C schematically illustrates a method of replacing a first guidewire 1606 with a second guidewire 1607. FIG. 12A illustrates the first donor catheter 1600 within the first lumen L1, and the second receiving catheter 1602 within the second lumen L2, with the first guidewire 1606 having already passed through the luminal wall of the first lumen L1 and the external wall of the second lumen L2, and captured by the capture member 1608 (e.g., snare). The second guidewire 1607 remains within the first lumen L1 with its distal tip 1609 distal to the first guidewire 1606 within the first lumen L1. As shown schematically in FIG. 12B, the first catheter 1600 (along with the second guidewire) can be withdrawn proximally, with the distal tip of the first guidewire 1606 still operably attached to the capture member 1608. The first catheter 1600 can then be advanced over the first guidewire 1606 into the second lumen L2 as shown schematically in FIG. 12C, the first guidewire 1606 released from the capture member 1608, retracted, and then fully withdrawn, and the second guidewire 1607 advanced out of the first catheter 1600, and captured by the capture member 1608 if desired. The first catheter 1600 can then be withdrawn back into the first lumen L1.

Figure 12D:
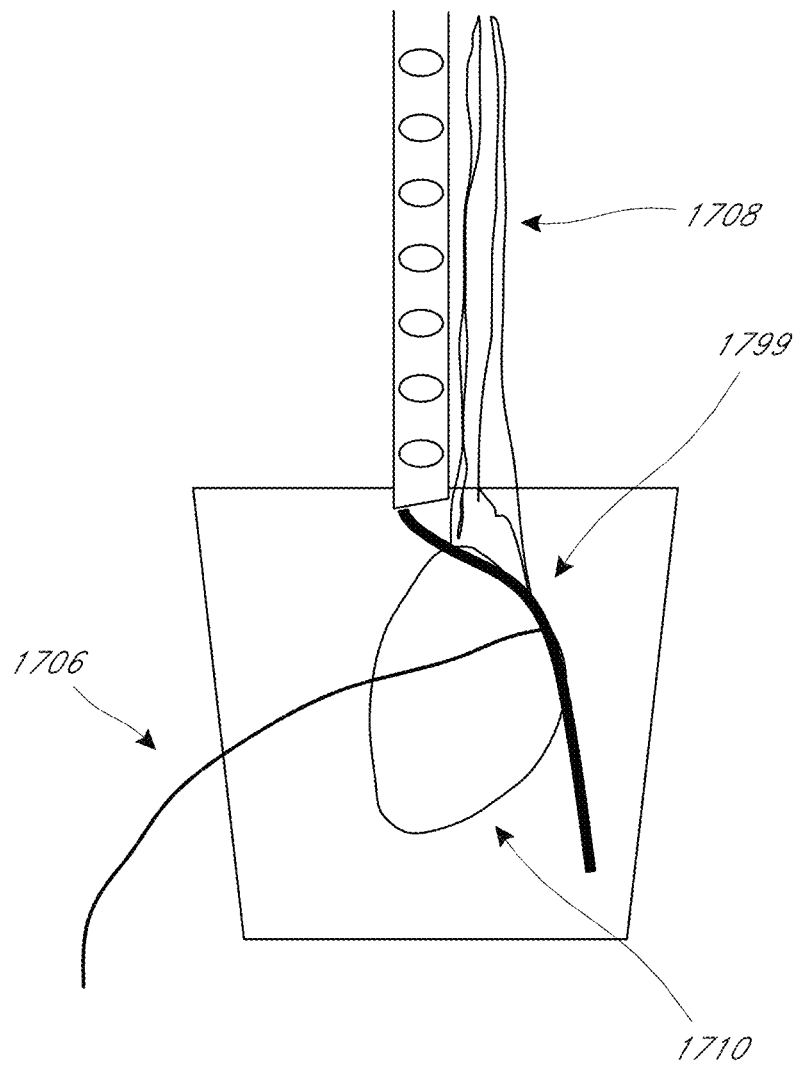
Figure 12E:
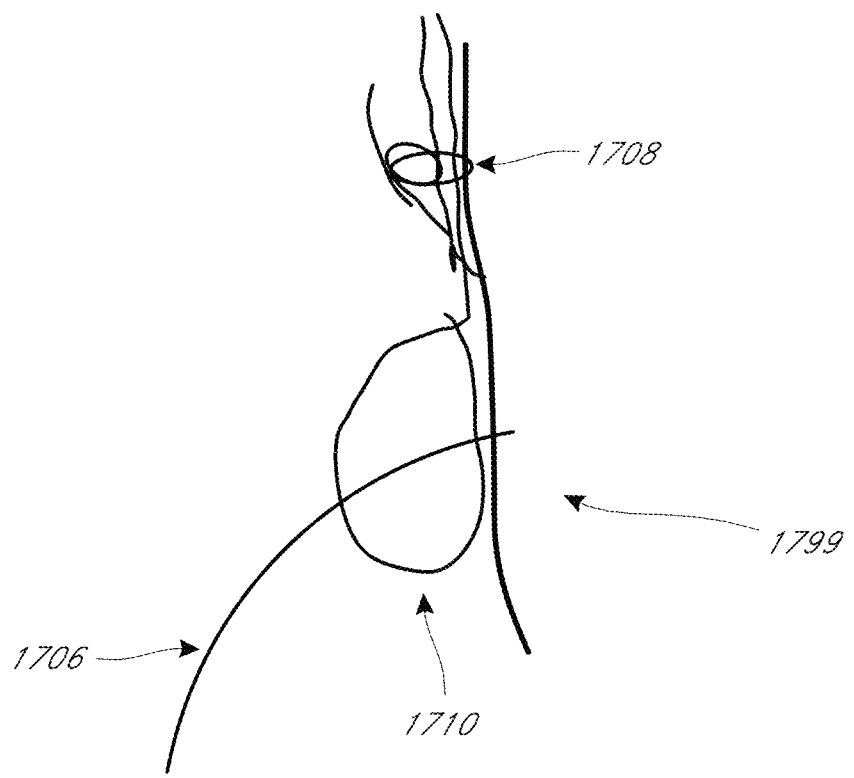

In some embodiments, a catheter system including any number of features as disclosed elsewhere herein can include a protection shield on the second (receiver) catheter configured to prevent undesired damage to the second lumen and associated anatomical structures, such as the puncture guidewire making an unintended through-and-through puncture, cautery, or the like through the second lumen. The protection shield can be configured to be deployed out of the catheter concurrently with the capture element, or be independently deployable in some embodiments. The protection shield can extend distally past the distal end of the catheter lumen and on one side of the catheter, to provide a mechanical shield to prevent undesired distal migration of the puncture guidewire, as well as to prevent any undesired cautery or other energy-based effectors of areas outside the target areas of the second lumen. In some embodiments, the protection shield is at least partially radiopaque to allow for more accurate positioning under imaging guidance. The protection shield can also have a solid wall in some embodiments, and can be flat, arcuate, fan-shaped, or other geometries. The protection shield can be configured to be expandable as well as contractable back into the second catheter after use. FIG. 12D schematically illustrates the capture element 1710 with protection shield 1799 on one side of the capture element 1710 opposite of the side that the puncture guidewire 1706 entered the second lumen from the first lumen. FIG. 12E schematically illustrates that the puncture guidewire 1706 is not able to pass distally past the protection shield 1799 advantageously for safety.

Figure 12F:
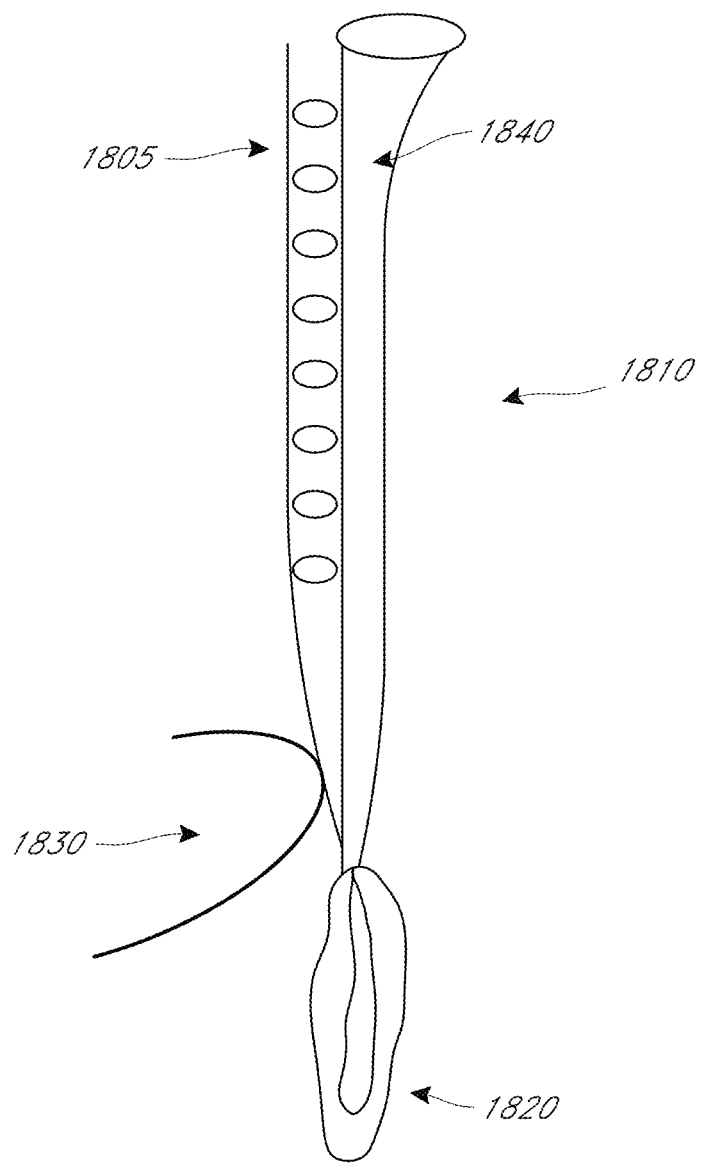
Figure 12G:
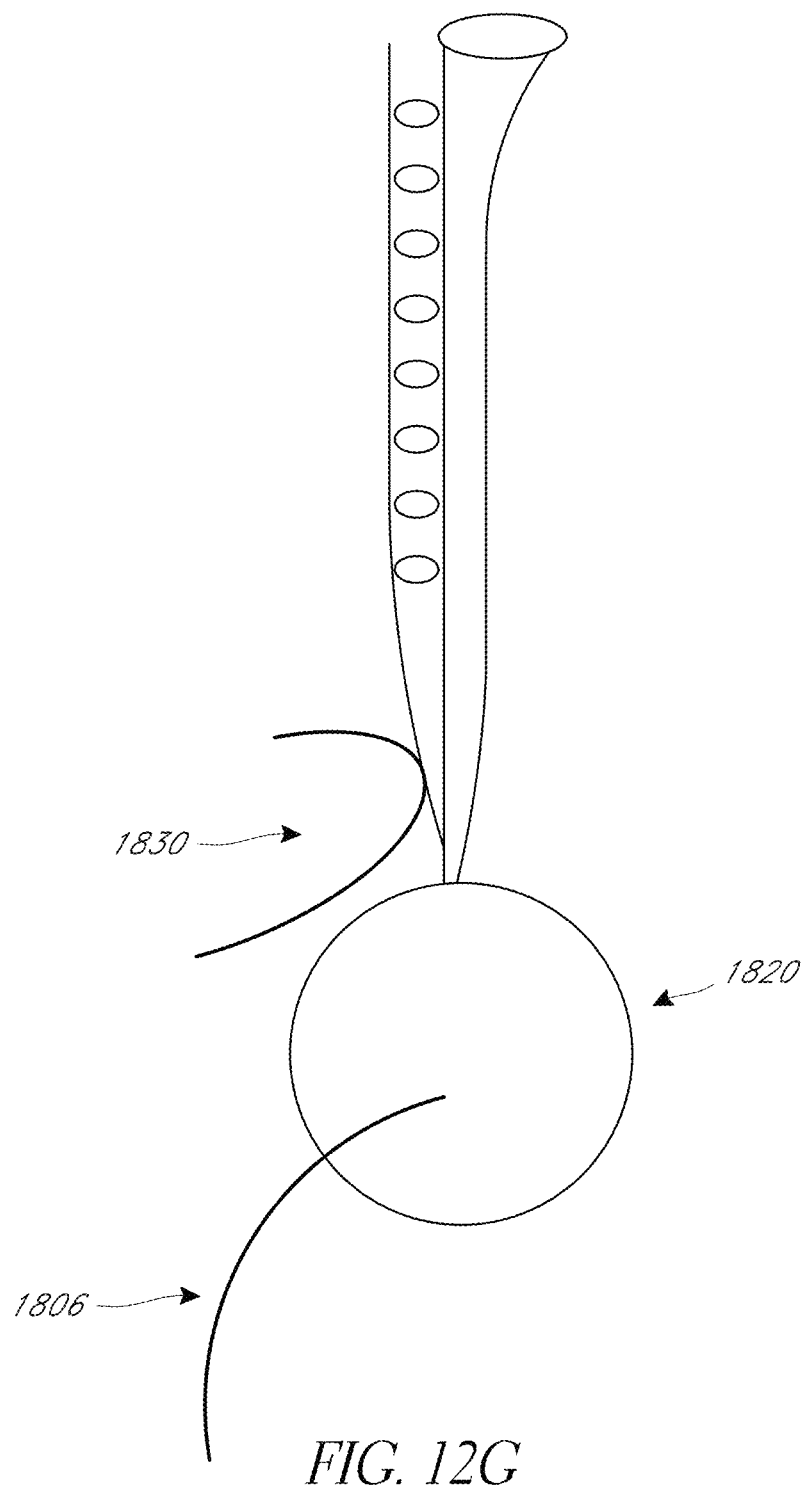
Figure 12H:
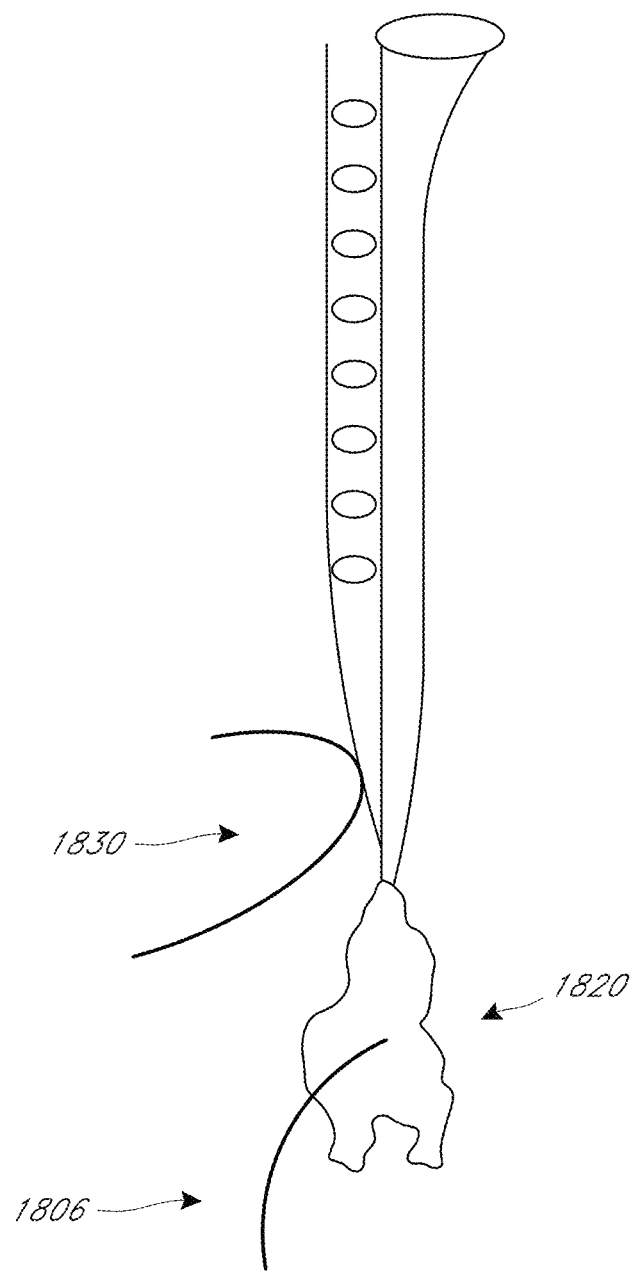
Figure 12I:
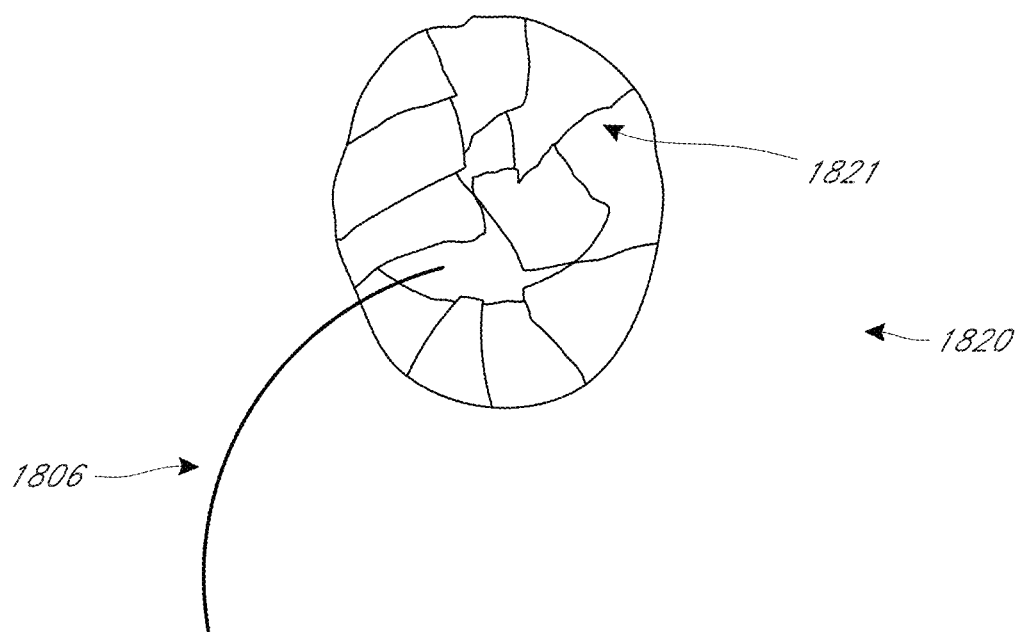

In some embodiments, a catheter system including any number of features as disclosed elsewhere herein can include a capture element that can be integrated into an expandable member such as an inflatable balloon associated with the second (receiver) catheter, but not the first (donor) catheter in some embodiments. The balloon can be a compliant balloon expandable to the diameter of the second (receiving) lumen. The second catheter can have a balloon inflation lumen that is a lumen configured to house a snare in other embodiments. FIG. 12F schematically illustrates a receiver catheter 1810 including magnetic elements 1805 and a rapid exchange guidewire element 1830 that can be as previously described (and that can be over-the-wire in other embodiments). A compliant balloon 1820 can be expanded to the diameter of the second (receiving) lumen, as shown in FIG. 12G, and the puncture guidewire (e.g., donor wire) 1806 can puncture the balloon wall. As shown in FIG. 12H, the punctured balloon 1820 can collapse down on the distal end of the puncture guidewire 1806, functionally serving as a capture element and securing the puncture guidewire 1806 to the receiver catheter 1810. The balloon 1820 could have a discrete snare or other capture element inside of the balloon 1820, or in some embodiments, the balloon 1820 alone is sufficient to secure the puncture guidewire 1806 to the receiver catheter 1810. As illustrated schematically in FIG. 12I, the balloon 1820 can also include an integrated mesh layer 1821, including nitinol or other shape memory or non shape-memory wires, fibers, an adhesive layer, and the like to assist in trapping/securing the donor wire 1806 to the balloon 1820.

FIGS. 12J-12N illustrate various non-limiting cross-sectional geometries of shapes of magnetic elements, according to some embodiments, including but not limited to square (FIG. 12J), cylindrical (FIG. 12K), elliptical (FIG. 12L), triangular (FIG. 12M), and semi-cylindrical or half-moon shaped (FIG. 12N).

Figure 12O:
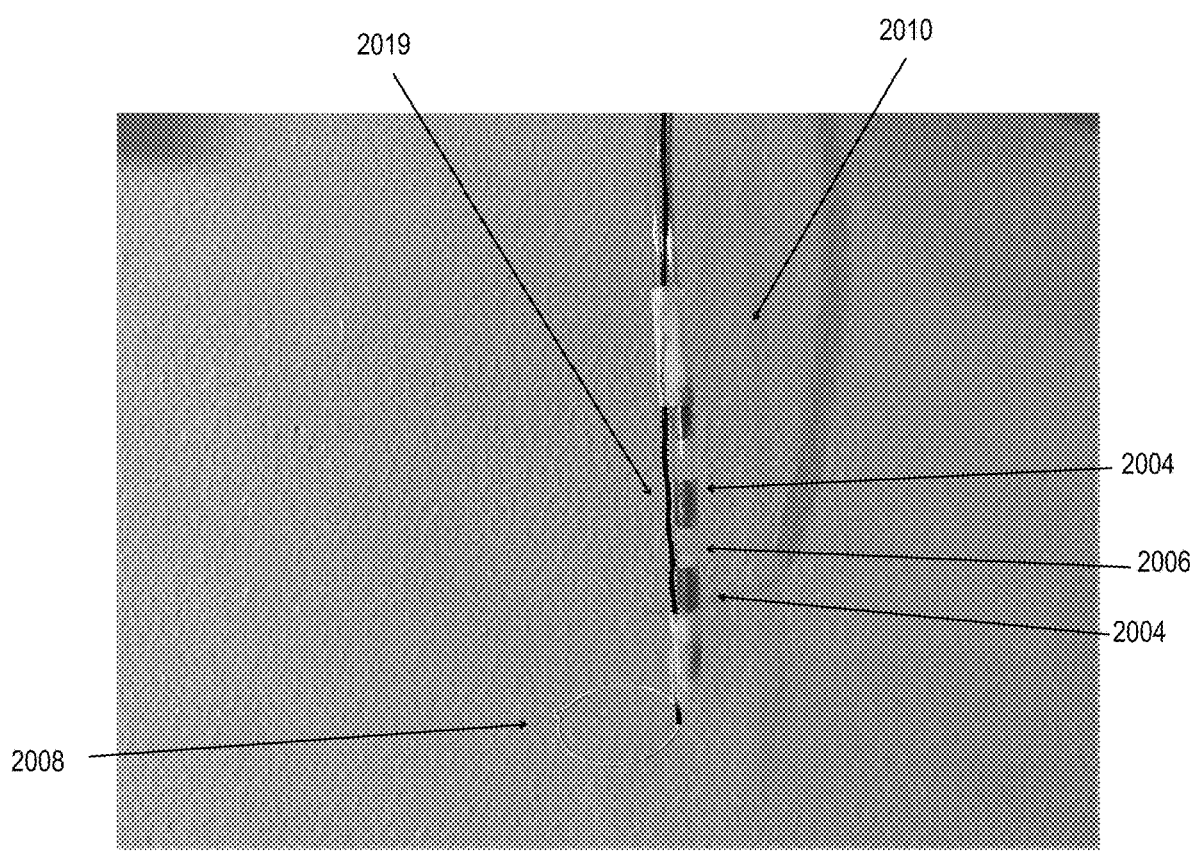

FIG. 12O schematically illustrates a perspective view of a distal portion of a receiver catheter 2010 including a plurality of axially-spaced apart magnets 2004 permanently interspersed by permanently fixed spacers 2006 in between adjacent magnets 2004. Also shown is a capture element 2008 (e.g., snare) extending distally from a capture element wire 2019.

Figure 12P:
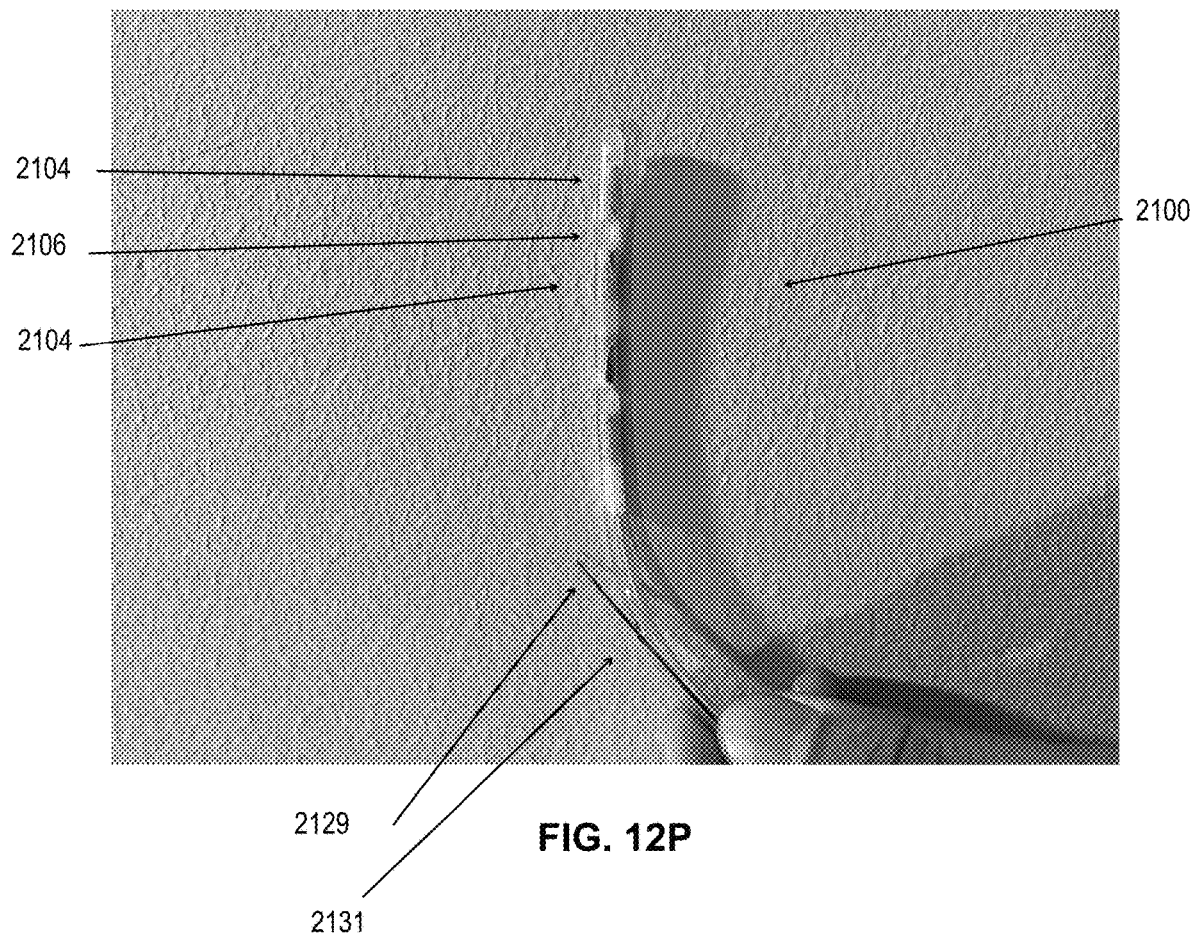

FIG. 12P schematically illustrates a distal portion of a donor catheter 2100 including a plurality of axially-spaced apart magnets 2104 permanently interspersed by fixed spacers 2106 in between adjacent magnets 2104. Also shown is a puncture guidewire 2129 extending distally from an aperture 2131 in the sidewall of the donor catheter, but proximal to the distal end of the donor catheter. The aperture 2131 can be connected to a puncture guidewire lumen that extends proximally to a port proximate the proximal end of the donor catheter 2100.

Figure 12Q:
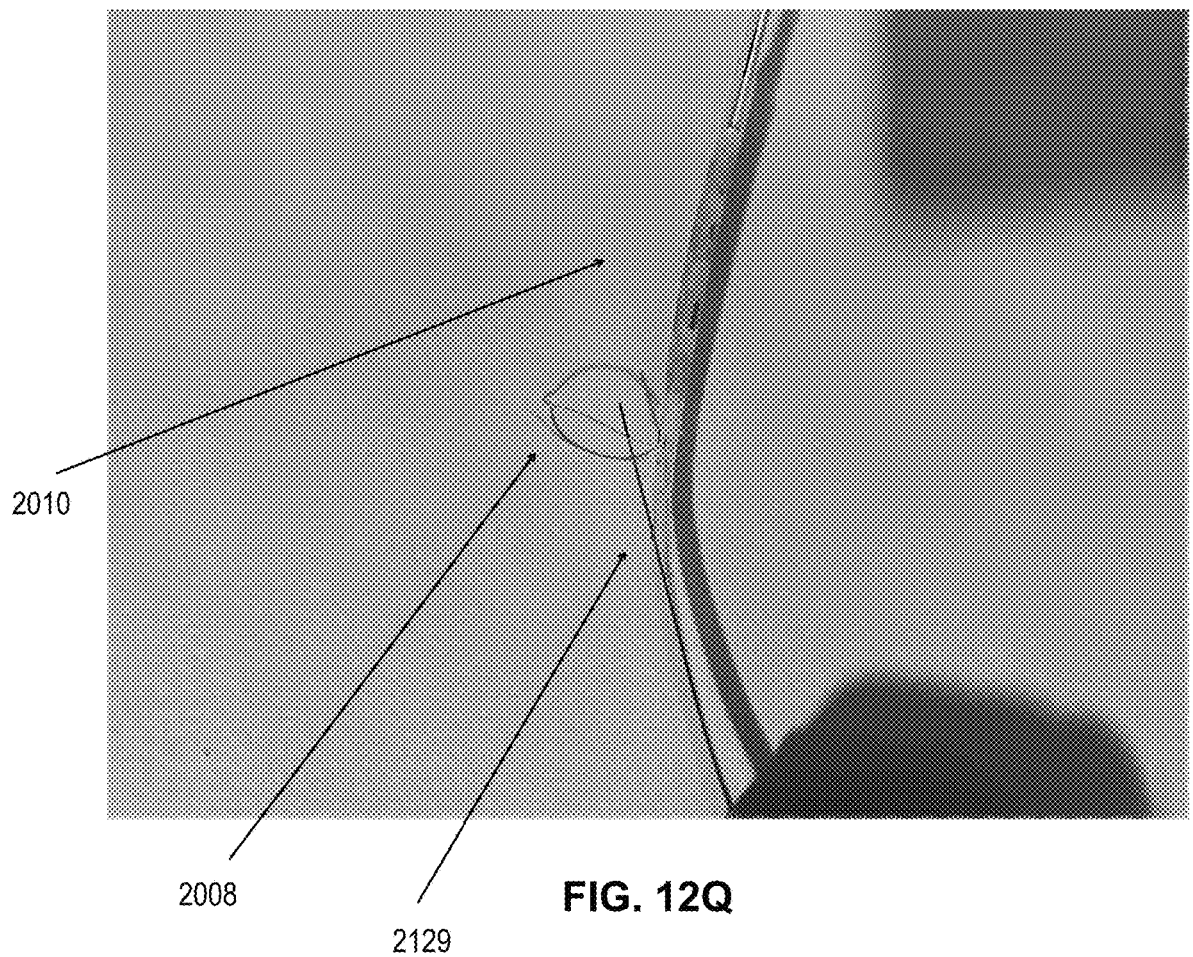

FIG. 12Q schematically illustrates the puncture guidewire 2129 extending into capture element 2008 of the receiver catheter 2010. Donor catheter is not shown for simplicity.

Figure 12R:
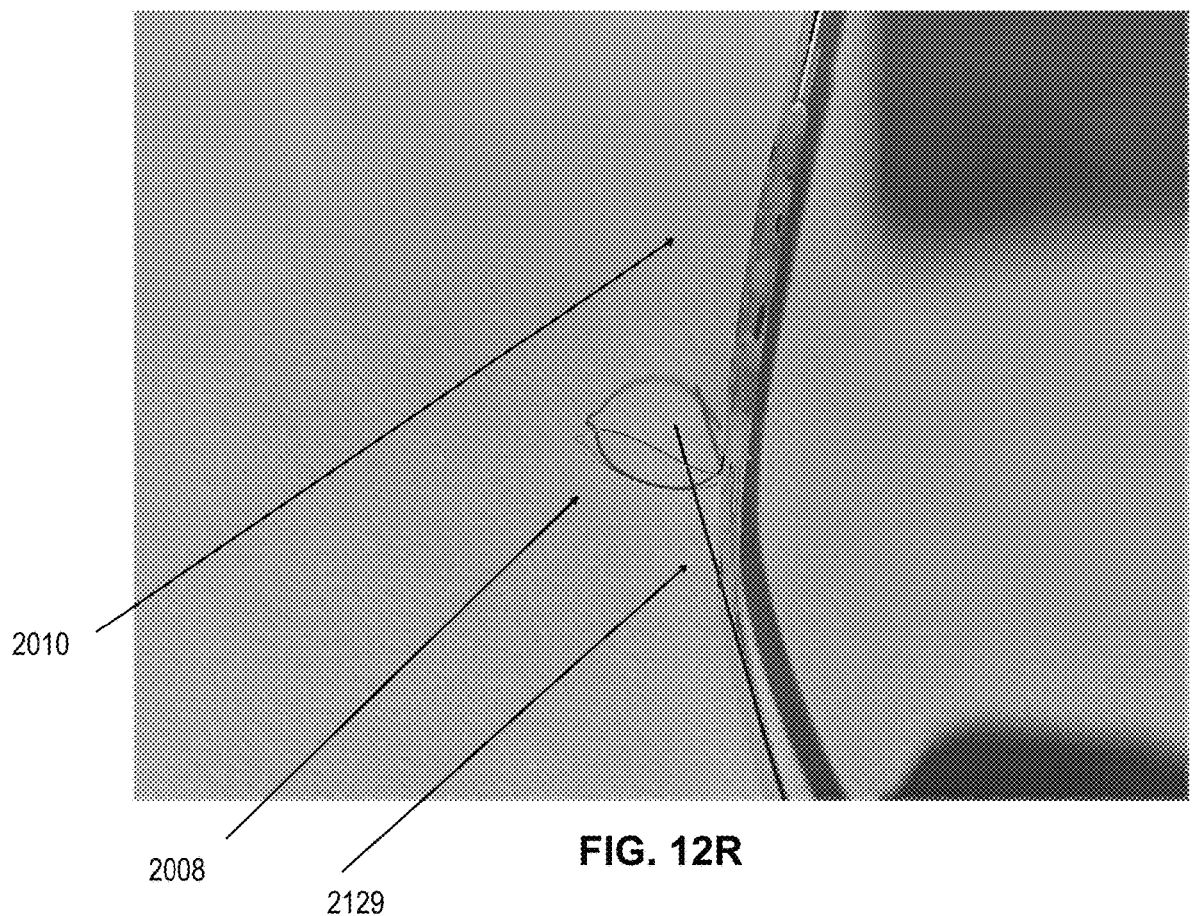

FIG. 12R schematically illustrates a slightly different view of puncture guidewire 2129 extending into capture element 2008 of the receiver catheter 2010.

Figure 12S:
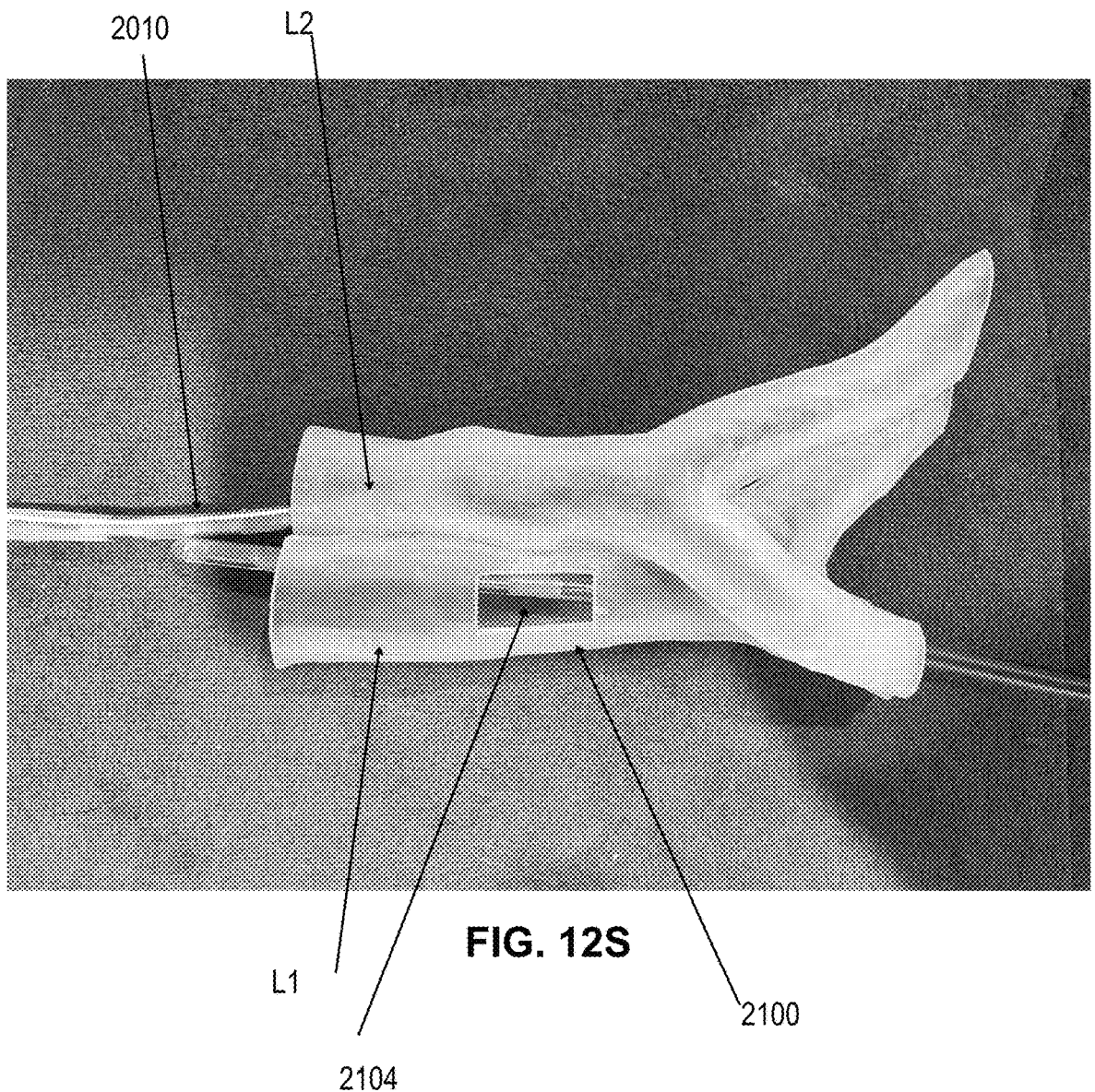

FIG. 12S schematically illustrates a cut-away view of first catheter 2100 in a first lumen L1 (e.g., the inferior vena cava), and second catheter 2010 in a second lumen L2 (e.g., the aorta). A cut-away portion in the wall of the first lumen L1 illustrates one of a plurality of magnetic elements 2104 of the first catheter that can attract complementary magnetic elements of the second catheter (not shown) to align the first and second lumens for a lumen-traversing procedure such as described elsewhere herein.

Figure 12T:
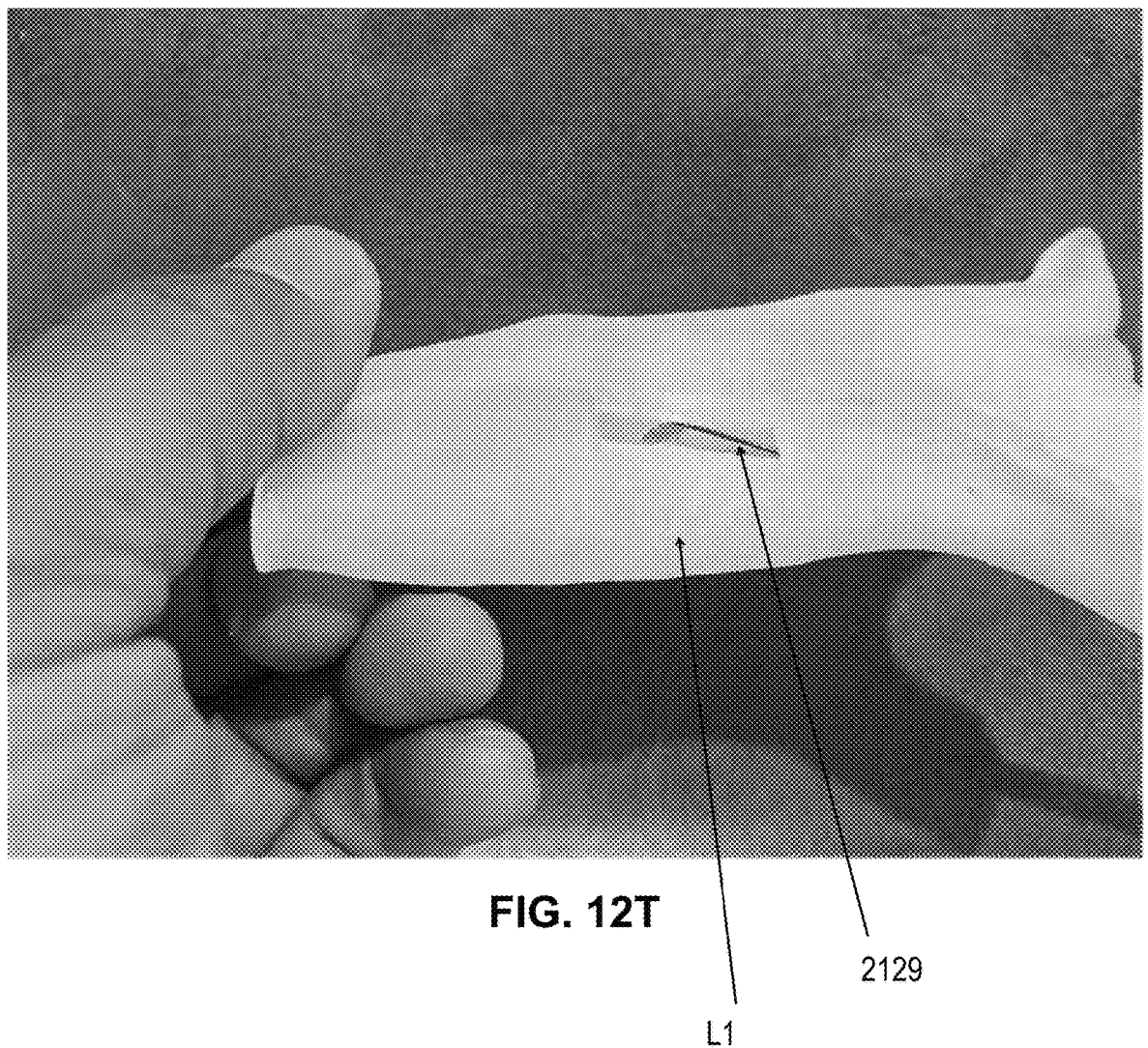

FIG. 12T schematically illustrates a cut-away portion of the first lumen L1 with puncture guidewire 2129 extending out of the donor catheter.

Figure 12U:
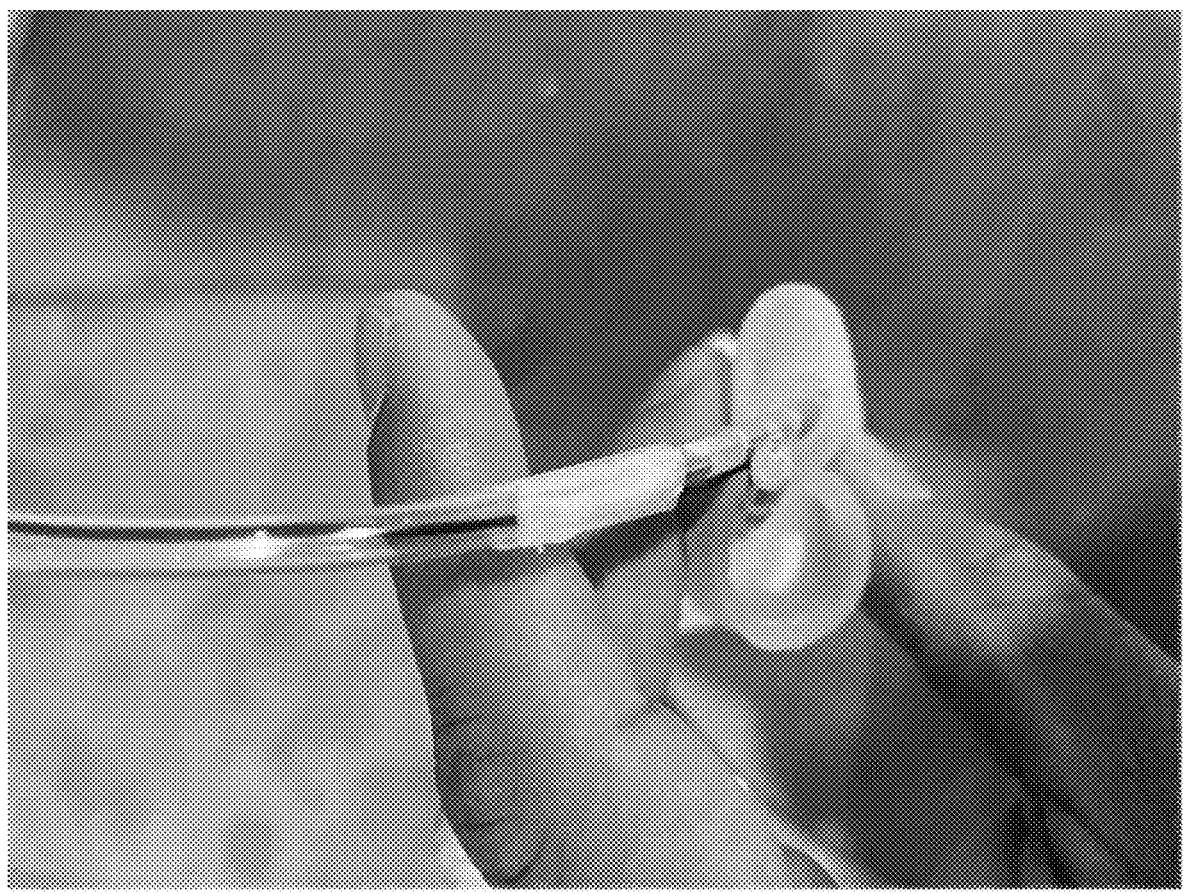

FIG. 12U schematically illustrates and end cut-away view, illustrating first and second catheters in their respective lumens being attracted by complementary magnets of each respective catheter.

Figure 13:
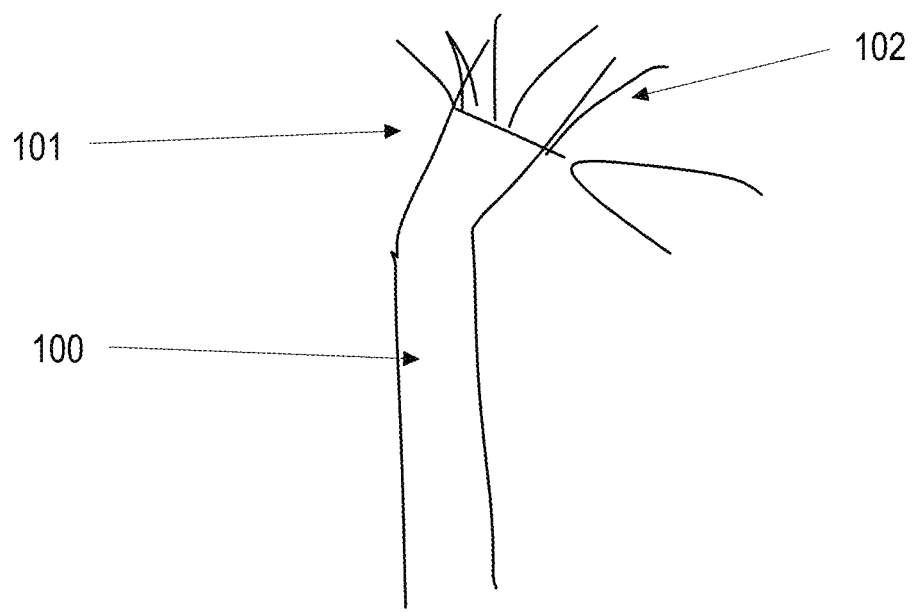
Figure 13A:
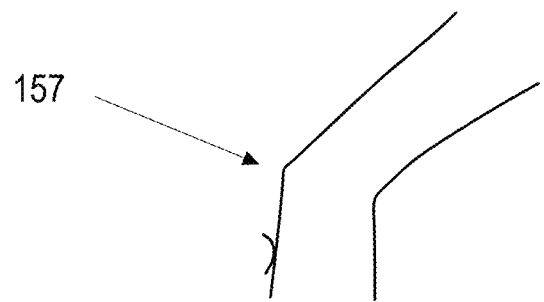

FIG. 13 schematically illustrates a distal end 101 of a catheter 100 that can include one or more magnetic elements 102. The outer and/or inner catheter could be steerable and curvable, such as articulating with bend region(s) 157 as shown schematically in FIG. 13A, with pullwires or a pre-bent shape memory distal end for example. In some embodiments, any number of the catheter, wire, and/or snares are steerable and curvable, either manually or automatically utilizing a remote (e.g., robot) controlled guidance system involving hardware and/or software processing. In some embodiments, a hardware controller can be configured to control arms or other actuators to manipulate any number of the donor catheter, receiving catheter, puncture guidewire, capture guide, and the like. The controller could be connected via wires or wirelessly to a remote terminal controlled by an operator providing inputs to the controller. The system can also include imaging guidance, such as CT, MRI, ultrasound, or X-ray imaging/fluoroscopy, for example that can also be controlled by the same or different controller. In some embodiments, the first catheter and the second catheter can include integrated imaging technology on one or both catheters themselves (e.g., endoscopic ultrasound) or other location technology.

Any portion of the catheter system can also include shape memory materials, such as metals (e.g., nitinol) or polymers that can be curved or steered by inputs, including thermal elements adjacent the shape memory materials that can allow the shape memory materials to change state.

Figure 13B:
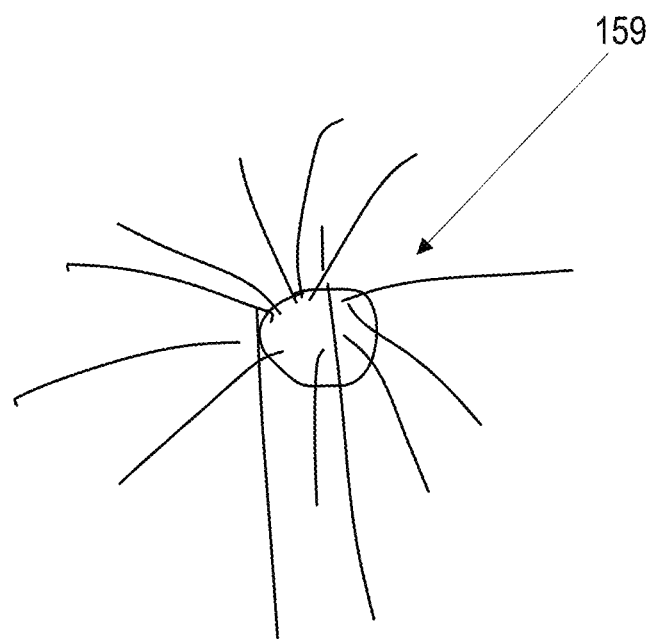
Figure 13:
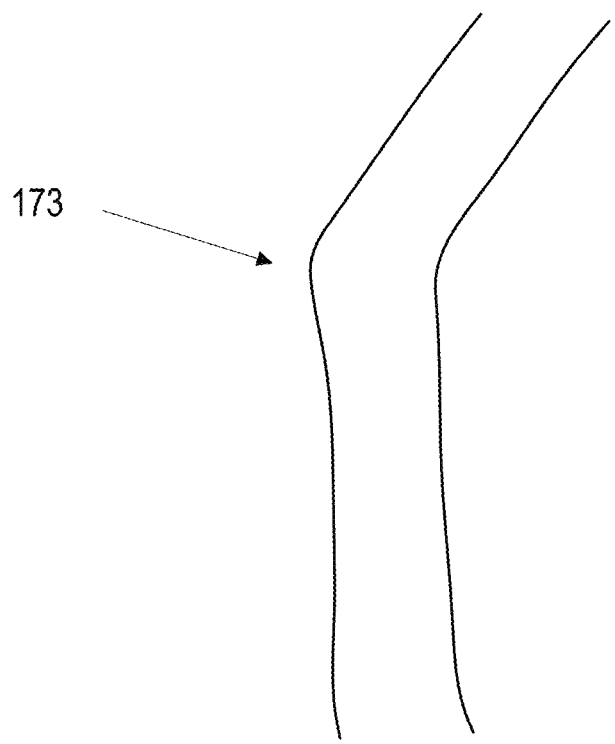
Figure 14:
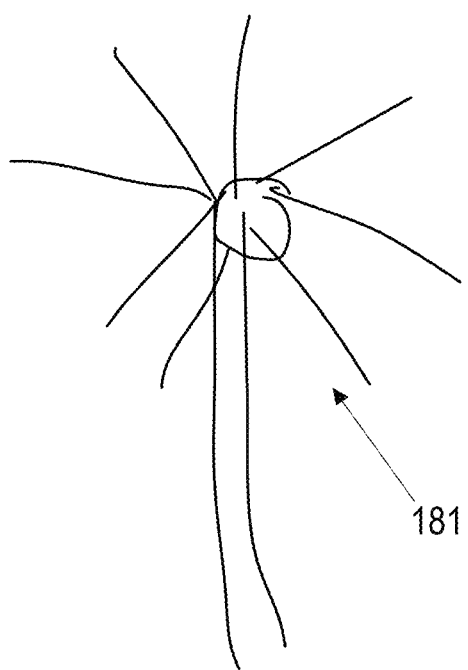

In some embodiments, an outer sheath 173 (shown schematically in FIG. 13C) can be removed, revealing an inner catheter with a distal end comprising a flower petal-like shape (shown schematically in FIGS. 13B and 14) with a plurality of radially expandable magnetic and/or non-magnetic tines or petals spaced radially symmetrically or asymmetrically apart along a circumference of the distal end of the inner catheter and extending radially outward from the catheter, apart from distal or side-facing end lumen 159. The tines or petals 181 can be configured to open together, or be separately/individually actuatable. In some embodiments, the level at which the petals are unsheathed could control the amount of magnets/magnetism utilized. In some embodiments, if electromagnets are utilized, each of these could be ferrite cores or cobalt iron cores, optionally coated with a material such as latex, silicone, etc. to make them inert. Each of those cores could be wrapped with an electrically conductive substance such as copper for example, that would be spun around them. The core elements could be flexible, or if not flexible ferrite the other options using solid ferrite in some embodiments. There can be a benefit of solid ferrite in some cases which is that solid surfaces tend to have greater core and greater core could relate to higher magnetism. A solid core with multiple hinge points could be similar to the arms of an umbrella as the hinges unsheath. The petals of the flower could open or expand sufficiently to have a surface area of contact with a lumen which could have the ability to institute a wire which would have a puncture capability, e.g., radio frequency or other ablation ability or a needle catheter depending on different applications, including for transcaval use.

Figure 16:
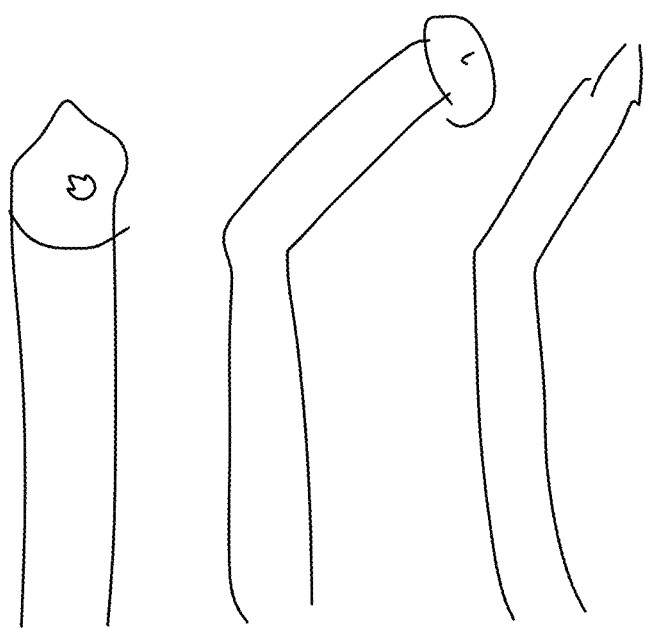

A variety of shapes is possible, as illustrated schematically in FIG. 16. The arms of the flower can be articulating with pullwires or other elements, or wire compressed or stiff systems. In some embodiments, each catheter could include about, at least about, or no more than about 2, 3, 4, 5, 6, 7, 8, 9, 10, 11, 12, 13, 14, 15, 16, 17, 18, 19, 20, or more or less expandable petals, tines, etc., or ranges including any two of the aforementioned values. Each catheter could include the same number, or a different number of expandable elements. Multiple other embodiments can include rounded ends, and/or be webbed including a mesh or other material for receiver and donor catheters to ensure that when magnets align, a seal with GoreTex or other material is present to prevent bleeding during approximation of tissue planes. In some embodiments, magnetic elements can be unsheathed or pushed out or a part of the outer sheath system or separate with inner and outer sheaths. Sizes can range from micro to macro size pending application. Sheath systems can flex to arrange the magnets using a pull tab on outside or rotating dial and wire braiding allowing alignment of magnets.

In some embodiments, magnets could be any of, or any combination of the following: electromagnets; rare earth magnets; neodymium (magnet strength can be based on type or size of magnet); a true iron ferrite core. Insulating material can be utilized for protection of electrified wire from the device. A rare earth magnet could include a magnet including any number of a collection of seventeen chemical elements in the periodic table, including scandium, yttrium, the fifteen lanthanoids, and any combination thereof. The fifteen lanthanoids include lanthanum, cerium, praseodymium, neodymium, promethium, samarium, europium, gadolinium, terbium, dysprosium, holmium, erbium, thulium, ytterbium, and lutetium. In some embodiments, a magnet may be a permanent magnet made of ferromagnetic materials, or made from compositions including rare-earth materials, such as neodymium-iron boron-43 (NdFeB-43), neodymium-iron boron-45 (NdFeB-45), neodymium-iron boron-48 (NdFeB-48) or neodymium-iron boron-50 (NdFeB-50), for example. In some embodiments, the electromagnets can be in contact with a power source configured to adjust the power of the electromagnets as needed during the procedure in a stepwise or continuous fashion. An operator can actuate a control, e.g., on the power source or proximal end of the device(s) for example to increase or decrease the power of all or a subset of the electromagnets on either the first device, the second device, or both devices.

Some embodiments could include a catheter configured to house a puncture guidewire that comprises an electrified wire with electrocautery attached to generator with a special distal tip for puncture, or a tip that extends laterally out of a sidewall of a catheter in some embodiments. In some embodiments, a needle puncture system replaces an electrified guidewire. In some embodiments, a radiofrequency, microwave, HIFU, or other electromagnetic, optical, thermal, cryo, mechanical, chemical, or other puncture system can be used rather than an electrified wire or needle. Some optical systems can utilize a laser configured to create the puncture, and advantageously prevent the physical pushing away of the magnets during puncture. The laser could be, for example, a $CO_2$, Holmium:YAG, Nd:YAG, ruby, helium-neon, KTP:Nd:YAG, or argon laser. As such, some systems can include catheters with atraumatic distal tips, although a sharpened distal tip can be used in other embodiments. Other possibilities can include puncturing from a donor to a receiver. Systems can include a power source such as a battery or AC source to power the cautery device, electromagnets, etc.

In some embodiments, a device can be used at the end of a procedure to deploy a clamp that can be arranged in-line. The closure device can be proprietary, magnet based or can be a commercially available closure device which can be passed inside the sheath and deployed.

EXAMPLE EMBODIMENTS

The following are non-limiting examples of certain embodiments of magnetic puncture access and delivery systems and methods. Other embodiments may include one or more other features, or different features, that are discussed herein.

Embodiment 1: A catheter system, comprising: a first catheter comprising a proximal end, a distal end, and a plurality of magnetic elements axially aligned along a longitudinal axis of the first catheter, a second catheter comprising a proximal end, a distal end, and a plurality of magnetic elements axially aligned along a longitudinal axis of the second catheter, wherein the magnetic elements of the first catheter and the magnetic elements of the second catheter are configured to align the first catheter and the second catheter when the first catheter and second catheter are placed within first and second body lumens.

Embodiment 2: The catheter system of Embodiment 1, wherein the second catheter comprises the same number of magnetic elements as the first catheter.

Embodiment 3: The catheter system of Embodiment 1, wherein the second catheter comprises a different number of magnetic elements as the first catheter.

Embodiment 4: The catheter system of any one of Embodiments 2 or 3, wherein the first catheter and the second catheter each comprise between 2 and 15 magnetic elements.

Embodiment 5: The catheter system of any one of Embodiments 1-4, wherein each of the plurality of magnetic elements of the first catheter and the second catheter directly contact each other.

Embodiment 6: The catheter system of any one of Embodiments 1-4, wherein each of the plurality of magnetic elements of the first catheter and the second catheter are spaced longitudinally apart from each other.

Embodiment 7: The catheter system of Embodiment 6, wherein each of the plurality of magnetic elements of the first catheter are spaced longitudinally apart from each other by a distance of about 0.5 cm or less.

Embodiment 8: The catheter system of any one of Embodiments 6 or 7, wherein each of the plurality of magnetic elements of the first catheter are spaced longitudinally apart from each other by non-magnetic spacers.

Embodiment 9: The catheter system of Embodiment 8, wherein the non-magnetic spacers comprise a flexible material.

Embodiment 10: The catheter system of Embodiment 9, wherein the flexible material comprises a polymer.

Embodiment 11: The catheter system of any one of Embodiments 8-10, wherein each of the plurality of magnetic elements comprises an axial length that is greater than or equal to an axial length of each of the non-magnetic spacers.

Embodiment 12: The catheter system of any one of Embodiments 8-10, wherein each of the plurality of magnetic elements comprises an axial length that is greater than an axial length of each of the non-magnetic spacers.

Embodiment 13: The catheter system of any one of Embodiments 1-12, wherein the first catheter and second catheter are configured to be steerable and curvable.

Embodiment 14: The catheter system of Embodiment 13, wherein the first catheter and second catheter each comprise pullwires operably connected proximally to a control.

Embodiment 15: The catheter system of any one of Embodiments 1-14, wherein the magnetic elements of the first catheter and the second catheter comprise electromagnets.

Embodiment 16: The catheter system of any one of Embodiments 1-14, wherein the magnetic elements of the first catheter and the second catheter comprise permanent magnets.

Embodiment 17: The catheter system of any one of Embodiments 1-16, wherein the magnetic elements of the first catheter and the second catheter have a magnetic flux density of between about 3,000 and 10,000 Gauss measured at a point on the surface of one of the magnetic elements.

Embodiment 18: The catheter system of any one of Embodiments 1-17, wherein the first catheter comprises a snare element configured to be housed within a lumen of the first catheter.

Embodiment 19: The catheter system of any one of Embodiments 1-18, wherein the second catheter comprises a guidewire configured to be housed within a lumen of the first catheter.

Embodiment 20: The catheter system of any one of Embodiments 1-19, wherein the first catheter and the second catheter comprise non-magnetic distal tips.

Embodiment 21: A catheter, comprising: a proximal end, a distal end, and a plurality of magnetic elements axially aligned along a longitudinal axis of the first catheter, wherein the magnetic elements of the first catheter are configured to align with magnetic elements of a second catheter when the first catheter and second catheter are placed within first and second body lumens.

Embodiment 22: A method of creating an access pathway between a first body lumen and a second body lumen, comprising: positioning a first catheter in a first body lumen, the first catheter comprising a proximal end, a distal end, and a plurality of magnetic elements axially aligned along a longitudinal axis of the first catheter; positioning a second catheter in a second body lumen, the second catheter comprising a proximal end, a distal end, and a plurality of magnetic elements axially aligned along a longitudinal axis of the second catheter; aligning the first catheter and the second catheter at least in part via the plurality of magnetic elements of the first catheter and the second catheter; positioning a capture element in the second body lumen by moving the capture element distally out of a lumen of the second catheter; positioning a wire in the first body lumen by moving the wire out of a lumen of the first catheter; creating an access pathway between the first body lumen and the second body lumen; advancing the wire through the access pathway and into the second body lumen; coupling a portion of the wire to the capture element; withdrawing the second catheter within the second body lumen, thereby increasing a length of the wire present within the second body lumen; and releasing the wire from the capture element, thereby maintaining the wire within the second body lumen and the first body lumen, and spanning the access pathway.

Embodiment 23: The method of Embodiment 22, further comprising advancing a sheath over the wire through the first body lumen, across the access pathway, and into the second body lumen.

Embodiment 24: The method of Embodiment 23, wherein a medical device is operably coupled to the sheath.

Embodiment 25: The method of Embodiment 24, wherein the medical device comprises a replacement heart valve.

Embodiment 26: The method of any one of Embodiments 24 or 25, wherein the medical device comprises a ventricular assist device.

Embodiment 27: The method of any one of Embodiments 22-26, wherein the first body lumen is the inferior vena cava, and the second body lumen is the aorta.

Embodiment 28: The method of any one of Embodiments 22-26, wherein the first body lumen is the superior vena cava, and the second body lumen is the aorta.

Embodiment 29: The method of any one of Embodiments 22-26, wherein the first body lumen is a first cardiac chamber, and the second body lumen is a second cardiac chamber.

Embodiment 30: The method of any one of Embodiments 22-26, wherein the first body lumen is a vein, and the second body lumen is an artery.

Embodiment 31: The method of any one of Embodiments 22-26, wherein the first body lumen is an artery, and the second body lumen is a vein.

Embodiment 32: The method of any one of Embodiments 22-26, wherein the first body lumen is a vascular lumen, and the second body lumen is a non-vascular lumen.

Embodiment 33: The method of any one of Embodiments 22-26, wherein the first body lumen is a non-vascular lumen, and the second body lumen is a non-vascular lumen.

Embodiment 34: The method of any one of Embodiments 22-33, wherein the second catheter comprises the same number of magnetic elements as the first catheter.

Embodiment 35: The method of any one of Embodiments 22-33, wherein the second catheter comprises a different number of magnetic elements as the first catheter.

Embodiment 36: The method of any one of Embodiments 22-35, wherein the first catheter and the second catheter each comprise between 2 and 15 magnetic elements.

Embodiment 37: The method of any one of Embodiments 22-36, wherein each of the plurality of magnetic elements of the first catheter and the second catheter directly contact each other.

Embodiment 38: The method of any one of Embodiments 22-36, wherein each of the plurality of magnetic elements of the first catheter and the second catheter are spaced longitudinally apart from each other.

Embodiment 39: The method of Embodiment 38, wherein each of the plurality of magnetic elements of the first catheter are spaced longitudinally apart from each other by a distance of about 0.5 cm or less.

Embodiment 40: The method of any one of Embodiments 38 or 39, wherein each of the plurality of magnetic elements of the first catheter are spaced longitudinally apart from each other by non-magnetic spacers.

Embodiment 41: The method of Embodiment 40, wherein the non-magnetic spacers comprise a flexible material.

Embodiment 42: The method of Embodiment 41, wherein the flexible material comprises a polymer.

Embodiment 43: The method of any one of Embodiments 40-42, wherein each of the plurality of magnetic elements comprises an axial length that is greater than or equal to an axial length of each of the non-magnetic spacers.

Embodiment 44: The method of any one of Embodiments 40-42, wherein each of the plurality of magnetic elements comprises an axial length that is greater than an axial length of each of the non-magnetic spacers.

Embodiment 45: The method of any one of Embodiments 22-44, further comprising deflecting at least one of the first catheter and the second catheter.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "approximating a first vessel wall with respect to a second vessel wall" includes "instructing the approximating of a first vessel wall with respect to a second vessel wall."

The invention claimed is:

1. A catheter system, comprising:
   a first catheter comprising a proximal end, a distal end, a sidewall port, and a plurality of magnetic elements axially aligned along a longitudinal axis of the first catheter, and
   a second catheter comprising a proximal end, a distal end, a distal end port, and a plurality of magnetic elements axially aligned along a longitudinal axis of the second catheter,
   a puncture element configured to extend out of the sidewall port of the first catheter, and
   a capture element configured to extend out of the distal end port of the second catheter,
   wherein the magnetic elements of the first catheter and the magnetic elements of the second catheter are configured to align the first catheter and the second catheter when the first catheter and second catheter are placed within first and second body lumens,
   wherein each of the plurality of magnetic elements of the first catheter and the second catheter are spaced longitudinally apart from each other by non-magnetic spacers,
   wherein the non-magnetic spacers are permanently fixed in between adjacent magnetic elements of the plurality of magnetic elements when the first catheter is in a deployed configuration,
   wherein the non-magnetic spacers do not include an elongate cord member therethrough.

2. The catheter system of claim 1, wherein the non-magnetic spacers comprise a flexible material.

3. The catheter system of claim 2, wherein the flexible material comprises a polymer.

4. The catheter system of claim 1, wherein the second catheter comprises the same number of magnetic elements as the first catheter.

5. The catheter system of claim 1, wherein the second catheter comprises a different number of magnetic elements as the first catheter.

6. The catheter system of claim 1, wherein the first catheter and the second catheter each comprise between 2 and 15 magnetic elements.

7. The catheter system of claim 1, wherein each of the plurality of magnetic elements of the first catheter are spaced longitudinally apart from each other by a distance of about 0.5 cm or less.

8. The catheter system of claim 1, wherein each of the plurality of magnetic elements comprises an axial length that is greater than or equal to an axial length of each of the non-magnetic spacers.

9. The catheter system of claim 1, wherein each of the plurality of magnetic elements comprises an axial length that is greater than an axial length of each of the non-magnetic spacers.

10. A catheter system, comprising:
a first catheter comprising a proximal end, a distal end, a sidewall port and a plurality of magnetic elements axially aligned along a longitudinal axis of the first catheter, and
a second catheter comprising a proximal end, a distal end, a distal end port, and a plurality of magnetic elements axially aligned along a longitudinal axis of the second catheter,
a puncture element configured to extend out of the sidewall port of the first catheter, and
a capture element configured to extend out of the distal end port of the second catheter,
wherein the magnetic elements of the first catheter and the magnetic elements of the second catheter are configured to align the first catheter and the second catheter when the first catheter and second catheter are placed within first and second body lumens,
wherein each of the plurality of magnetic elements of the first catheter and the second catheter are spaced longitudinally apart from each other by non-magnetic spacers, wherein the non-magnetic spacers are permanently fixed in between adjacent magnetic elements of the plurality of magnetic elements when the first catheter is in a deployed configuration.

11. The catheter system of claim 10, wherein the first catheter and second catheter are configured to be steerable and curvable.

12. The catheter system of claim 10, wherein the first catheter and second catheter each comprise pullwires operably connected proximally to a control.

13. The catheter system of claim 10, wherein the magnetic elements of the first catheter and the second catheter comprise electromagnets.

14. The catheter system of claim 10, wherein the magnetic elements of the first catheter and the second catheter comprise permanent magnets.

15. The catheter system of claim 10, wherein the magnetic elements of the first catheter and the second catheter have a magnetic flux density of between about 3,000 and 10,000 Gauss measured at a point on the surface of one of the magnetic elements.

16. The catheter system of claim 10, wherein the first catheter comprises a snare element configured to be housed within a lumen of the first catheter.

17. The catheter system of claim 10, wherein the second catheter comprises a guidewire configured to be housed within a lumen of the first catheter.

18. The catheter system of claim 10, wherein the first catheter and the second catheter comprise non-magnetic distal tips.

19. A catheter system, comprising:
a first catheter comprising a proximal end, a distal end, a sidewall port, and a plurality of magnetic elements,
a second catheter comprising a proximal end, a distal end, a distal end port, and a plurality of magnetic elements;
a puncture element configured to extend out of the sidewall port of the first catheter; and
a capture element configured to extend out of the distal end port of the second catheter,
wherein each of the plurality of magnetic elements of the first catheter and the second catheter are spaced longitudinally apart from each other by non-magnetic flexible spacers,
wherein the non-magnetic flexible spacers are permanently fixed in between adjacent magnetic elements of the plurality of magnetic elements when the catheter is in a deployed configuration.

20. The catheter system of claim 19, wherein the distal end of the first catheter and the second catheter is non-magnetic.

* * * * *